(12) United States Patent
Desir

(10) Patent No.: US 10,941,212 B2
(45) Date of Patent: Mar. 9, 2021

(54) COMPOSITIONS AND METHODS FOR DETECTING, TREATING AND PREVENTING DISEASES AND DISORDERS

(71) Applicant: YALE UNIVERSITY, New Haven, CT (US)

(72) Inventor: Gary Desir, Woodbridge, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/106,338

(22) Filed: Aug. 21, 2018

(65) Prior Publication Data

US 2019/0031777 A1    Jan. 31, 2019

Related U.S. Application Data

(63) Continuation of application No. 14/414,734, filed as application No. PCT/US2013/050660 on Jul. 16, 2013, now Pat. No. 10,066,025.

(60) Provisional application No. 61/671,826, filed on Jul. 16, 2012, provisional application No. 61/750,916, filed on Jan. 10, 2013, provisional application No. 61/813,778, filed on Apr. 19, 2013.

(51) Int. Cl.
| | |
|---|---|
| *C07K 16/40* | (2006.01) |
| *A61K 38/44* | (2006.01) |
| *C12Q 1/26* | (2006.01) |
| *G01N 33/573* | (2006.01) |
| *G01N 33/68* | (2006.01) |
| *C12Q 1/6883* | (2018.01) |

(52) U.S. Cl.
CPC .............. *C07K 16/40* (2013.01); *A61K 38/44* (2013.01); *C12Q 1/26* (2013.01); *C12Q 1/6883* (2013.01); *G01N 33/573* (2013.01); *G01N 33/6893* (2013.01); *C07K 2317/24* (2013.01); *C07K 2317/622* (2013.01); *C07K 2317/75* (2013.01); *C12Q 2600/118* (2013.01); *C12Q 2600/158* (2013.01); *C12Y 106/03* (2013.01); *G01N 2333/90209* (2013.01); *G01N 2333/90633* (2013.01); *G01N 2800/321* (2013.01); *G01N 2800/325* (2013.01); *G01N 2800/347* (2013.01)

(58) Field of Classification Search
CPC .................................. C12N 9/002; C07K 16/40
See application file for complete search history.

(56) References Cited

U.S. PATENT DOCUMENTS

| | | |
|---|---|---|
| 7,700,095 B2 | 4/2010 | Xu |
| 2009/0181380 A1 | 7/2009 | Belouchi et al. |
| 2010/0136651 A1 | 6/2010 | Xu et al. |
| 2012/0178914 A1 | 7/2012 | Henderson et al. |

FOREIGN PATENT DOCUMENTS

WO    2007059357 A1    5/2007

OTHER PUBLICATIONS

Desir. 2009; Regulation of blood pressure and cardiovascular function by renalase. Kidney International. 76: 366-3710.*
Desir, "Regulation of blood pressure and cardiovascular function by renalase," 2009, Kidney International, 76: 366-370.
Xu et al., "Renalase is a novel, soluble monoamine oxidase that regulates cardiac function and blood pressure," 2005, J Clin Invest, 115: 1275-1280.
Li et al., "Catecholamines regulate the activity, secretion, and synthesis of renalase," 2008, Circulation, 117: 1277-1282.
Desir et al, "Renalase Lowers Ambulatory Blood Pressure by Metabolizing Circulating Adrenaline," 2012, J. of the Am. Heart Assn, 1(4):e002634.
Lee et al., "Renalase Protects against Ischemic AKI," 2013, J Am Soc Nephrol, 24:445-455.
Hennebry et al., "Renalase, a novel soluble FAD-dependent protein, is synthesized in the brain and peripheral nerves," 2010, Mol Psychiatry, 15:234-236.
Milani et al., "FAD-binding site and NADP reactivity in human renalase: a new enzyme involved in blood pressure regulation," 2011, J Mol Biol, 411:463-473.
Desir, "Novel insights into the physiology of renalase and its role in hypertension and heart disease," 2012, Pediatr Nephrol, 27: 719-725.
Desir, "Role of renalase in the regulation of blood pressure and the renal dopamine system," 2011, Curr Opin Nephrol Hypertens, 20: 31-36.
Wu et al., "Renalase deficiency aggravates ischemic myocardial damage," 2011, Kidney Int, 79: 853-860.
Gu et al., "Renalase deficiency in heart failure model of rats—A potential mechanism underlying circulating norepinephrine accumulation", PLoS One 2011, vol. 6, No. 1, 314633 (8 pages).
Jiang et al., "Impact of renal denervation on renalase expression in adult rats with spontaneous hypertension", Exp Ther Med, Epub Jun. 20, 2012, vol. 4, No. 3, p. 493-496.
Desir et al, 'Renalase Lowers Ambulatory Blood Pressure by Metabolizing Circulating Adrenaline,' 2012, J. of the Am. Heart Assn, 1(4):e002634. 11 pages.
Notice of Allowance dated May 1, 2018 for U.S. Appl. No. 14/414,734 (pp. 1-8).

* cited by examiner

*Primary Examiner* — Karen Cochrane Carlson
(74) *Attorney, Agent, or Firm* — Riverside Law LLP

(57) ABSTRACT

The invention described herein relates to the discovery that renalase, and fragments thereof, are useful for the treatment or prevention of cardiac and renal diseases or disorders. Thus, the invention relates to compositions comprising renalase, or fragments thereof, and methods for treating and preventing cardiac and renal disease or disorders.

4 Claims, 31 Drawing Sheets

Specification includes a Sequence Listing.

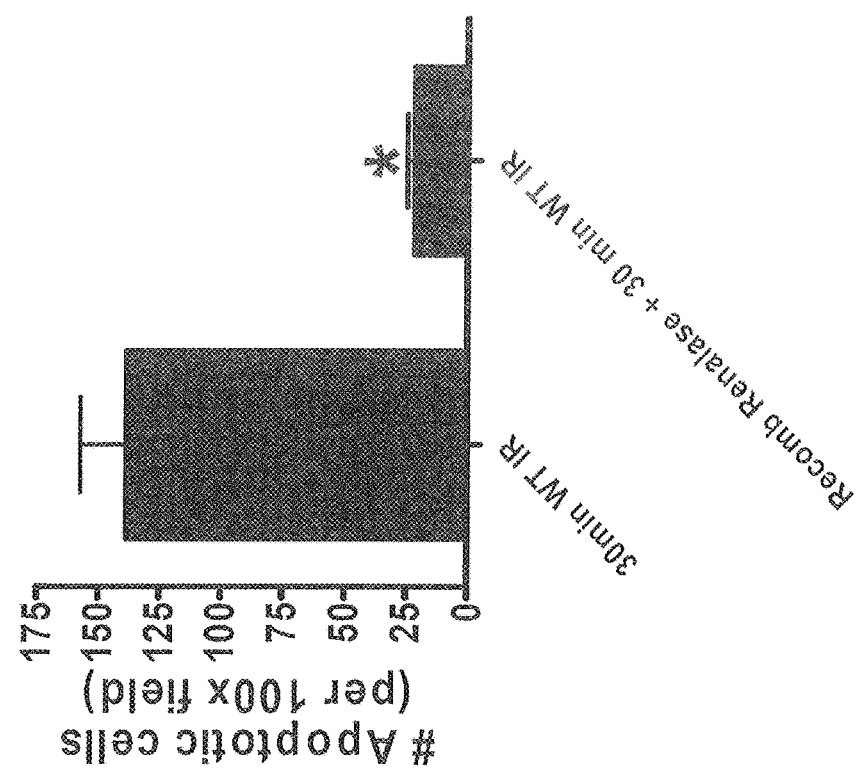

| | | |
|---|---|---|
| RP 224 | C-VSIDNKKRNI | (SEQ ID NO: 2) |
| RP 220 | CIRFVSIDNKKRNIESSEIG | (SEQ ID NO: 3) |
| RP H220 | HHHHHHCIRFVSIDNKKRNIESSEIG | (SEQ ID NO: 4) |
| RP A220 | IRFVSIDNAAANIESSEIG | (SEQ ID NO: 5) |
| RP 220 Scrambled | CSKRIFKVISSIEDNNERG | (SEQ ID NO: 6) |
| RP 128 | FRHRVTQINLRDDKWEVSKQ | (SEQ ID NO: 7) |
| RP 19 | LLRRQTSGPLYLAVWDKAED | (SEQ ID NO: 8) |

Figure 13

SEQUENCE LISTING

<160> NUMBER OF SEQ ID NOS: 22

<210> SEQ ID NO 1
<211> LENGTH: 20
<212> TYPE: PRT
<213> ORGANISM: Homo sapiens

```
<400> SEQUENCE: 1

Glu Ala Gly Thr Lys Ile Asp Val Pro Trp Ala Gly Gln Tyr Ile Thr
1               5                   10                  15

Ser Asn Pro Cys
            20

<210> SEQ ID NO 2
<211> LENGTH: 11
<212> TYPE: PRT
<213> ORGANISM: Homo sapiens

<400> SEQUENCE: 2

Cys Val Ser Ile Asp Asn Lys Lys Arg Asn Ile
1               5                   10

<210> SEQ ID NO 3
<211> LENGTH: 20
<212> TYPE: PRT
<213> ORGANISM: Homo sapiens

<400> SEQUENCE: 3

Cys Ile Arg Phe Val Ser Ile Asp Asn Lys Lys Arg Asn Ile Glu Ser
1               5                   10                  15

Ser Glu Ile Gly
            20

<210> SEQ ID NO 4
<211> LENGTH: 26
<212> TYPE: PRT
<213> ORGANISM: Homo sapiens

<400> SEQUENCE: 4

His His His His His His Cys Ile Arg Phe Val Ser Ile Asp Asn Lys
1               5                   10                  15

Lys Arg Asn Ile Glu Ser Ser Glu Ile Gly
            20                  25

<210> SEQ ID NO 5
<211> LENGTH: 19
<212> TYPE: PRT
<213> ORGANISM: Homo sapiens

<400> SEQUENCE: 5

Ile Arg Phe Val Ser Ile Asp Asn Ala Ala Asn Ile Glu Ser Ser
1               5                   10                  15

Glu Ile Gly

<210> SEQ ID NO 6
<211> LENGTH: 19
<212> TYPE: PRT
<213> ORGANISM: Homo sapiens

<400> SEQUENCE: 6

Cys Ser Lys Arg Ile Phe Lys Val Ile Ser Ser Ile Glu Asp Asn Asn
1               5                   10                  15

Glu Arg Gly

<210> SEQ ID NO 7
<211> LENGTH: 20
<212> TYPE: PRT
<213> ORGANISM: Homo sapiens
```

-continued

```
<400> SEQUENCE: 7

Phe Arg His Arg Val Thr Gln Ile Asn Leu Arg Asp Asp Lys Trp Glu
1               5                   10                  15

Val Ser Lys Gln
            20

<210> SEQ ID NO 8
<211> LENGTH: 20
<212> TYPE: PRT
<213> ORGANISM: Homo sapiens

<400> SEQUENCE: 8

Leu Leu Arg Arg Gln Thr Ser Gly Pro Leu Tyr Leu Ala Val Trp Asp
1               5                   10                  15

Lys Ala Glu Asp
            20

<210> SEQ ID NO 9
<211> LENGTH: 342
<212> TYPE: PRT
<213> ORGANISM: Homo sapiens

<400> SEQUENCE: 9

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
                20                  25                  30

Trp Asp Lys Ala Glu Asp Ser Gly Gly Arg Met Thr Thr Ala Cys Ser
            35                  40                  45

Pro His Asn Pro Gln Cys Thr Ala Asp Leu Gly Ala Gln Tyr Ile Thr
        50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255
```

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
        275                 280                 285

Arg His Ser Gln Val Thr Asn Ala Ala Ala Asn Cys Pro Gly Gln Met
    290                 295                 300

Thr Leu His His Lys Pro Phe Leu Ala Cys Gly Gly Asp Gly Phe Thr
305                 310                 315                 320

Gln Ser Asn Phe Asp Gly Cys Ile Thr Ser Ala Leu Cys Val Leu Glu
                325                 330                 335

Ala Leu Lys Asn Tyr Ile
            340

<210> SEQ ID NO 10
<211> LENGTH: 315
<212> TYPE: PRT
<213> ORGANISM: Homo sapiens

<400> SEQUENCE: 10

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Glu Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
        275                 280                 285

-continued

```
Arg His Ser Gln Val Pro Ser Ala Gly Val Ile Leu Gly Cys Ala Lys
            290                 295                 300
Ser Pro Trp Met Met Ala Ile Gly Phe Pro Ile
305                 310                 315

<210> SEQ ID NO 11
<211> LENGTH: 25
<212> TYPE: DNA
<213> ORGANISM: Homo sapiens

<400> SEQUENCE: 11
tactgaactt cggggtgatt ggtcc                                          25

<210> SEQ ID NO 12
<211> LENGTH: 24
<212> TYPE: DNA
<213> ORGANISM: Homo sapiens

<400> SEQUENCE: 12
cagccttgtc ccttgaagag aacc                                           24

<210> SEQ ID NO 13
<211> LENGTH: 19
<212> TYPE: DNA
<213> ORGANISM: Homo sapiens

<400> SEQUENCE: 13
tgtttcctgc ctctgaagc                                                 19

<210> SEQ ID NO 14
<211> LENGTH: 19
<212> TYPE: DNA
<213> ORGANISM: Homo sapiens

<400> SEQUENCE: 14
tgtttcctgc ctctgaagc                                                 19

<210> SEQ ID NO 15
<211> LENGTH: 20
<212> TYPE: DNA
<213> ORGANISM: Homo sapiens

<400> SEQUENCE: 15
acctgctgct actcattcac                                                20

<210> SEQ ID NO 16
<211> LENGTH: 20
<212> TYPE: DNA
<213> ORGANISM: Homo sapiens

<400> SEQUENCE: 16
ttgaggtggt tgtggaaaag                                                20

<210> SEQ ID NO 17
<211> LENGTH: 21
<212> TYPE: DNA
<213> ORGANISM: Homo sapiens

<400> SEQUENCE: 17
ccaagggttg acttcaagaa c                                              21
```

```
<210> SEQ ID NO 18
<211> LENGTH: 20
<212> TYPE: DNA
<213> ORGANISM: Homo sapiens

<400> SEQUENCE: 18
agcgaggcac atcaggtacg                                           20

<210> SEQ ID NO 19
<211> LENGTH: 20
<212> TYPE: DNA
<213> ORGANISM: Homo sapiens

<400> SEQUENCE: 19
tgaccttgtc atcctcacca                                           20

<210> SEQ ID NO 20
<211> LENGTH: 20
<212> TYPE: DNA
<213> ORGANISM: Homo sapiens

<400> SEQUENCE: 20
aactccaaat gggacagtgg                                           20

<210> SEQ ID NO 21
<211> LENGTH: 20
<212> TYPE: DNA
<213> ORGANISM: Homo sapiens

<400> SEQUENCE: 21
accacagtcc atgccatcac                                           20

<210> SEQ ID NO 22
<211> LENGTH: 21
<212> TYPE: DNA
<213> ORGANISM: Homo sapiens

<400> SEQUENCE: 22
caccaccctg ttgctgtagc c                                         21
```

COMPOSITIONS AND METHODS FOR DETECTING, TREATING AND PREVENTING DISEASES AND DISORDERS

CROSS-REFERENCE TO RELATED APPLICATIONS

The present application is a continuation of U.S. patent application Ser. No. 14/414,734, filed Jan. 14, 2015, which is the U.S. national phase application filed under 35 U.S.C. § 371 claiming benefit to International Patent Application No. PCT/US2013/50660, filed on Jul. 16, 2013, which claims priority to U.S. Provisional Patent Application No. 61/671,826, filed Jul. 16, 2012, U.S. Provisional Application No. 61/750,916, filed Jan. 10, 2013, and U.S. Provisional Application No. 61/813,778, filed Apr. 19, 2013, all of which applications are hereby incorporated herein by reference in their entirety.

STATEMENT REGARDING FEDERALLY SPONSORED RESEARCH OR DEVELOPMENT

This invention was made with government support under Grant Nos. RC1DK086465, RC1DK086402, RO1DK065172, and RO1DK081037 awarded by the National Institute of Health (NIH). The government has certain rights in the invention.

BACKGROUND OF THE INVENTION

Ischemic acute kidney injury (AKI) is a devastating clinical complication resulting in renal tubular death and systemic inflammation. Patients with kidney dysfunction have elevated plasma catecholamine levels. In addition to causing hypertension, catecholamines produce an inflammatory response in sepsis and multi-organ dysfunction.

Renalase is a 38 kDa flavin adenine dinucleotide (FAD)-dependent amine oxidase synthesized and secreted by the renal proximal tubules (Xu et al., 2005, J Clin Invest 115: 1275-1280). Renalase degrades circulating catecholamines and regulates systemic blood pressure in rodents and humans (Desir, 2012, Pediatr Nephrol 27: 719-725). Plasma catecholamines and systemic blood pressure are elevated in patients with chronic kidney dysfunction or end stage renal insufficiency (Schlaich, 2009, J Am Soc Nephrol 20: 933-939). Recent studies suggest that renalase deficiency in patients with chronic renal insufficiency leads to increased plasma catecholamine levels and systemic blood pressure (Desir, 2012, Pediatr Nephrol 27: 719-725; Desir, 2009, Kidney Int 76: 366-370; Desir, 2011, Curr Opin Nephrol Hypertens 20: 31-36; Li et al., 2008, Circulation 117: 1277-1282).

In addition to regulating blood pressure, renalase may protect against inflammatory tissue injury by metabolizing catecholamines. Catecholamines via activation of leukocyte alpha adrenergic receptors directly cause inflammation in sepsis and multi-organ dysfunction (Grisanti et al., 2011, J Pharmacol Exp Ther 338: 648-657; Miksa et al., 2009, PLoS One 4: e5504). Indeed, patients with chronic renal insufficiency show increased markers of inflammation that contribute directly to increased morbidity and mortality (Kaysen and Eiserich, 2003, Semin Dial 16: 438-446). In mice, renalase deficiency resulted in exacerbated cardiac IR injury and exogenous renalase administration reduced myocardial necrosis (Wu et al., 2011, Kidney Int 79: 853-860).

Ischemic acute kidney injury is a major problem for patients subjected to major surgical procedures involving the kidney, liver, heart or aorta (Chertow et al., 2005, J Am Soc Nephrol 16: 3365-3370). Renal ischemia reperfusion (IR) injury is a frequent cause of clinical AKI with the incidence of AKI exceeding 50% after major cardiac, hepatobiliary or aortic surgery (Bove et al., 2004, J Cardiothorac Vasc Anesth 18: 442-445; Elapavaluru and Kellum, 2007, Acta Clin Belg Suppl 326-331). Furthermore, ischemic AKI is frequently complicated by multi-organ dysfunction, systemic inflammation, sepsis and death (Jones and Lee, 2008, Best Pract Res Clin Anaesthesiol 22: 193-208). Unfortunately, there are no proven therapies to prevent or treat AKI in the perioperative setting (Jo et al., 2007, Clin J Am Soc Nephrol 2: 356-365).

Thus, there is a need in the art for compositions and methods for the treatment and prevention of renal injury, such as AKI. The present invention addresses this unmet need in the art.

SUMMARY OF THE INVENTION

The present invention relates to renalase, and fragments thereof, which are useful for the treatment or prevention of diseases and disorders, such as cardiac and renal diseases or disorders. Thus, the invention relates to compositions comprising renalase, or fragments thereof, as wells as to methods for treating and preventing diseases and disorders. In one embodiment, the invention is a method of treating a renal disease or disorder in a subject in need thereof, including the step of administering to the subject a therapeutically effective amount of a composition comprising at least one agent, wherein the at least one agent is at least one selected from the group consisting of a renalase polypeptide, a renalase polypeptide fragment, and an activator of renalase. In some embodiments, the renalase polypeptide is a recombinant renalase polypeptide. In one embodiment, the renalase polypeptide comprises the amino acid sequence of SEQ ID NO: 9. In another embodiment, the renalase polypeptide comprises the amino acid sequence of SEQ ID NO: 10. In one embodiment, the renalase polypeptide fragment comprises the amino acid sequence of SEQ ID NO: 2. In another embodiment, the renalase polypeptide fragment comprises the amino acid sequence of SEQ ID NO: 3. In another embodiment, the renalase polypeptide fragment comprises the amino acid sequence of SEQ ID NO: 4. In some embodiments, the at least one agent is administered one time. In other embodiments, the at least one agent is administered repeatedly. In various embodiments, the at least one agent is administered locally, regionally or systemically. In various embodiments, the activator of renalase is an activator of renalase expression, an activator of renalase activity, or a combination thereof. In various embodiments, the renal disease or disorder is at least one selected from the group consisting of renal ischemic injury, renal reperfusion injury, renal ischemic-reperfusion injury, toxic renal injury, renal tubular necrosis, renal tubular inflammation, renal tubular apoptosis, and hypertension. In various embodiments, the activator of renalase is at least one selected from the group consisting of a chemical compound, a protein, a peptide, a peptidomemetic, and a small molecule chemical compound. In some embodiments, the subject is human.

In one embodiment, the invention is a composition comprising a renalase polypeptide fragment comprising the amino acid sequence of SEQ ID NO: 2. In another embodiment, the invention is a composition comprising a renalase polypeptide fragment comprising the amino acid sequence of SEQ ID NO: 3. In another embodiment, the invention is a renalase polypeptide fragment comprising the amino acid sequence of SEQ ID NO: 4.

In another embodiment, the invention is a method of diagnosing a renal disease or disorder in a subject in need thereof, including the steps of determining the level of renalase in a biological sample of the subject, comparing the level of renalase in the biological sample of the subject with a comparator control, and diagnosing the subject with a renal disease or disorder when the level of renalase in the biological sample of subject is reduced when compared with the level of renalase of the comparator control. In some embodiments, the method further comprises the step of treating the subject that was diagnosed as having a renal disease or disorder. In some embodiments, the level of renalase in the biological sample is determined by measuring the level of renalase mRNA in the biological sample. In other embodiments, the level of renalase in the biological sample is determined by measuring the level of renalase polypeptide in the biological sample. In some embodiments, the level of renalase in the biological sample is determined by measuring an enzymatic activity of renalase polypeptide in the biological sample. In various embodiments, the comparator control is at least one selected from the group consisting of: a positive control, a negative control, a historical control, a historical norm, or the level of a reference molecule in the biological sample. In various embodiments, the renal disease or disorder is at least one selected from the group consisting of renal ischemic injury, renal reperfusion injury, renal ischemic-reperfusion injury, toxic renal injury, renal tubular necrosis, renal tubular inflammation, renal tubular apoptosis, and hypertension. In some embodiments, the subject is human.

In one embodiment, the invention is a method of treating a cardiac disease or disorder in a subject in need thereof, including the step of administering to the subject a therapeutically effective amount of a composition comprising at least one agent, wherein the at least one agent is at least one selected from the group consisting of a renalase polypeptide, a renalase polypeptide fragment, and an activator of renalase. In some embodiments, the renalase polypeptide is a recombinant renalase polypeptide. In one embodiment, the renalase polypeptide comprises the amino acid sequence of SEQ ID NO: 9. In another embodiment, the renalase polypeptide comprises the amino acid sequence of SEQ ID NO: 10. In one embodiment, the renalase polypeptide fragment comprises the amino acid sequence of SEQ ID NO: 2. In another embodiment, the renalase polypeptide fragment comprises the amino acid sequence of SEQ ID NO: 3. In another embodiment, the renalase polypeptide fragment comprises the amino acid sequence of SEQ ID NO: 4. In some embodiments, the at least one agent is administered one time. In other embodiments, the at least one agent is administered repeatedly. In various embodiments, the at least one agent is administered locally, regionally or systemically. In various embodiments, the activator of renalase is an activator of renalase expression, an activator of renalase activity, or a combination thereof. In various embodiments, the cardiac disease or disorder is at least one selected from the group consisting of myocardial necrosis, congestive heart failure, cardiac ischemic injury, cardiac reperfusion injury, cardiac ischemic-reperfusion injury and hypertension. In various embodiments, the activator of renalase is at least one selected from the group consisting of a chemical compound, a protein, a peptide, a peptidomemetic, and a small molecule chemical compound. In some embodiments, the subject is human.

In another embodiment, the invention is a method of diagnosing a cardiac disease or disorder in a subject in need thereof, including the steps of determining the level of renalase in a biological sample of the subject, comparing the level of renalase in the biological sample of the subject with a comparator control, and diagnosing the subject with a cardiac disease or disorder when the level of renalase in the biological sample of subject is reduced when compared with the level of renalase of the comparator control. In some embodiments, the method further comprises the step of treating the subject that was diagnosed as having a cardiac disease or disorder. In some embodiments, the level of renalase in the biological sample is determined by measuring the level of renalase mRNA in the biological sample. In other embodiments, the level of renalase in the biological sample is determined by measuring the level of renalase polypeptide in the biological sample. In some embodiments, the level of renalase in the biological sample is determined by measuring an enzymatic activity of renalase polypeptide in the biological sample. In various embodiments, the comparator control is at least one selected from the group consisting of: a positive control, a negative control, a historical control, a historical norm, or the level of a reference molecule in the biological sample. In various embodiments, the cardiac disease or disorder is at least one selected from the group consisting of myocardial necrosis, congestive heart failure, cardiac ischemic injury, cardiac reperfusion injury, cardiac ischemic-reperfusion injury and hypertension. In some embodiments, the subject is human.

In one embodiment, the invention is a method of treating cancer in a subject in need thereof, including the step of administering to the subject a therapeutically effective amount of a composition comprising at least one agent, wherein the at least one agent is a renalase inhibitor. In some embodiments, the at least one agent is administered one time. In other embodiments, the at least one agent is administered repeatedly. In various embodiments, the at least one agent is administered locally, regionally or systemically. In some embodiments, the renalase inhibitor is an inhibitor of renalase expression, an inhibitor of renalase activity, or a combination thereof. In various embodiments, the renalase inhibitor is at least one selected from the group consisting of an antibody, a chemical compound, a protein, a peptide, a peptidomemetic, and a small molecule chemical compound. In one embodiment, the renalase inhibitor is an antibody that specifically binds to renalase. In various embodiments, the antibody is at least one selected from the group consisting of a polyclonal antibody, a monoclonal antibody, an intracellular antibody, an antibody fragment, a single chain antibody (scFv), a heavy chain antibody, a synthetic antibody, a chimeric antibody, and a humanized antibody. In some embodiments, the subject is human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A and 1B, is a set of images showing that renalase co-localizes with proximal tubules. Pig kidney sections were co-stained with a renalase antibody and either with a megalin antibody (a proximal tubule marker—FIG. 1A) or with an E-cadherin (a distal tubule marker—FIG. 1B). It was observed that renalase is exclusively expressed in proximal tubules. Representative of 3 experiments. Images were magnified 100× for megalin co-staining and 40× for E-cadherin co-staining.

FIG. 3, comprising FIG. 3A: representative immunoblot (top) and band intensity quantifications (bottom) for plasma renalase protein in sham-operated mice and mice subjected to 30 min. renal ischemia and 5 hr. or 24 hr. reperfusion (N=4-5 per group). Note significant reductions in plasma renalase after renal IR. FIG. 3B: Representative images (top) and GAPDH-normalized band intensity quantifications (bottom) for kidney renalase mRNA in renalase WT or renalase KO mice. Mice were subjected to sham-operation or to 30 min. renal ischemia and 24 hr. reperfusion (N=4 per group). GAPDH mRNA served as internal loading controls. Consistent with the significant decreases in plasma renalase, kidney renalase mRNA expression was significantly attenuated 24 hr. after renal IR. Data are presented as means±SEM. *$P<0.05$ vs. sham group.

FIG. 4, comprising FIG. 4A: Renalase wild type (WT) or renalase deficient (KO) mice were subjected to 20 min. (moderate ischemia) or 30 min. (severe ischemia) renal ischemia and 24 hr. reperfusion (N=4-6 per group). Renalase deficiency exacerbated renal IR injury in mice. FIG. 4B: Renalase WT mice were subjected to sham-surgery or to 30 min. renal IR. For mice subjected to renal IR, human recombinant renalase or vehicle (saline) was injected 10 min. prior to renal ischemia. Recombinant human renalase produced significant renal protection in renalase WT mice (N=4-6 per group). FIG. 4C: Pre- or post-ischemic human recombinant renalase rescues renal function after IR in mice (N=4-6 per group). Human recombinant given 30 min. after completion of renal ischemia protected against IR injury. FIG. 4D: Phentolamine (5 mg/kg, a selective alpha-adrenergic receptor antagonist) protected both renalase wild type (WT) and renalase deficient (KO) mice subjected to 30 min. renal ischemia and 24 hr. reperfusion (N=4). *$P<0.05$ vs. vehicle-treated mice subjected to sham-surgery. #$P<0.05$ vs. vehicle-treated WT mice subjected to renal IR. Error bars represent 1 SEM.

FIG. 5, comprising FIG. 5A: Representative photomicrographs for hematoxylin and eosin staining (magnification 200×) of kidney sections of renalase wild type (WT) or renalase deficient (KO) mice subjected to 20 min. or 30 min. renal ischemia and 24 hr. reperfusion. Some renalase WT mice were pretreated 1.5 mg/kg human recombinant renalase 10 min. before renal ischemia. Photographs are representative of 3-5 independent experiments. FIG. 5B: Summary of Jablonski scale renal injury scores (N=4, graded from hematoxylin and eosin staining, scale 0-4) for mice subjected to renal IR. It has been shown that renalase KO mice had worse renal tubular necrosis after IR and recombinant renalase provided significant renal tubular protection against necrosis in renalase WT mice. *$P<0.05$ vs. WT mice subjected to 20 min. renal IR. #$P<0.05$ vs. vehicle-treated WT mice subjected to 30 min. renal IR. Error bars represent 1 SEM.

FIG. 6, comprising FIGS. 6A and 6B, is an image and a graph showing that exogenous recombinant human renalase reduces renal tubular apoptosis in mice after IR. FIG. 6A: Representative photomicrographs for TUNEL staining (representing apoptotic nuclei, magnification 100×) of kidney sections of mice subjected to sham-operation or to 30 min. renal ischemia and 24 hr. reperfusion. Mice were pretreated with saline vehicle or with 1.5 mg/kg human recombinant renalase 10 min. before renal ischemia. Photographs are representative of 4 independent experiments. FIG. 6B: Quantifications of apoptotic cells per 100× field in the kidneys of mice after renal IR. *$P<0.05$ vs. vehicle-treated mice subjected to renal IR. Error bars represent 1 SEM. Recombinant renalase treatment significantly decreased renal tubular apoptosis in mice after renal IR injury.

FIG. 7, comprising FIGS. 7A and 7C: Representative photomicrographs for immunohistochemistry for neutrophil infiltration (magnification 200×) or macrophages (F4/80 staining, magnification 400×) of kidney sections of mice subjected to sham-operation or to 30 min. renal ischemia and 24 hr. reperfusion. Mice were pretreated with saline vehicle or with 1.5 mg/kg human recombinant renalase 10 min. before renal ischemia. Photographs are representative of 3-5 independent experiments. FIGS. 7B and 7D: Quantifications of infiltrated neutrophils (per 200× field) and macrophages (per 400× field) in the kidneys of mice after renal IR. *$P<0.05$ vs. sham-operated group. #$P<0.05$ vs. vehicle-treated mice subjected to renal IR. Error bars represent 1 SEM. Recombinant renalase treatment significantly reduced renal neutrophil as well as macrophage infiltration in mice after renal IR injury.

FIG. 8, comprising FIG. 8A: Representative gel images of RT-PCR of GAPDH, TNF-$\alpha$, ICAM-1, MCP-1 and MIP-2. FIG. 8B: Densitometric quantification of relative band intensities normalized to GAPDH of pro-inflammatory markers TNF-$\alpha$, ICAM-1, MCP-1 and MIP-2 from kidney of mice subjected to renal IR (N=4-5 per group). Renalase deficient mice had significantly increased expression of TNF-$\alpha$, MCP-1 and MIP-2 mRNAs examined compared to the renalase WT mice subjected to renal IR. *$P<0.05$ vs. Sham-operated mice. #$P<0.05$ vs. renalase WT mice subjected to renal IR. Error bars represent 1 SEM.

FIGS. 11A through 11D, is a set of images and graphs showing renalase protects HK-2 cells against cisplatin toxicity, inhibits apoptosis and upregulates Bcl-2 expression. FIG. 11A: HK-2 cells treated with cisplatin with and without renalase for 24 hrs, renalase expression measured by western blot; FIG. 11B: renalase improves cell survival as measured by WST-1; FIG. 11 C: HK-2 cells treated with cisplatin with and without renalase for 24 hrs, caspase measured by western blot, and quantified by densitometry (right panel); FIG. 11D: as in FIG. 11C, Bcl-2 measured by western.

FIGS. 12A through 12E, is a set of images and graphs showing renalase upregulates Bcl-2, activates PI3K/AKT, ERK, p38, and inhibits JNK. Western blot analysis; P- indicates phosphorylated, activated proteins; signals normalized to GAPDH loading control, then changes in protein phosphorylation (increase=activation, decrease=inhibition) from time 0 are calculated. FIG. 12A: HK-2 and HUVEC cells incubated with renalase for 24 hrs; FIG. 12B: Western blot of time course of AKT and MAPK signaling by renalase, HK-2 cells incubated with renalase for indicated time; changes over baseline in 4c-d are significant ($p<0.05$); FIG. 12C: Activation of AKT(T308), AKT(5473) and ERK; FIG. 12D: Inhibition of JNK; FIG. 12E: Marked and sustained (60 min) upregulation of p38 by renalase in the presence of cisplatin, western blot for time course, REN=renalase, CP=cisplatin.

FIG. 13 is a listing of renalase peptide amino acid sequences. Depicted are RP 224 (SEQ ID NO: 2), RP 220 (SEQ ID NO: 3), RP H220 (SEQ ID NO: 4), RP A220 (SEQ ID NO: 5), RP 220 Scrambled (SEQ ID NO: 6), RP 128 (SEQ ID NO: 7), and RP 19 (SEQ ID NO: 8).

FIGS. 14A-14C, depicts the results of experiments demonstrating the hemodynamic effect of renalase peptides. A single intravenous injection of RP-220 in anesthetized wild type mice; BP pressure is recorded continuously; RP-220 is given at time 0; each data point represents the average of systolic or diastolic BP values collected at the indicated time points in 6 animals; The Kruskal-Wallis test revealed statistical significance, and the Mann-Whitney test was used for pairwise comparisons; *: Indicates $P<0.05$ (FIG. 14A). As in 14A, except that RP-H220 is injected; no significant changes in blood pressure (FIG. 14B). Effect of a single intravenous injection of RP-220 (squares) and RP-H220 (diamonds) on heart rate in wild type mice (FIG. 14C). RP H220, RP A220, RP 224, RP 220 scrambled, RP 128 and RP 19 had no effect on BP.

FIGS. 17A-17D, depicts the results of experiments demonstrating that renalase deficiency aggravates cisplatin AKI. Plasma creatinine levels in WT and renalase KO mice 3 days post administration of cisplatin; n=6, *: $P<0.05$ (FIG. 17A). Representative photomicrographs for hematoxylin and eosin (H&E) staining of kidney sections of WT mice treated with cisplatin. (FIG. 17B, left panel). Representative photomicrograph of H&E staining of kidney from renalase KO mice treated with cisplatin (FIG. 17B, middle panel). Renal injury score, n=6, *: $P<0.05$ (FIG. 17B, right panel). Representative photomicrographs of TUNEL staining of kidney sections of WT mice treated with cisplatin; n=6 (FIG. 17C, left panel). Representative photomicrograph of TUNEL staining of kidney from renalase KO mice treated with cisplatin, n=6 (FIG. 17C, middle panel). Number of apoptotic nuclei per 40× field, n=6, *: $P<0.05$ (FIG. 17C, right panel). Representative photomicrographs of macrophage (F4/80) staining of kidney sections of WT mice treated with cisplatin; n=5 (FIG. 17D, left panel). Representative photomicrograph of macrophage (F4/80) staining of kidney from renalase KO mice treated with cisplatin, n=5 (FIG. 17D, middle panel). Number of macrophages per 100× field; n=5, *: $P<0.05$ (FIG. 17D, right panel).

FIGS. 18A-18D, depicts the results of experiments demonstrating that recombinant renalase protects HK-2 cells against oxidant and cisplatin mediated injury. HK-2 cell treated with 2 mM $H_2O_2$ with and without renalase for indicated time; LDH: lactate dehydrogenase; n=8, *: $P<0.05$ for Control vs. renalase; #: $P<0.05$ for control vs. $H_2O_2$(FIG. 18A). HK-2 cells treated with 20 μM cisplatin with and without renalase for 24 hrs (FIG. 18B). Cell survival measured by the WST-1 method; n=6, *: $P<0.05$ (FIG. 18B, left panel). Renalase expression measured by western blot; representative blot shown, n=3 (FIG. 18B, right panel). HK-2 cells treated with as in 18B (FIG. 18C); Caspase activation measured by western blot (FIG. 18C). Quantification by densitometry, n=3; *: $P<0.05$ (FIG. 18C, right panel). HK-2 cells treated as in 18B (FIG. 18D). Bcl-2 expression measured by western blot (FIG. 18D, left panel). Quantification by densitometry; n=3, *: $P<0.05$ (FIG. 18D, right panel).

FIGS. 19A-19F, depicts the results of experiments demonstrating that renalase's protective effect is independent of its enzymatic activity. Renalase isoforms Ren1-7; exons numbered from 1 to 10; RP-224: renalase peptide amino acid 224-233 of Ren1 or Ren2; RP-220; amino acids 220-239; RP-H220: histidine tagged RP-220; RP-Scr220: scrambled RP-220 (FIG. 19A). CCL-119 cells in culture treated with anti-renalase monoclonal antibody for 24 hrs; cell survival measured by the WST-1 method; n=3, *: $P<0.05$ (FIG. 19B). HK-2 cell treated with 2 mM $H_2O_2$ with and without renalase peptides for indicated time; LDH: lactate dehydrogenase; n=6, *: $P<0.05$ for Control vs. renalase peptide (FIG. 19C). HK-2 cells treated with 20 μM cisplatin with and without recombinant renalase and renalase peptides for 24 hrs, *: $P<0.05$, control vs. renalase peptide (FIG. 19D). Plasma creatinine levels from mice subjected to sham-surgery or to renal ischemia and reperfusion (IR); Renalase WT mice were subjected to sham-surgery or to 30 min renal IR. For mice subjected to renal IR, RP-H220 or vehicle (saline) was injected 10 min prior to renal ischemia. RP-H220 produced significant renal protection in renalase WT mice (N=4-6 per group). *: $P<0.05$ vs. vehicle-treated mice subjected to sham-surgery; #: $P<0.05$ vs. vehicle-treated WT mice subjected to renal IR (FIG. 19E). Renalase peptides do not oxidize NADH; recombinant Renalase or peptides in 25 mM Tris, pH 7.5, 5 mM NaCl, and 150 μM NADH, at 37° C.; *: $P<0.05$ (FIG. 19F).

FIGS. 20A-20C, depicts the results of experiments demonstrating that MAPK activation is critical for the protective effect of renalase peptides. MAPK signaling by renalase and renalase peptides. Western blot analysis; ERK: Extracellular signal-Regulated Kinase 1 and 2; JNK: c-Jun N-terminal Kinases; AKT: protein kinase B; p-indicates phosphorylated, activated proteins; representative blot, n=3 (FIG. 20A). Renalase activates AKT (FIG. 20B). Western blot analysis; P- indicates phosphorylated, activated proteins Representative blot, n=3 (FIG. 20B, left panel). Signals normalized to GAPDH loading control; n=3, change over baseline statistically significant (P<0.05) from 1-60 min for ERK, p38 and AKT (T308), and at 30 min only for AKT (S473) (FIG. 20B, right panel). ERK or AKT inhibition abrogates protective effect of RP-H220 (FIG. 20C). Plasma creatinine levels from mice subjected to sham-surgery or to renal ischemia and reperfusion (IR); Renalase WT mice were subjected to sham-surgery or to 30 min renal IR. For mice subjected to renal IR, RP-H220 or vehicle (saline) was injected 10 min prior to renal ischemia. Some animals were pretreated with either the ERK inhibitor PD98059 or the PI3K/AKT inhibitor wortmanin. (N=6-8 per group). *:P<0.05 vs. vehicle-treated mice subjected to sham-surgery; #: P<0.05 vs. vehicle-treated WT mice subjected to renal IR (FIG. 20C).

DETAILED DESCRIPTION

Figure 1:
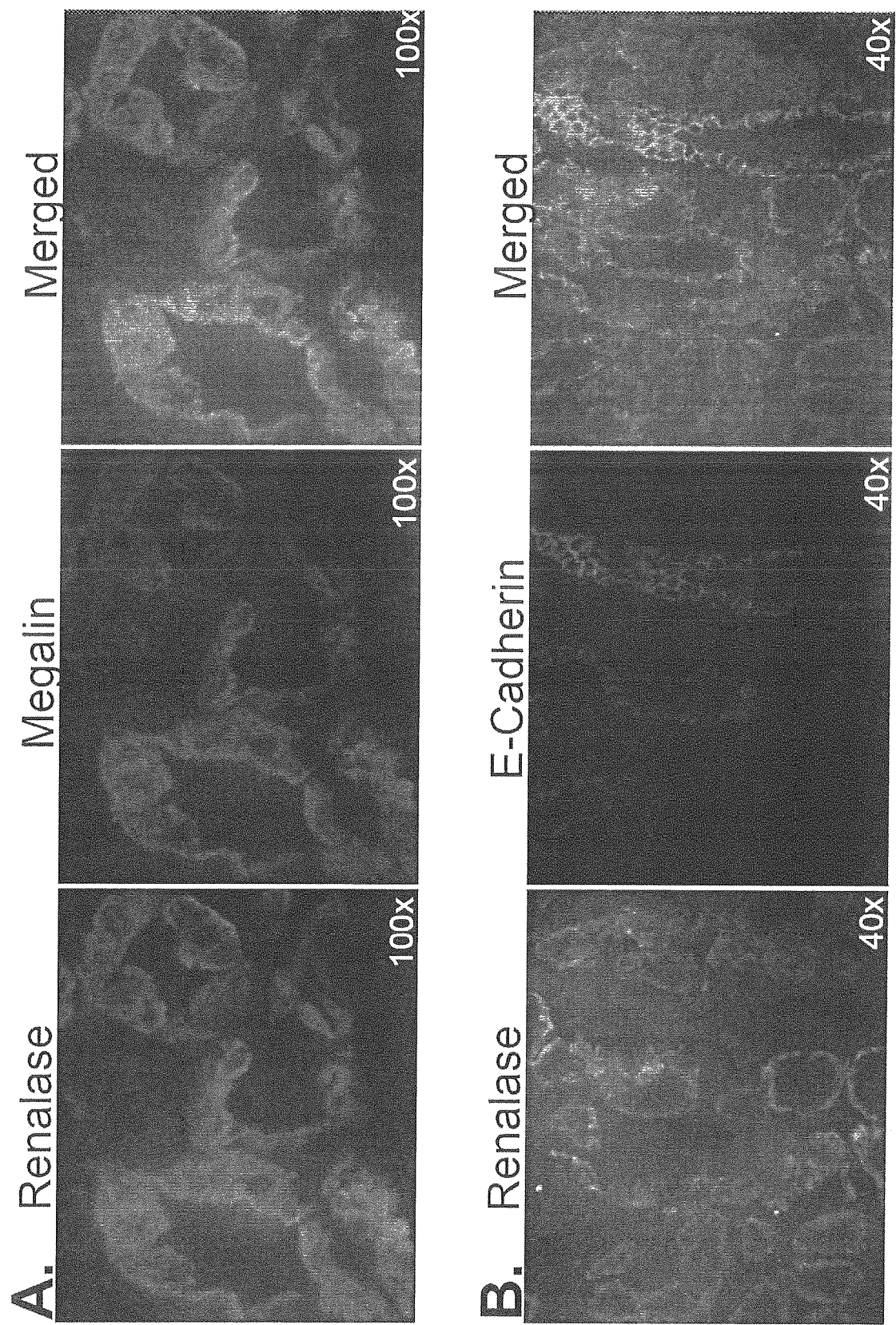
FIG. 1, comprising

The present invention relates to the discovery that renalase, and fragments thereof, are useful for the treatment or prevention of diseases or disorders, such as cardiac and renal diseases or disorders. Thus, the invention relates to compositions comprising renalase, or fragments thereof, and methods for treating and preventing diseases and disorders, including cardiac and renal disease or disorders. In some embodiments, the renal injury treated or prevented using the compositions and methods of the invention is AKI caused by ischemia/reperfusion (IR).

In one embodiment, the renalase of the invention is a polypeptide comprising the amino acid sequence of SEQ ID NO: 9. In another embodiment, the renalase of the invention is a polypeptide comprising the amino acid sequence of SEQ ID NO: 10. In some embodiments, the renalase of the invention is a renalase fragment comprising at least a portion of the amino acid sequence of SEQ ID NO: 9 or SEQ ID NO: 10. In some embodiments, the renalase fragment is a peptide that retains its AKI protective activity, but does not exhibit detectable NADH oxidase activity. In some embodiments, the renalase fragment is a peptide that retains its protective activity, but does not exhibit detectable amine oxidase activity. In a particular embodiment, the renalase fragment is a peptide comprising the amino acid sequence of SEQ ID NO: 2. In another particular embodiment, the renalase fragment is a peptide comprising the amino acid sequence of SEQ ID NO: 3. In another particular embodiment, the renalase fragment is a peptide comprising the amino acid sequence of SEQ ID NO: 4.

The compositions and methods of the invention comprise recombinant renalase, or fragments thereof. The compositions and methods of the invention include compositions and methods for treating or preventing myocardial necrosis, heart failure, congestive heart failure, cardiac ischemic injury, cardiac reperfusion injury, cardiac ischemic-reperfusion injury, toxic cardiac injury, renal ischemic injury, renal reperfusion injury, renal ischemic-reperfusion injury, toxic renal injury, renal tubular necrosis, renal tubular inflammation, renal tubular apoptosis, ischemic brain injury, reperfusion brain injury, ischemic-reperfusion brain injury, toxic brain injury, ischemic liver injury, reperfusion liver injury, ischemic-reperfusion liver injury, toxic liver injury, and hypertension. In some embodiments, the compositions and methods of the invention are useful for controlling or maintaining blood pressure. In some embodiments, the compositions and methods of the invention are useful for treating or preventing sympathetic nervous system diseases and disorders, such as, by way of a non-limiting examples, anxiety, post-traumatic stress disorder (PTSD) and attention deficit hyperactivity disorder (ADHD).

In another embodiment, the invention is a method of diagnosing a renal disease or disorder of a subject by assessing the level of renalase in a biological sample of the subject. In one embodiment, a change (i.e., increase or decrease) in the level of renalase compared with a comparator is a marker for the diagnosis of a renal disease or disorder, or a cardiac disease or disorder, as well as for monitoring the treatment of a renal or cardiac disease or disorder.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" or "treat" a disease means reducing the frequency or severity of at least one sign or symptom of a disease or disorder.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and a humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. K and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "applicator," as the term is used herein, is meant any device including, but not limited to, a hypodermic syringe, a pipette, an iontophoresis device, a patch, and the like, for administering the compositions of the invention to a subject.

As used herein, the term "marker" or "biomarker" is meant to include a parameter which is useful according to this invention for determining, for example, the presence and/or severity of a cardiac or renal disease or disorder. By way of a non-limiting example, a "marker" or "biomarker" is the level and/or activity of renalase.

The level of a marker or biomarker "significantly" differs from the level of the marker or biomarker in a reference sample if the level of the marker in a sample from the patient differs from the level in a sample from the reference subject by an amount greater than the standard error of the assay employed to assess the marker, and preferably at least 10%, and more preferably 25%, 50%, 75%, or 100%.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein, polypeptide or peptide, refers to a subsequence of a larger protein or peptide. A "fragment" of a protein, polypeptide, or peptide can be at least about 5 amino acids in length; for example, at least about 10 amino acids in length; at least about 20 amino acids in length; at least about 50 amino acids in length; at least about 100 amino acids in length; at least about 200 amino acids in length; or at least about 300 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Instructional material," as that term is used herein, includes a publication, a recording, a diagram, or any other medium of expression which can be used to communicate the usefulness of the nucleic acid, peptide, polypeptide, and/or compound of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the invention or be shipped together with a container that contains the nucleic acid, polypeptide, and/or compound. Alternatively, the instructional material may be shipped separately from the container with the intention that the recipient uses the instructional material and the compound cooperatively.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject. The term encompasses activating, inhibiting and/or otherwise affecting a native signal or response thereby mediating a beneficial therapeutic response in a subject, preferably, a human.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "polymerase chain reaction" ("PCR") refers to the method of K. B. Mullis (U.S. Pat. Nos. 4,683,195, 4,683,202, and 4,965,188, hereby incorporated by reference) for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types.

"Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

To "prevent" a disease or disorder as the term is used herein, means to reduce the severity or frequency of at least one sign or symptom of a disease or disorder being experienced by a subject.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, "substantially purified" refers to being essentially free of other components. For example, a substantially purified polypeptide is a polypeptide which has been separated from other components with which it is normally associated in its naturally occurring state.

As used herein, the terms "therapy" or "therapeutic regimen" refer to those activities taken to prevent, alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more compounds or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease or disorder as the term is used herein, means to reduce the frequency or severity of at least one sign or symptom of a disease or disorder experienced by a subject.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In some embodiments, the compositions and methods of the invention comprise renalase, or a fragment thereof, for use in the treatment or prevention of a cardiac or renal disease or disorder. In some embodiments, the renalase of the invention is a polypeptide comprising the amino acid sequence of SEQ ID NO: 9 or SEQ ID NO: 10. In some embodiments, the renalase of the invention is a renalase fragment comprising at least a portion of the amino acid sequence of SEQ ID NO: 9 or SEQ ID NO: 10. In some embodiments, the renalase fragment is a peptide that retains its protective activity, but does not exhibit detectable NADH oxidase activity. In some embodiments, the renalase fragment is a peptide that retains its protective activity, but does not exhibit detectable amine oxidase activity. In a particular embodiment, the renalase fragment is a peptide comprising the amino acid sequence of SEQ ID NO: 2. In another particular embodiment, the renalase fragment is a peptide comprising the amino acid sequence of SEQ ID NO: 3. In another particular embodiment, the renalase fragment is a peptide comprising the amino acid sequence of SEQ ID NO: 4. In another particular embodiment, the renalase fragment is a peptide consisting of the amino acid sequence of SEQ ID NO: 2. In another particular embodiment, the renalase fragment is a peptide consisting of the amino acid sequence of SEQ ID NO: 3. In another particular embodiment, the renalase fragment is a peptide consisting of the amino acid sequence of SEQ ID NO: 4.

The compositions and methods of the invention comprise recombinant renalase, or fragments thereof. The compositions and methods of the invention include compositions and methods for treating or preventing disorders and diseases where an increased activity or level of renalase is desirable. In various embodiments, the disorders and diseases where an increased activity or level of renalase is desirable which can be treated or prevented with the compositions and methods of the invention include AKI, myocardial necrosis, heart failure, congestive heart failure, cardiac ischemic injury, cardiac reperfusion injury, cardiac ischemic-reperfusion injury, toxic cardiac injury, renal ischemic injury, renal reperfusion injury, renal ischemic-reperfusion injury, toxic renal injury, renal tubular necrosis, renal tubular inflammation, renal tubular apoptosis, ischemic brain injury, reperfusion brain injury, ischemic-reperfusion brain injury, toxic brain injury, ischemic liver injury, reperfusion liver injury, ischemic-reperfusion liver injury, toxic liver injury, and hypertension. In some embodiments, the compositions and methods of the invention are useful for controlling or maintaining blood pressure. In some embodiments, the compositions and methods of the invention are useful for treating or preventing sympathetic nervous system diseases and disorders, such as, by way of a non-limiting examples, anxiety, post-traumatic stress disorder (PTSD) and attention deficit hyperactivity disorder (ADHD).

In another embodiment, the invention is a method of diagnosing a renal disease or disorder of a subject by assessing the level of renalase in a biological sample of the subject. In one embodiment, a change (i.e., increase or decrease) in the level of renalase compared with a comparator is a marker for the diagnosis of a renal disease or disorder, or a cardiac disease or disorder, as well as for monitoring the treatment of a renal or cardiac disease or disorder.

Compositions and Methods of Treatment and Prevention

In various embodiments, the present invention includes renalase activator compositions and methods of increasing the level or activity of renalase, or a fragment thereof, in a subject, a tissue, or an organ in need thereof. In various embodiments, the renalase activator compositions and methods of treatment of the invention increase the amount of renalase polypeptide, the amount of renalase mRNA, the amount of renalase enzymatic activity, the amount of renalase substrate binding activity, or a combination thereof. In various embodiments, the diseases and disorders where in increase in renalase may improve therapeutic outcome include, but are not limited to, AKI, myocardial necrosis, heart failure, congestive heart failure, cardiac ischemic injury, cardiac reperfusion injury, cardiac ischemic-reperfusion injury, toxic cardiac injury, renal ischemic injury, renal reperfusion injury, renal ischemic-reperfusion injury, toxic renal injury, renal tubular necrosis, renal tubular inflammation, renal tubular apoptosis, ischemic brain injury, reperfusion brain injury, ischemic-reperfusion brain injury, toxic brain injury, ischemic liver injury, reperfusion liver injury, ischemic-reperfusion liver injury, toxic liver injury, and hypertension. In some embodiments, the compositions and methods of the invention are useful for controlling or maintaining blood pressure. In some embodiments, the compositions and methods of the invention are useful for treating or preventing sympathetic nervous system diseases and disorders, such as, by way of a non-limiting examples, anxiety, post-traumatic stress disorder (PTSD) and attention deficit hyperactivity disorder (ADHD).

It will be understood by one skilled in the art, based upon the disclosure provided herein, that an increase in the level of renalase encompasses the increase in renalase expression, including transcription, translation, or both. The skilled artisan will also appreciate, once armed with the teachings of the present invention, that an increase in the level of renalase includes an increase in renalase activity (e.g., enzymatic activity, substrate binding activity, etc.). Thus, increasing the level or activity of renalase includes, but is not limited to, increasing the amount of renalase polypeptide, and increasing transcription, translation, or both, of a nucleic acid encoding renalase; and it also includes increasing any activity of a renalase polypeptide as well. The renalase activator compositions and methods of the invention can selectively activate renalase, or can activate both renalase and another molecule.

Thus, the present invention relates to the prevention and treatment of a disease or disorder by administration of a therapeutically effective amount of a renalase polypeptide, a recombinant renalase polypeptide, an active renalase polypeptide fragment (i.e., renalase peptide), or an activator of renalase expression or activity, to a subject in need thereof, for the treatment or prevention of a disease or disorder, or its associated signs, symptoms or pathologies. In some embodiments, the renalase polypeptide comprises the amino acid of SEQ ID NO: 9 or SEQ ID NO: 10. In some embodiments, the renalase of the invention is a renalase polypeptide fragment comprising at least a portion of the amino acid sequence of SEQ ID NO: 9 or SEQ ID NO: 10. In some embodiments, the renalase polypeptide fragment is a peptide that retains its protective activity, but does not exhibit detectable NADH oxidase activity. In some embodiments, the renalase polypeptide fragment is a peptide that retains its protective activity, but does not exhibit detectable amine oxidase activity. In a particular embodiment, the renalase polypeptide fragment is a peptide comprising the amino acid sequence of SEQ ID NO: 2. In another particular embodiment, the renalase polypeptide fragment is a peptide comprising the amino acid sequence of SEQ ID NO: 3. In another particular embodiment, the renalase polypeptide fragment is a peptide comprising the amino acid sequence of SEQ ID NO: 4. In another particular embodiment, the renalase polypeptide fragment is a peptide consisting of the amino acid sequence of SEQ ID NO: 2. In another particular embodiment, the renalase polypeptide fragment is a peptide consisting of the amino acid sequence of SEQ ID NO: 3. In another particular embodiment, the renalase polypeptide fragment is a peptide consisting of the amino acid sequence of SEQ ID NO: 4.

It is understood by one skilled in the art, that an increase in the level of renalase encompasses an increase in the amount of renalase, or fragment thereof (e.g., by administration of renalase or a fragment thereof, by increasing renalase protein expression, etc.). Additionally, the skilled artisan would appreciate, that an increase in the level of renalase includes an increase in renalase activity. Thus, increasing the level or activity of renalase includes, but is not limited to, the administration of renalase or a fragment thereof, as well as increasing transcription, translation, or both, of a nucleic acid encoding renalase; and it also includes increasing any activity of renalase as well.

The increased level or activity of renalase can be assessed using a wide variety of methods, including those disclosed herein, as well as methods well-known in the art or to be developed in the future. That is, the routineer would appreciate, based upon the disclosure provided herein, that increasing the level or activity of renalase can be readily assessed using methods that assess the level of a nucleic acid encoding renalase (e.g., mRNA), the level of renalase polypeptide, and/or the level of renalase activity in a biological sample obtained from a subject.

One skilled in the art, based upon the disclosure provided herein, would understand that the invention is useful in subjects who, in whole (e.g., systemically) or in part (e.g., locally, tissue, organ), are being or will be, treated for a disease or disorder associated with a diminished level or activity of renalase. The skilled artisan will appreciate, based upon the teachings provided herein, that the diseases and disorders treatable by the compositions and methods described herein encompass any disease or disorder where in an increase in renalase will promote a positive therapeutic outcome.

One of skill in the art will realize that in addition to activating renalase directly, diminishing the amount or activity of a molecule that itself diminishes the amount or activity of renalase can serve to increase the amount or activity of renalase. Thus, a renalase activator can include, but should not be construed as being limited to, a chemical compound, a protein, a peptidomemetic, an antibody, a ribozyme, and an antisense nucleic acid molecule. One of skill in the art would readily appreciate, based on the disclosure provided herein, that a renalase activator encompasses a chemical compound that increases the level, enzymatic activity, or substrate binding activity of renalase. Additionally, a renalase activator encompasses a chemically modified compound, and derivatives, as is well known to one of skill in the chemical arts.

It will be understood by one skilled in the art, based upon the disclosure provided herein, that an increase in the level of renalase encompasses the increase in renalase expression, including transcription, translation, or both. The skilled artisan will also appreciate, once armed with the teachings of the present invention, that an increase in the level of renalase includes an increase in renalase activity (e.g., enzymatic activity, substrate binding activity, etc.). Thus, increasing the level or activity of renalase includes, but is not limited to, increasing the amount of renalase polypeptide, increasing transcription, translation, or both, of a nucleic acid encoding renalase; and it also includes increasing any activity of a renalase polypeptide as well. The renalase activator compositions and methods of the invention can selectively activate renalase, or can activate both renalase and another molecule. Thus, the present invention relates to administration of a renalase polypeptide, a recombinant renalase polypeptide, an active renalase polypeptide fragment, or an activator of renalase expression or activity.

Further, one of skill in the art would, when equipped with this disclosure and the methods exemplified herein, appreciate that a renalase activator includes such activators as discovered in the future, as can be identified by well-known criteria in the art of pharmacology, such as the physiological results of activation of renalase as described in detail herein and/or as known in the art. Therefore, the present invention is not limited in any way to any particular renalase activator as exemplified or disclosed herein; rather, the invention encompasses those activators that would be understood by the routineer to be useful as are known in the art and as are discovered in the future.

Further methods of identifying and producing a renalase activator are well known to those of ordinary skill in the art, including, but not limited, obtaining an activator from a naturally occurring source (e.g., *Streptomyces* sp., *Pseudomonas* sp., *Stylotella aurantium*, etc.). Alternatively, a renalase activator can be synthesized chemically. Further, the routineer would appreciate, based upon the teachings provided herein, that a renalase activator can be obtained from a recombinant organism. Compositions and methods for chemically synthesizing renalase activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding an protein that is an activator of renalase. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of renalase can serve to increase the amount or activity of renalase. Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity renalase, thereby increasing the amount or activity of renalase. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of renalase can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that a renalase activator, renalase polypeptide, a recombinant renalase polypeptide, or an active renalase polypeptide fragment can be administered singly or in any combination thereof. One of skill in the art will also appreciate administration can be acute (e.g., over a short period of time, such as a day, a week or a month) or chronic (e.g., over a long period of time, such as several months or a year or more). Further, a renalase polypeptide, a recombinant renalase polypeptide, or an active renalase polypeptide fragment can be administered singly or in any combination thereof in a temporal sense, in that they may be administered simultaneously, before, and/or after each other. One of ordinary skill in the art will appreciate, based on the disclosure provided herein, that a renalase polypeptide, a recombinant renalase polypeptide, or an active renalase polypeptide fragment can be used, and that an activator can be used alone or in any combination with another renalase polypeptide, recombinant renalase polypeptide, active renalase polypeptide fragment, or renalase activator to effect a therapeutic result.

It will be appreciated by one of skill in the art, when armed with the present disclosure including the methods detailed herein, that the invention is not limited to treatment of a disease or disorder once is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that a renalase molecule (e.g., polypeptide, peptide, etc.), or a renalase activator, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject a renalase polypeptide, a recombinant renalase polypeptide, an active renalase polypeptide fragment, or renalase activator as a preventative measure against a disease or disorder.

As more fully discussed elsewhere herein, methods of increasing the level or activity of a renalase encompass a wide plethora of techniques for increasing not only renalase activity, but also for increasing expression of a nucleic acid encoding renalase. Additionally, as disclosed elsewhere herein, one skilled in the art would understand, once armed with the teaching provided herein, that the present invention encompasses a method of preventing a wide variety of diseases or disorders where increased expression and/or activity of renalase mediates, treats or prevents a disease or disorder. Further, the invention encompasses treatment or prevention of such diseases or disorders discovered in the future.

The invention encompasses administration of a renalase polypeptide, a recombinant renalase polypeptide, an active renalase polypeptide fragment, or a renalase activator to practice the methods of the invention; the skilled artisan would understand, based on the disclosure provided herein, how to formulate and administer the appropriate renalase polypeptide, recombinant renalase polypeptide, active renalase polypeptide fragment, or renalase activator to a subject. However, the present invention is not limited to any particular method of administration or treatment regimen. This is especially true where it would be appreciated by one skilled in the art, equipped with the disclosure provided herein, including the reduction to practice using an art-recognized model of ischemia-reperfusion injury, that methods of administering a renalase polypeptide, a recombinant renalase polypeptide, an active renalase polypeptide fragment, or renalase activator can be determined by one of skill in the pharmacological arts.

As used herein, the term "pharmaceutically-acceptable carrier" means a chemical composition with which an appropriate renalase modulator may be combined and which, following the combination, can be used to administer the appropriate renalase modulator thereof, to a subject.

Methods of Diagnosis

In some embodiments, a change (i.e., increase or decrease) in the level of renalase compared with a comparator is used in the methods of the invention as marker for the diagnosis of a renal disease or disorder, or a cardiac disease or disorder, as well as for monitoring the treatment of a renal or cardiac disease or disorder.

In one embodiment, the invention is a method of diagnosing a renal disease or disorder, or a cardiac disease or disorder, of a subject by assessing the level of renalase in a biological sample of the subject. In one embodiment biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In another embodiment, the invention is a method of monitoring the progression of a renal disease or disorder, or a cardiac disease or disorder, of a subject by assessing the level of renalase in a biological sample of the subject. In one embodiment biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In a further embodiment, the invention is a method of assessing the severity of a renal disease or disorder, or a cardiac disease or disorder, of a subject by assessing the level of renalase in a biological sample of the subject. In one embodiment biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In another embodiment, the invention is a method of selecting a treatment regimen to treat a renal disease or disorder, or a cardiac disease or disorder, of a subject by assessing the level of renalase in a biological sample of the subject. In one embodiment biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In another embodiment, the invention is a method of monitoring the effect of a treatment of a renal disease or disorder, or a cardiac disease or disorder, of a subject by assessing the level of renalase in a biological sample of the subject. In one embodiment biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In various embodiments, the subject is a human subject, and may be of any race, sex and age. Representative subjects include those who are suspected of having experienced a renal or cardiac injury, such as IR injury, those who have been diagnosed as having experienced a renal or cardiac injury, such as IR injury, those who have been diagnosed as having a disease or disorder associated with a renal or cardiac injury, such as IR injury, and those who are at risk of developing a disease or disorder associated with a renal or cardiac injury, such as IR injury.

Information obtained from the methods of the invention described herein can be used alone, or in combination with other information (e.g., disease status, disease history, vital signs, blood chemistry, etc.) from the subject or from the biological sample obtained from the subject.

In the diagnostic methods of the invention, a biological sample obtained from a subject is assessed for the level of renalase contained therein. In one embodiment, the biological sample is a sample containing at least a fragment of a renalase polypeptide useful in the methods described herein.

In other various embodiments of the methods of the invention, the level of renalase is determined to be reduced when the level of renalase is reduced by at least 10%, by at least 20%, by at least 30%, by at least 40%, by at least 50%, by at least 60%, by at least 70%, by at least 80%, by at least 90%, or by at least 100%, when compared to with a comparator control. In various embodiments, a reduced level of renalase is indicative of a disease or disorder.

In other various embodiments of the methods of the invention, the level of renalase is determined to be increased when the level of renalase is increased by at least 10%, by at least 20%, by at least 30%, by at least 40%, by at least 50%, by at least 60%, by at least 70%, by at least 80%, by at least 90%, or by at least 100%, when compared to with a comparator control. In various embodiments, an increased level of renalase is indicative of a disease or disorder.

In the methods of the invention, a biological sample from a subject is assessed for the level of renalase in the biological sample obtained from the patient. The level of renalase in the biological sample can be determined by assessing the amount of renalase polypeptide in the biological sample, the amount of renalase mRNA in the biological sample, the amount of renalase enzymatic activity in the biological sample, or a combination thereof.

In various embodiments of the methods of the invention, methods of measuring renalase levels in a biological sample obtained from a patient include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

Therapeutic Inhibitor Compositions and Methods

In various embodiments, the present invention includes renalase inhibitor compositions and methods of treating or preventing a disease or disorder where a diminished activity or level of renalase is desired. One non-limiting example of a disease or disorder where a diminished activity or level of renalase is desired which can be treated or prevented with the compositions and methods of the invention includes cancer. In various embodiments, the renalase inhibitor compositions and methods of treatment or prevention of the invention diminish the amount of renalase polypeptide, the amount of renalase mRNA, the amount of renalase enzymatic activity, the amount of renalase substrate binding activity, or a combination thereof.

It will be understood by one skilled in the art, based upon the disclosure provided herein, that a decrease in the level of renalase encompasses the decrease in renalase expression, including transcription, translation, or both. The skilled artisan will also appreciate, once armed with the teachings of the present invention, that a decrease in the level of renalase includes a decrease in renalase activity (e.g., enzymatic activity, substrate binding activity, etc.). Thus, decreasing the level or activity of renalase includes, but is not limited to, decreasing transcription, translation, or both, of a nucleic acid encoding renalase; and it also includes decreasing any activity of a renalase polypeptide as well. The renalase inhibitor compositions and methods of the invention can selectively inhibit renalase, or can inhibit both renalase and another molecule.

Inhibition of renalase can be assessed using a wide variety of methods, including those disclosed herein, as well as methods known in the art or to be developed in the future. That is, the routineer would appreciate, based upon the disclosure provided herein, that decreasing the level or activity of renalase can be readily assessed using methods that assess the level of a nucleic acid encoding renalase (e.g., mRNA), the level of a renalase polypeptide present in a biological sample, the level of renalase activity (e.g., enzymatic activity, substrate binding activity, etc.), or combinations thereof.

One skilled in the art, based upon the disclosure provided herein, would understand that the invention is useful in treating or preventing in a subject in need thereof, whether or not the subject is also being treated with other medication or therapy. Further, the skilled artisan would further appreciate, based upon the teachings provided herein, that the disease or disorders treatable by the compositions and methods described herein encompass any disease or disorder where renalase plays a role and where diminished renalase level or activity will promote a positive therapeutic outcome.

The renalase inhibitor compositions and methods of the invention that decrease the level or activity (e.g., enzymatic activity, substrate binding activity, etc.) of renalase include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof. One of skill in the art would readily appreciate, based on the disclosure provided herein, that a renalase inhibitor composition encompasses a chemical compound that decreases the level or activity of renalase. Additionally, a renalase inhibitor composition encompasses a chemically modified compound, and derivatives, as is well known to one of skill in the chemical arts.

The renalase inhibitor compositions and methods of the invention that decrease the level or activity (e.g., enzymatic activity, substrate binding activity, etc.) of renalase include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and a humanized antibodies. In one embodiment, the antibody of the invention is an antibody that specifically binds to renalase.

Further, one of skill in the art, when equipped with this disclosure and the methods exemplified herein, would appreciate that a renalase inhibitor composition includes such inhibitors as discovered in the future, as can be identified by well-known criteria in the art of pharmacology, such as the physiological results of inhibition of renalase as described in detail herein and/or as known in the art. Therefore, the present invention is not limited in any way to any particular renalase inhibitor composition as exemplified or disclosed herein; rather, the invention encompasses those inhibitor compositions that would be understood by the routineer to be useful as are known in the art and as are discovered in the future.

Further methods of identifying and producing renalase inhibitor compositions are well known to those of ordinary skill in the art, including, but not limited, obtaining an inhibitor from a naturally occurring source (e.g., *Streptomyces* sp., *Pseudomonas* sp., *Stylotella aurantium*, etc.). Alternatively, a renalase inhibitor can be synthesized chemically. Further, the routineer would appreciate, based upon the teachings provided herein, that a renalase inhibitor composition can be obtained from a recombinant organism. Compositions and methods for chemically synthesizing renalase inhibitors and for obtaining them from natural sources are well known in the art and are described in the art.

One of skill in the art will appreciate that an inhibitor can be administered as a small molecule chemical, a protein, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of renalase. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the amount or activity of renalase can serve in the compositions and methods of the present invention to decrease the amount or activity of renalase.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of renalase, or to diminish the amount of a molecule that causes an increase in the amount or activity of renalase, thereby decreasing the amount or activity of renalase.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing renalase, or of a gene expressing a protein that increases the level or activity of renalase, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168, 053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that inhibitors of renalase can be administered acutely (e.g., over a short period of time, such as a day, a week or a month) or chronically (e.g., over a long period of time, such as several months or a year or more). One of skill in the art will appreciate that inhibitors of renalase can be administered singly or in any combination with other agents. Further, renalase inhibitors can be administered singly or in any combination in a temporal sense, in that they may be administered concurrently, or before, and/or after each other. One of ordinary skill in the art will appreciate, based on the disclosure provided herein, that renalase inhibitor compositions can be used to treat or prevent a disease or disorder in a subject in need thereof, and that an inhibitor composition can be used alone or in any combination with another inhibitor to effect a therapeutic result.

In various embodiments, any of the inhibitors of renalase of the invention described herein can be administered alone or in combination with other inhibitors of other molecules associated with cancer.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that a renalase inhibitor composition, as discussed previously elsewhere herein, can be administered to a subject prior to the onset of the disease or disorder, thereby preventing the disease or disorder from developing. The preventive methods described herein also include the treatment of a subject that is in remission for the prevention of a recurrence of a disease or disorder.

One of skill in the art, when armed with the disclosure herein, would appreciate that the prevention of a disease or disorder encompasses administering to a subject a renalase inhibitor composition as a preventative measure against the disease or disorder. As more fully discussed elsewhere herein, methods of decreasing the level or activity of renalase encompass a wide plethora of techniques for decreasing not only renalase activity, but also for decreasing expression of a nucleic acid encoding renalase, including either a decrease in transcription, a decrease in translation, or both.

Additionally, as disclosed elsewhere herein, one skilled in the art would understand, once armed with the teaching provided herein, that the present invention encompasses a method of preventing a wide variety of diseases, disorders and pathologies where a decrease in expression and/or activity of renalase mediates, treats or prevents the disease, disorder or pathology. Methods for assessing whether a disease relates to the levels or activity of renalase are known in the art. Further, the invention encompasses treatment or prevention of such diseases discovered in the future.

The invention encompasses administration of an inhibitor of renalase to practice the methods of the invention; the skilled artisan would understand, based on the disclosure provided herein, how to formulate and administer the appropriate renalase inhibitor to a subject. However, the present invention is not limited to any particular method of administration or treatment regimen.

Kits

The present invention also pertains to kits useful in the methods of the invention. Such kits comprise various combinations of components useful in any of the methods described elsewhere herein, including for example, a renalase activator, a renalase inhibitor, materials for quantitatively analyzing renalase polypeptide or renalase nucleic acid, materials for assessing the activity of a renalase polypeptide or a renalase nucleic acid, and instructional material. For example, in one embodiment, the kit comprises components useful for the quantification of renalase nucleic acid in a biological sample. In another embodiment, the kit comprises components useful for the quantification of renalase polypeptide in a biological sample. In a further embodiment, the kit comprises components useful for the assessment of the activity (e.g., enzymatic activity, substrate binding activity, etc.) of a renalase polypeptide in a biological sample.

In a further embodiment, the kit comprises the components of an assay for monitoring the effectiveness of a treatment administered to a subject in need thereof, containing instructional material and the components for determining whether the level of renalase in a biological sample obtained from the subject is modulated during or after administration of the treatment. In various embodiments, to determine whether the level of renalase is modulated in a biological sample obtained from the subject, the level of renalase is compared with the level of at least one comparator control contained in the kit, such as a positive control, a negative control, a historical control, a historical norm, or the level of another reference molecule in the biological sample. In certain embodiments, the ratio of renalase and a reference molecule is determined to aid in the monitoring of the treatment.

Pharmaceutical Composition and Administration

Compositions comprising a renalase polypeptide, a renalase polypeptide fragment, an activator of renalase level or activity, or an inhibitor of renalase level or activity can be formulated and administered to a subject, as now described. By way of non-limiting examples, a composition identified as a useful renalase active or activator, including renalase polypeptides, recombinant renalase polypeptides, and active renalase polypeptide fragments, for the treatment and/or prevention of a disease or disorder can be formulated and administered to a subject, as now described. By way of more non-limiting examples, a composition identified as a useful renalase inhibitor, including a chemical compound, a protein, a peptide, a peptidomemetic, an antibody, a ribozyme, a small molecule chemical compound, an antisense nucleic acid molecule (e.g., siRNA, miRNA, etc.), for the treatment and/or prevention of a disease or disorder can be formulated and administered to a subject, as now described.

The invention encompasses the preparation and use of pharmaceutical compositions comprising a composition useful for the treatment or prevention of a disease or disorder, disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

In various embodiments, the active ingredient is a renalase polypeptide, a renalase polypeptide fragment, an activator of renalase level or activity, an inhibitor of renalase level or activity, or a combination thereof, as elsewhere described herein.

As used herein, the term "pharmaceutically-acceptable carrier" means a chemical composition with which an appropriate renalase modulator thereof, may be combined and which, following the combination, can be used to administer the appropriate renalase modulator (e.g., activator, inhibitor, etc.) thereof, to a subject.

The pharmaceutical compositions useful for practicing the invention may be administered to deliver a dose of between about 0.1 ng/kg/day and 100 mg/kg/day, or more.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate modulator thereof, according to the methods of the invention.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, transdermal, subcutaneous, intramuscular, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

Pharmaceutically acceptable excipients used in the manufacture of pharmaceutical compositions include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Liquid formulations of a pharmaceutical composition of the invention may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose.

Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.01 mg to about 1000 mg per kilogram of body weight of the animal. The precise dosage administered will vary depending upon any number of factors, including, but not limited to, the type of animal and type of disease or disorder being treated, the age of the animal and the route of administration. Preferably, the dosage of the compound will vary from about 1 mg to about 100 mg per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease or disorder being treated, the type and age of the animal, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Renalase Protects Against Ischemic Acute Kidney Injury in Mice

Renalase is a renal proximal tubule secreted amine oxidase that degrades circulating catecholamines and reduces myocardial necrosis. The data presented herein demonstrate that renalase protects against renal ischemia and reperfusion injury. As shown herein, renalase is selectively expressed in proximal but not distal renal tubules. Mice subjected to renal ischemia reperfusion injury had significantly reduced kidney and plasma renalase levels compared to the sham-operated mice. Consistent with this, mouse plasma norepinephrine levels increased significantly after renal ischemia reperfusion injury. Furthermore, renalase deficient mice subjected to renal ischemia and reperfusion had exacerbated renal tubular inflammation, necrosis and apoptosis with higher plasma catecholamine levels compared to the renalase wild type mice. Administration of recombinant human renalase reduced plasma catecholamine levels and ameliorated ischemic acute kidney injury in renalase wild type mice by reducing renal tubular necrosis, inflammation and apoptosis. Taken together, the data show that renalase protects against ischemic acute kidney injury by reducing renal tubular necrosis, apoptosis and inflammation. Recombinant renalase therapy provides a novel therapeutic approach for the prevention and treatment of acute kidney injury. In addition, as plasma renalase decreases after ischemic acute kidney injury, plasma renalase levels serves as a novel and sensitive biomarker for the detection of acute kidney injury.

As described herein, experiments were conducted to assess whether ischemic AKI in mice leads to renalase deficiency and whether renalase deficiency directly exacerbates ischemic AKI. Thus, experiments were performed to test whether 1) ischemic AKI leads to reduced kidney and plasma renalase levels, 2) ischemic AKI-induced renalase deficiency leads to elevated plasma catecholamine (norepinephrine) levels, 3) renalase deficient mice exhibit increased renal IR injury and 4) exogenous administration of recombinant human renalase directly protects against ischemic AKI in mice.

Ischemic AKI is complicated by intra-renal recruitment of pro-inflammatory leukocytes and systemic inflammation (Okusa, 2010, Contrib Nephrol 165: 153-158). Recent studies have demonstrated that renal IR is not a single organ disease but involves multiple extra-renal organs including the liver, intestine and lung (Paladino et al., 2009, Microvasc Res 77: 8-12; Park et al., 2011, Lab Invest 91: 63-84). Although many advances have been made detailing the mechanisms of renal tubular cell death following ischemic AKI, the trigger that orchestrates renal and systemic inflammation following ischemic AKI remains unknown. While not wishing to be bound by any particular theory, extra-renal effects of ischemic AKI may explain the disproportionately high mortality in patients with AKI. Therefore, ways to prevent these systemic, extra-renal complications from AKI would contribute greatly to improved patient care and survival.

As described herein, renal tubular cell death and acute reduction in renal function after ischemic AKI led to drastic reductions in renal and plasma renalase levels with a resultant increase in plasma norepinephrine. These findings are consistent with the explanation that kidney proximal tubule is a major source of circulating renalase. Moreover, the data suggest that secreted renalase is degraded rapidly in plasma and constant new renalase synthesis and release by the kidney must occur to maintain normal plasma renalase levels. Furthermore, since kidney and plasma renalase levels rapidly decreased after ischemic AKI in mice, urine and plasma renalase may also serve as a novel and sensitive biomarker for the early detection of ischemic AKI.

Recombinant renalase therapy provides a novel therapeutic tool for the prevention and treatment of AKI as the powerful protective effect of recombinant renalase against renal IR injury has been described herein. Specifically, exogenous recombinant renalase attenuated renal tubular necrosis (Jablonski renal injury score). Furthermore, the reduced influx of pro-inflammatory neutrophils and macrophages into the kidney and renal tubular apoptosis after renal IR in recombinant renalase-treated mouse kidneys was demonstrated. These data are consistent with the explanation that exogenous administration of human recombinant renalase provides powerful renal protection against ischemic AKI by targeting all 3 pathways (necrosis, apoptosis and inflammation) of renal cell injury.

The recombinant renalase (1.5 mg/kg) provided significant but partial renal protection (creatinine decreased from ~2.4 mg/dL to 1.4 mg/dL) most likely due to the severity of the ischemic AKI model described herein (30 min. warm ischemia). Thirty min. of renal ischemia would have caused significant renal tubular necrosis during ischemia that may not be rescued with renalase treatment. It was also observed that renalase does not provide dose-dependent protection and at doses of 4.5 mg/kg there was some reversal of protection. It is likely that high dose (4.5 mg/kg) failed to provide increased renal protection since renalase causes dose-dependent reduction in systemic blood pressure (Xu et al., 2005, J Clin Invest 115: 1275-1280). A previous study showed that renalase at a 4 mg/kg dose reduced mean arterial pressure by ~40% (Xu et al., 2005, J Clin Invest 115: 1275-1280). This observation is consistent with the explanation that the reduction in systemic blood pressure may have negated the renal protective effects of high dose recombinant renalase.

Recombinant renalase therapy was also partially protective when administered 30 min. after renal ischemia. Accordingly, recombinant renalase therapy may be effective for a diverse group of patients at risk for ischemic AKI. While renal ischemia can be anticipated in many surgical procedures, a significant number of patients present to the hospital after renal ischemic injury has already occurred. Post-ischemic therapy for AKI will increase the translational, as well as clinical significance, because not all ischemic AKI can be anticipated in advance. However, significant differences in the efficacy of renalase administered 10 min. before renal ischemia and 30 min. after reperfusion were noted. Although not wishing to be bound by any particular theory, this may be because of the severity of early reperfusion injury that occurs after 30 min. warm kidney ischemia. It appears that recombinant renalase must be present in circulation to counteract the significant renal injury that occurs during 30 min. after reperfusion.

As described herein, increases in plasma norepinephrine levels were greater in renalase KO mice compared to the renalase WT mice after renal IR injury. Wu et al. have also demonstrated that plasma levels of catecholamines, including epinephrine, dopamine and norepinephrine, are increased in renalase KO mice (Wu et al., 2011, Kidney Int 79: 853-860). It was also shown in the studies described herein that renalase KO mice suffered increased renal tubular injury after renal IR. Furthermore, increased TNF-α, MCP-1, and MIP-2 were demonstrated after renal IR in renalase deficient mice. In particular, MIP-2 is a chemokine involved in inflammation and immunoregulation and is a potent regulator of neutrophil chemotaxis (Lemay et al., 2000, Transplantation 69: 959-963). Consistent with the findings described herein, renalase KO mice have exacerbated myocardial necrosis due to IR (Wu et al., 2011, Kidney Int 79: 853-860). Taken together, renalase deficiency appears to exacerbate ischemic organ injury and results in higher plasma catecholamine levels.

Although not wishing to be bound by any particular theory, the findings described herein are consistent with the explanation that renal protective effects of recombinant renalase are, at least in part, due to increased metabolism of plasma and tissue catecholamines. It is shown herein that recombinant renalase-mediated renal protection also resulted in significantly reduced plasma catecholamines levels. Increased catecholamine levels after ischemic AKI may exacerbate kidney injury by decreasing renal blood flow as well as by direct effects on renal tubules and immune cells. Catecholamines have been implicated in promoting tissue and organ injury in sepsis and systemic inflammatory response syndrome (Miksa et al., 2009, PLoS One 4: e5504; Wang et al., 2000, Biochim Biophys Acta 1535: 36-44). For example, gut-derived norepinephrine has been implicated in causing hepatic injury and systemic inflammation in sepsis (Koo et al., 2000, Int J Mol Med 5: 457-465; Yang et al., 2000, Am J Physiol Gastrointest Liver Physiol 279: G1274-G1281; Zhou et al., 2004, Biochim Biophys Acta 1689: 212-218). Previous studies have shown that intestine-derived norepinephrine activates hepatic Kupffer cell alpha2-adrenoceptors to increase TNF-α generation and release (Miksa et al., 2009, PLoS One 4: e5504; Yang et al., 2000, Am J Physiol Gastrointest Liver Physiol 279: G1274-G1281; Yang et al., 2001, Am J Physiol Gastrointest Liver Physiol 281: G1014-G1021; Zhou et al., 2001, Biochim Biophys Acta 1537: 49-57). In septic rats, alpha2 adrenergic receptors upregulate in Kupffer cells to potentiate inflammatory response and organ injury (Miksa et al., 2009, PLoS One 4: e5504). Furthermore, alpha1 adrenergic receptors increase LPS-mediated induction of pro-inflammatory cytokines in human monocytes and macrophages (Grisanti et al., 2011, J Pharmacol Exp Ther 338: 648-657). Therefore, both alpha1 and alpha2 adrenergic receptors are implicated in pro-inflammatory effects of increased circulating catecholamines. Supporting a pathogenic role of alpha adrenergic receptors against ischemic AKI, it was found that blockade of alpha adrenergic receptors provided significant renal protection in renalase WT as well as renalase KO mice.

The methods and materials of this example are now described.

Synthesis of Recombinant Human Renalase

Human recombinant renalase was synthesized as described (Desir et al, 2012, J. of the Am. Heart Assn, 1(4):e002634).

Murine Model of Renal Ischemia/Reperfusion (IR) Injury

Adult male renalase deficient (KO) mice (Wu et al., 2011, Kidney Int 79: 853-860) on a C57BL/6 background were subjected to renal ischemia/reperfusion (IR) as described (Kim et al., 2009, Kidney Int 75: 809-823; Kim et al., 2010, Am J Physiol Renal Physiol 299(2):F347-58). Renalase KO or wild type (WT) mice (C57BL/6 from Harlan Labs, Indianapolis, Ind.) were subjected to sham-operation or to 20 min. (moderate) or 30 min. (severe) renal ischemia and 24 hr. reperfusion. To test the renal protective effects of recombinant human renalase, mice were pretreated with saline (vehicle) or with recombinant renalase (0.5, 1.5 or 4.5 mg/kg, s.c.) 10 min. prior to 30 min. renal ischemia. It was also tested whether renalase treatment after completion of renal ischemia also provides renal protection. Separate cohorts of mice were treated with saline or with renalase (1.5 mg/kg, s.c.) 30 min. or 60 min. after reperfusion of the ischemic kidney. To test whether blocking alpha receptors would mimic the renal protective effects of human recombinant renalase administration, phentolamine (an alpha receptor antagonist, 5 mg/kg, i.p.) was given in some mice 15 min. before renal ischemia.

Measurement of Renal Function

Plasma creatinine was measured as described with an enzymatic creatinine reagent kit according to the manufacturer's instructions (Thermo Fisher Scientific, Waltham, Mass.) (Slot, 1965, J Clin Lab Invest 17: 381-387).

Measurement of Plasma Norepinephrine

Plasma norepinephrine in mice subjected to sham-operation or to renal IR was measured with a commercial ELISA kit according to the manufacturer's instructions (Rocky Mountain Diagnostics, Colorado Springs, Colo.).

Histological Detection of Necrosis, Apoptosis and Neutrophil Infiltration

An established grading scale of necrotic injury (0-4, Renal Injury Score) to the proximal tubules was used for the histopathological assessment of IR-induced damage as outlined by Jablonski et al. (1983, Transplantation 35: 198-204) and as described in previous studies (Lee et al., 2004, J Am Soc Nephrol 15: 102-111; Lee et al., 2004, Am J Physiol Renal Physiol 286: F298-F306). Apoptosis was detected after renal IR with TUNEL staining as described (Park et al., 2011, Lab Invest 91: 63-84) using a commercially available in situ cell death detection kit (Roche, Indianapolis, Ind.) according to the instructions provided by the manufacturer. Kidney neutrophil and macrophage infiltrations were assessed with immunohistochemistry 24 hr. after IR as described previously (Park et al., 2011, Lab Invest 91: 63-84). Neutrophils and macrophages infiltrating the kidney were quantified in 5-7 randomly chosen 200× (neutrophils) or 400× (macrophages) microscope images fields in the corticomedullary junction and results were expressed as neutrophils counted per 200-400× field.

Reverse Transcription Polymerase Chain Reaction and Immunoblotting Analyses for Mouse Renalase mRNA encoding mouse renalase was measured with RT-PCR as described (Kim et al., 2010, Am J Nephrol 31: 353-362). GAPDH mRNA was also measured to control for equal RNA input. In addition, mouse kidney cortex were also collected for immunoblotting analyses of renalase (Abcam, Cambridge, Mass.) and β-actin (internal protein loading control, Sigma) as described previously (Kim et al., 2010, Am J Nephrol 31: 353-362).

Measurement of Pro-Inflammatory mRNA Expression after Intestinal IR

Kidney inflammation after renal IR in mice were additionally determined by measuring mRNA encoding markers of inflammation, including IL-17A, intercellular adhesion molecule 1 (ICAM-1), monocyte chemoattractive protein 1 (MCP-1), macrophage inflammatory protein 2 (MIP-2), tumor necrosis factor-α (TNF-α) and IL-6 (liver and kidney only). RT-PCR was performed as described (Park et al., 2011, Lab Invest 91: 63-84).

Coimmunolocalization of Endogenous Renalase with E-Cadherin or Megalin in Pig Kidney The renalase antibody was synthesized against human renalase sequence. Renalase immunohistochemistry was performed in pig kidneys. Pig kidney slices were fixed, permeabilized and incubated with anti-renalase 28-4 (raised against renalase peptide EAGTKIDVPWAGQYITSNPC (SEQ ID NO: 1) and with either anti-E-cadherin (BD Biosciences) or anti-megalin primary antibody for 2 hr. Secondary antibodies (Alexa488-goat anti-rabbit for detecting renalase) and Alexa555-goat anti-mouse (Molecular Probes, for detecting E-cadherin or megalin) were then applied. Slides were images with a fluorescence microscope (Carl Zeiss, Inc.) and photographed using a SPOT camera software (Diagnostic Instruments, Inc.).

Statistical Analysis

The data were analyzed with Student's t-test when comparing means between two groups or one-way ANOVA plus Tukey's post hoc multiple comparison test when comparing multiple groups. Two-way ANOVA plus Bonferroni posttest was used to test the effects of sham operation or renal IR injury on different mouse strains or treatment groups. The ordinal values of the renal injury scores were analyzed by the Mann-Whitney nonparametric test. In all cases, a probability statistic <0.05 was taken to indicate significance. All data are expressed throughout the text as means±SEM.

The results of this example are now described.

Renalase is Selectively Expressed in Renal Proximal Tubules

FIG. 1A shows co-immunolocalization analyses of pig kidney tissue incubated with antibodies against megalin (a marker for proximal renal tubules) or renalase. Renalase and megalin stain perfectly overlap indicating that renalase is expressed in renal proximal tubules. Co-immunolocalization studies with renalase and E-cadherin (a marker for distal renal tubules) were also performed (FIG. 1B). Unlike megalin, E-cadherin does not co-localize with renalase in pig kidneys. These data indicate selective expression of renalase in renal proximal tubules. The renalase antibody also detected renalase in mouse proximal tubules.

Plasma Norepinephrine Levels after Sham-Operation or Renal IR in Mice

Figure 2:
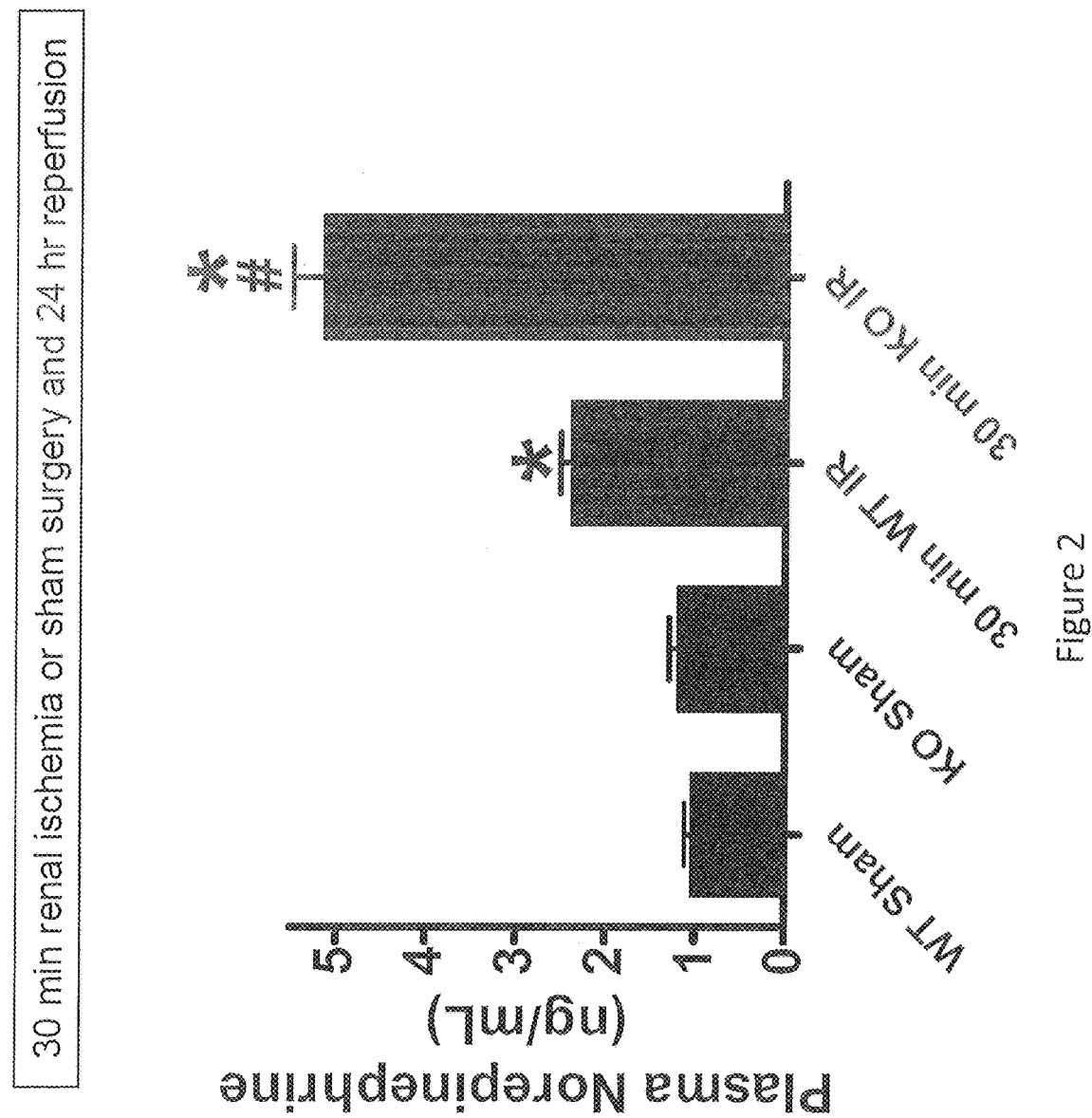
FIG. 2 is a graph showing plasma norepinephrine levels in mice. Plasma norepinephrine levels were measured in mice subjected to sham-operation or to renal ischemia/reperfusion (IR) injury (N=3-5 per group). Plasma norepinephrine concentration significantly increased 24 hr. after renal IR in renalase wild type (WT) mice and this increase was even higher in renalase deficient (KO) mice. *$P<0.05$ vs. sham group. #$P<0.05$ vs. WT IR group.

Plasma norepinephrine concentration increased 24 hr. after renal IR in renalase WT mice (>2 fold compared to sham-operated renalase WT mice, N=3-5, FIG. 2). The increase in plasma norepinephrine concentration was even higher in renalase deficient mice after renal IR (>5 fold compared to sham-operated renalase KO mice).

Plasma and Kidney Renalase Expression after Renal IR

Figure 3A:
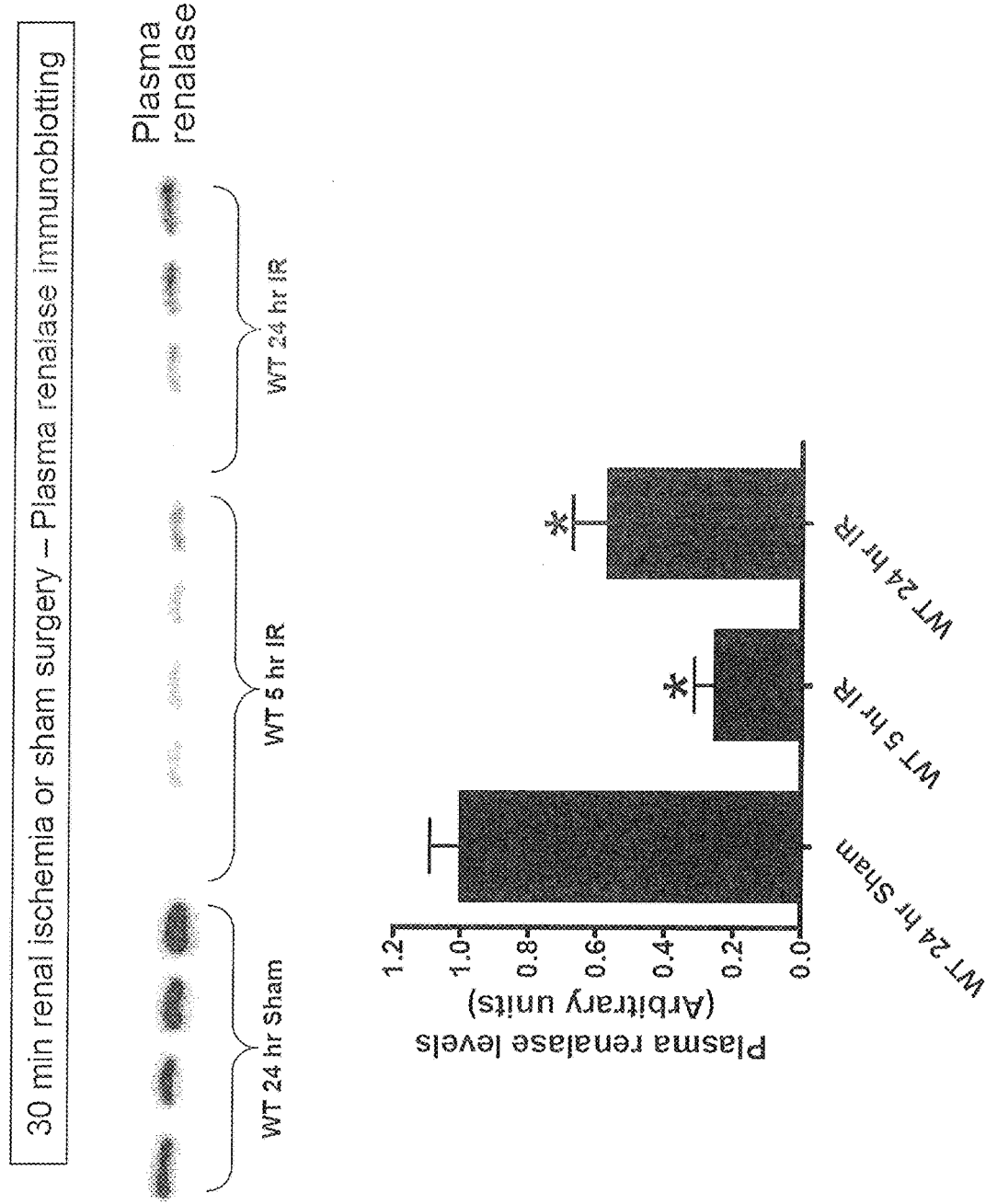
FIGS. 3A and 3B, is a set of images and graphs showing plasma and kidney renalase levels in mice.
Figure 3B:
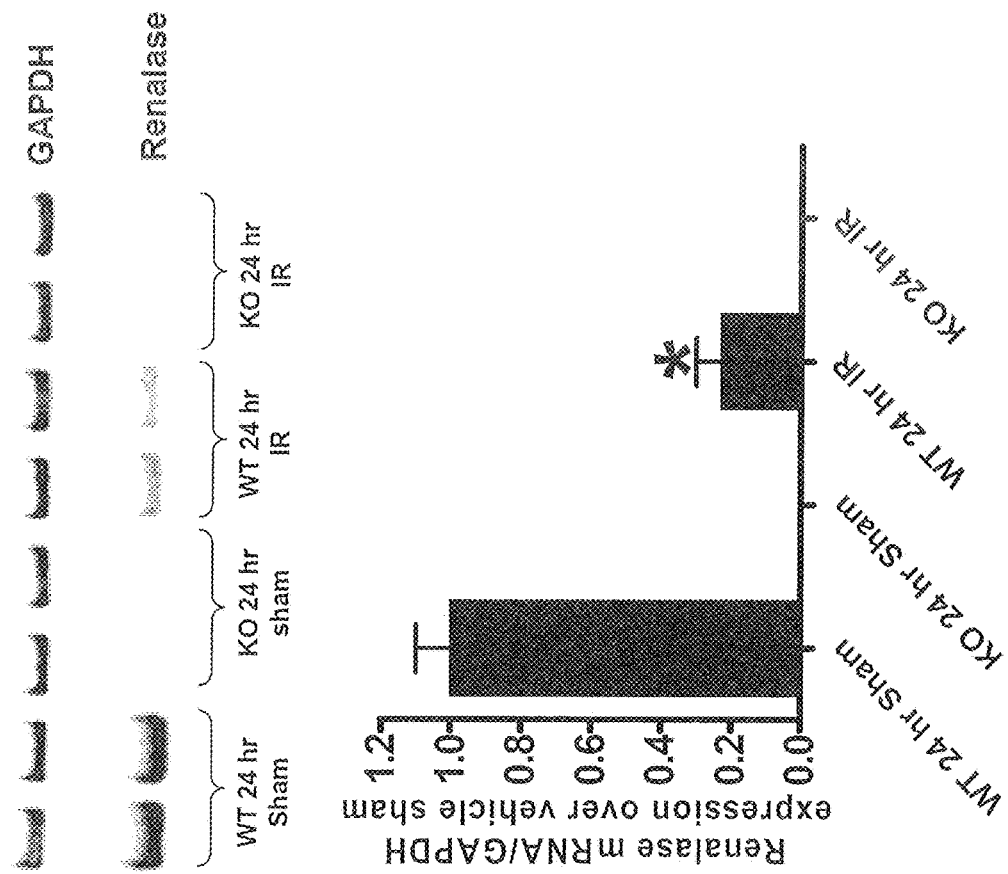

Immunoblotting for plasma renalase revealed significant reductions in plasma renalase 5 hr. and 24 hr. after renal IR (FIG. 3A, n=4-5). Consistent with this decrease in plasma renalase, kidney renalase mRNA expression was significantly attenuated 24 hr. after renal IR (FIG. 3B, n=4).

Renalase Deficient Mice have Increased Ischemic AKI after Renal IR

Figure 4A:
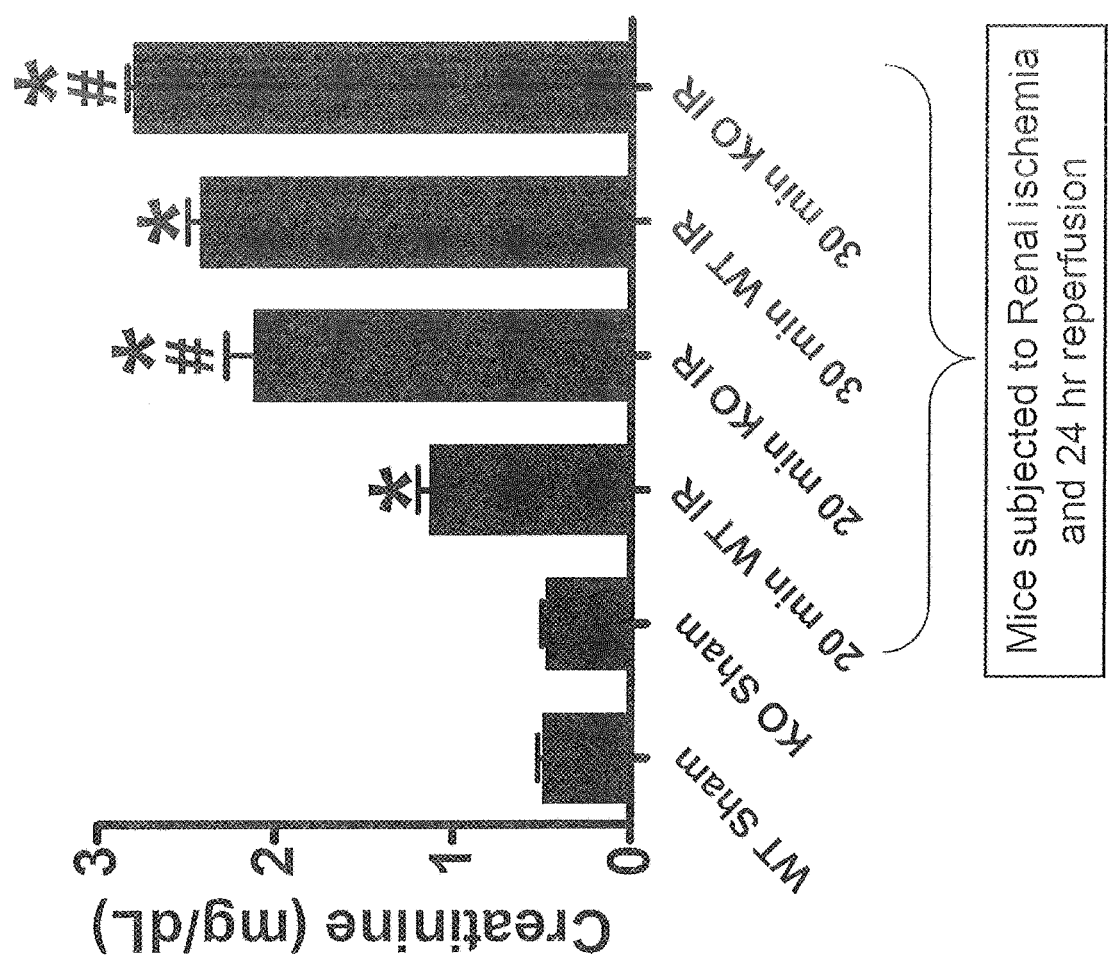
FIGS. 4A through 4D, is a set of graphs demonstrating that renalase modulates ischemic AKI in mice. Plasma creatinine levels from mice subjected to sham-surgery or to renal ischemia and reperfusion (IR).

Baseline plasma creatinine values were similar between renalase WT and renalase KO subjected to sham-operation (anesthesia, laparotomy, right nephrectomy and recovery, FIG. 4A). Plasma creatinine increased significantly in renalase WT and renalase KO mice subjected to moderate (20 min.) or severe (30 min.) renal IR compared to sham-operated mice (FIG. 4A, n=4-6). However, renalase KO mice had significantly increased renal injury indicated by higher plasma creatinine levels compared to renalase WT mice after both moderate and severe renal IR injury.

Renal Protective Effects of Exogenous Human Recombinant Renalase Administration

Figure 4B:
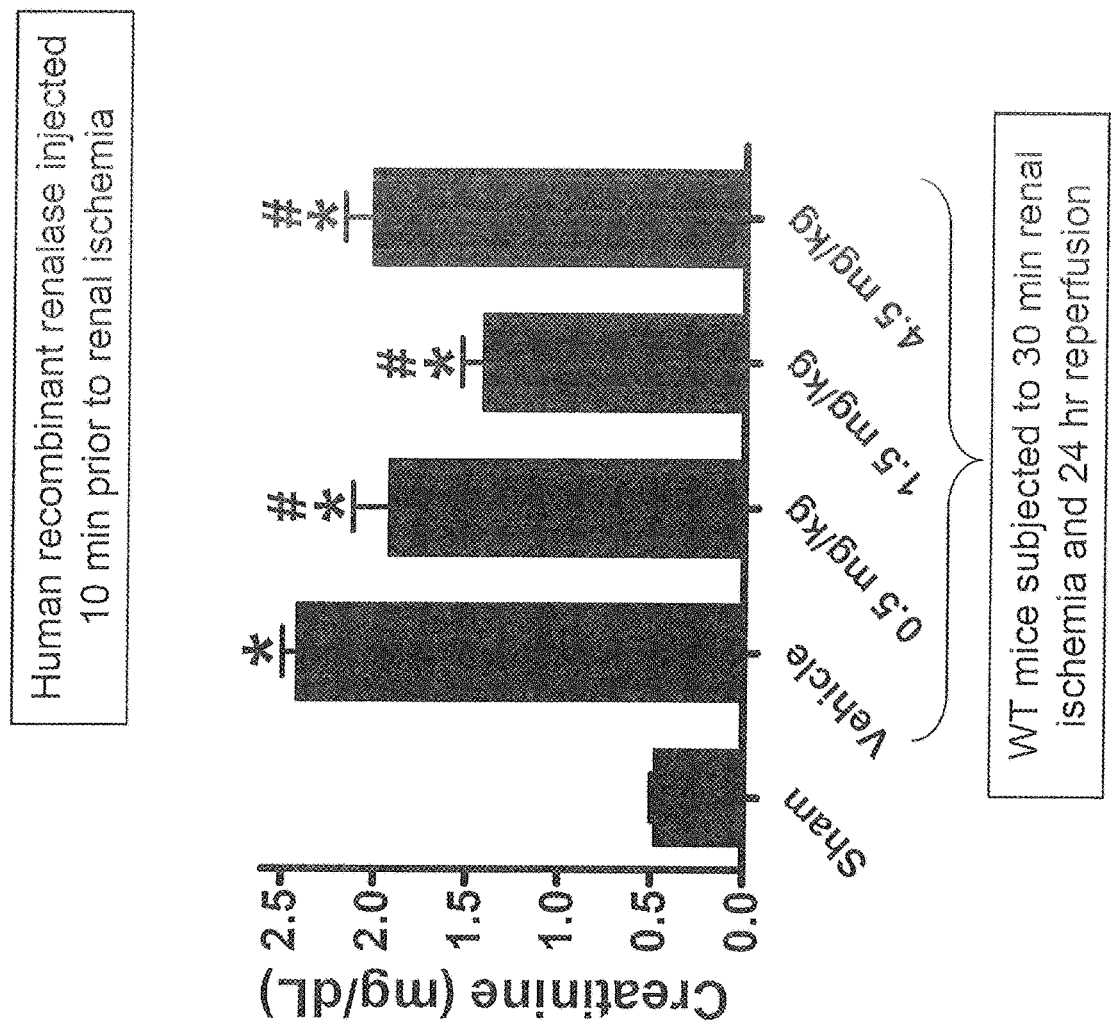

Pretreatment with exogenous human recombinant renalase protects against renal IR injury. Plasma creatinine significantly increased in vehicle (saline)-treated mice subjected to 30 min. renal IR compared to sham-operated mice (FIG. 4B, n=4-6). Pretreatment with human recombinant renalase (0.5, 1.5 or 4.5 mg/kg s.c. 10 min. before renal ischemia) significantly attenuated the increases in plasma creatinine in mice. However, higher dose of human recombinant renalase (4.5 mg/kg) provided reduced renal protection when compared with the recombinant renalase dose of 1.5 mg/kg. Exogenous renalase (1.5 mg/kg) decreased plasma norepinephrine levels in mice subjected to renal IR injury (vehicle injected mice plasma norepinephrine=2.4±0.13 ng/mL, n=4 vs. renalase injected mice plasma norepinephrine=1.6±0.2 ng/mL, N=4, P<0.05) consistent with its renal protective effects.

Figure 4C:
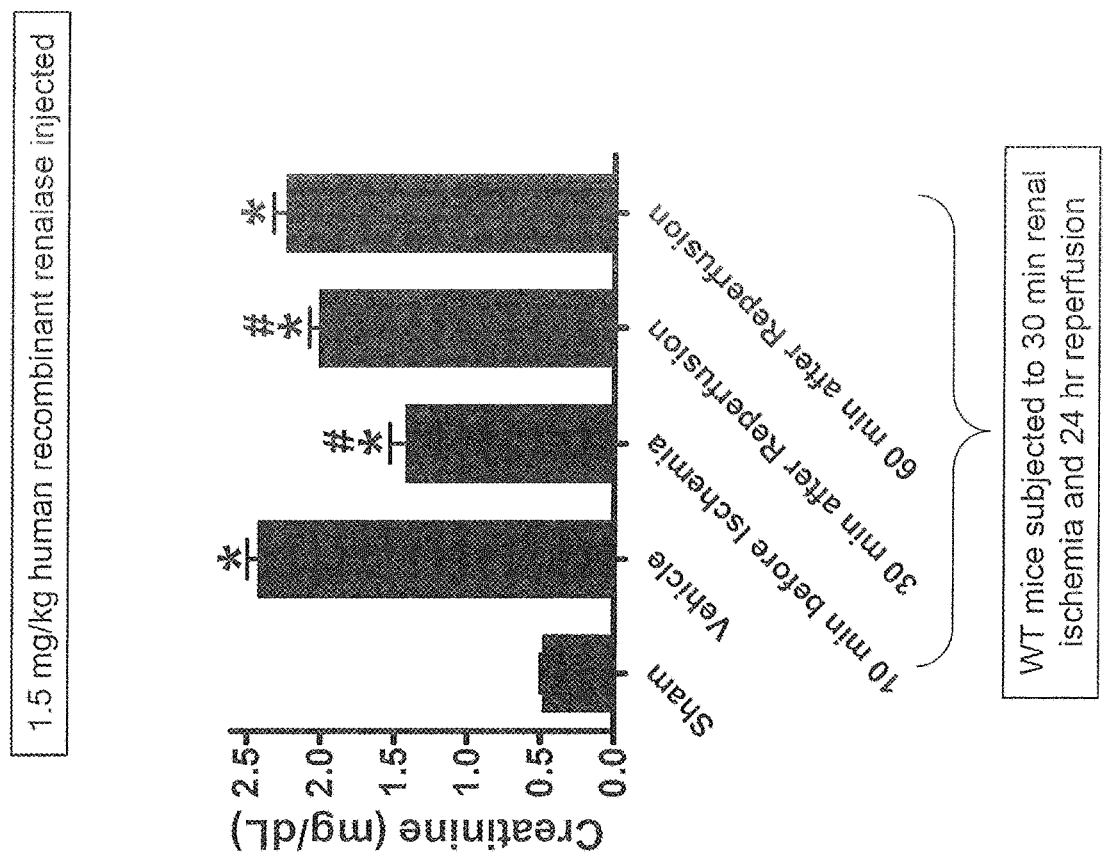

Recombinant renalase treatment after renal reperfusion (after completion of renal ischemia) protected against renal IR injury. FIG. 4C shows that recombinant renalase (1.5 mg/kg) given 30 min. after reperfusion was protective against renal IR injury (n=4-6). Administration of recombinant renalase 60 min. after did not provide renal protection against IR injury.

Renal Protective Effects of Alpha Adrenergic Receptor Blockade

Figure 4D:
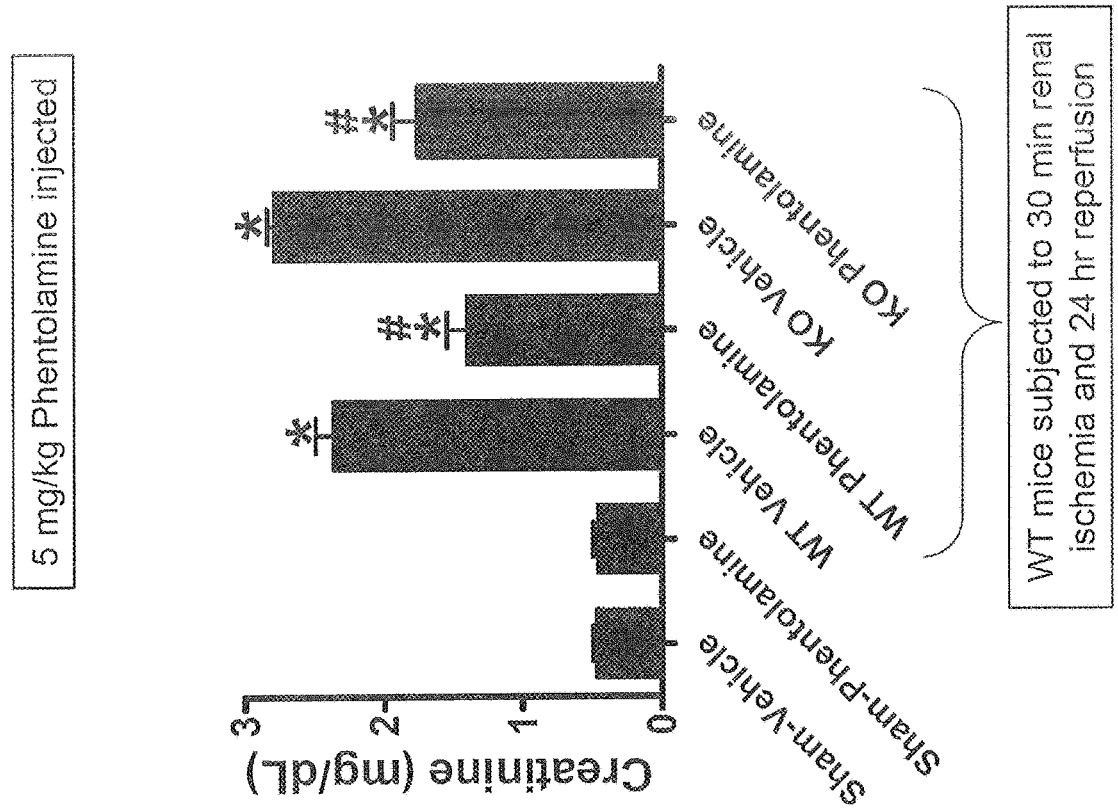

Blocking alpha adrenergic receptors mimics the renal protective effects of human recombinant renalase administration. Phentolamine (a non-specific but selective alpha adrenergic receptor antagonist, 5 mg/kg, i.p.) produced significant renal protection in renalase WT mice subjected to renal 30 min. IR injury (FIG. 4D). Furthermore, phentolamine also protected renalase KO mice against 30 min. renal IR injury (FIG. 4D).

Renalase Modulates Renal Tubular Necrosis after IR

Figure 5A:
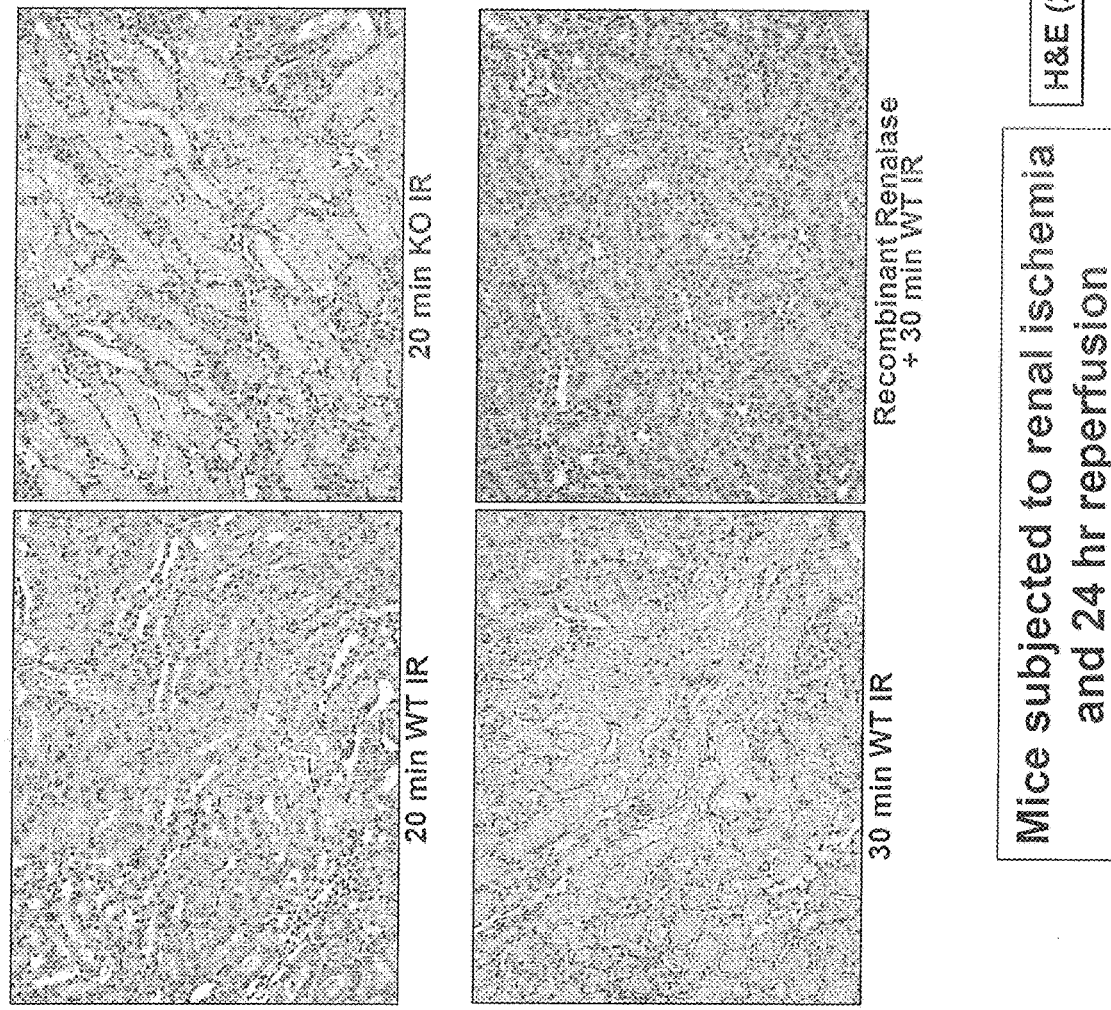
FIGS. 5A and 5B, is a set of images and a graph demonstrating that renalase modulates renal tubular necrosis after IR.
Figure 5B:
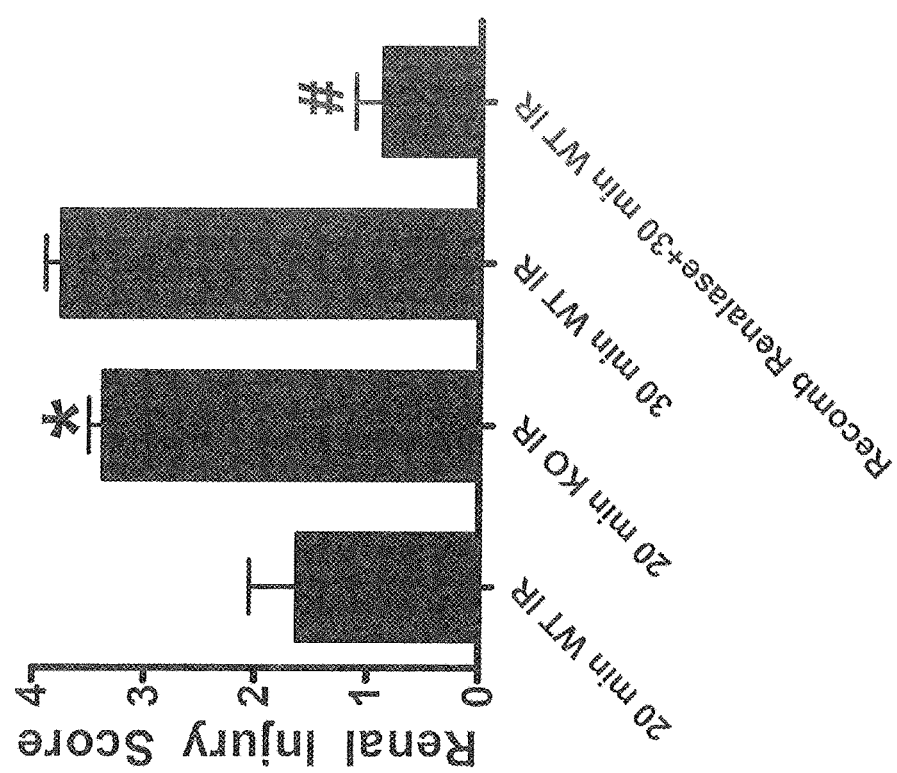

Renalase deficient mice subjected to moderate renal IR injury (20 min. renal ischemia) developed exacerbated renal histological injury compared to the renalase WT mice (increased tubular necrosis, proteinaceous casts with increased congestion, FIG. 5A, top panels, representative of 4-6 experiments). In contrast and consistent with the plasma creatinine data, renalase WT mice treated with human recombinant renalase (1.5.mg/kg) had dramatically reduced injury compared to vehicle-treated renalase WT mice (FIG. 5A, bottom panels). The Jablonski scale (Jablonski et al., 1983, Transplantation 35: 198-204) renal injury score (scale: 0-4) was used to grade renal tubular necrosis 24 hr. after renal IR (FIG. 5B, N=4-6). Renalase KO mice subjected to moderate renal IR injury (20 min. renal ischemia) showed severe acute tubular necrosis (with renal injury scores >3) unlike renalase WT mice subjected to 20 min. renal IR injury. In contrast, renalase WT mice treated with human recombinant renalase had significantly lower renal injury scores compared to vehicle-treated renalase WT mice subjected to 30 min. renal IR injury.

Figure 6A:
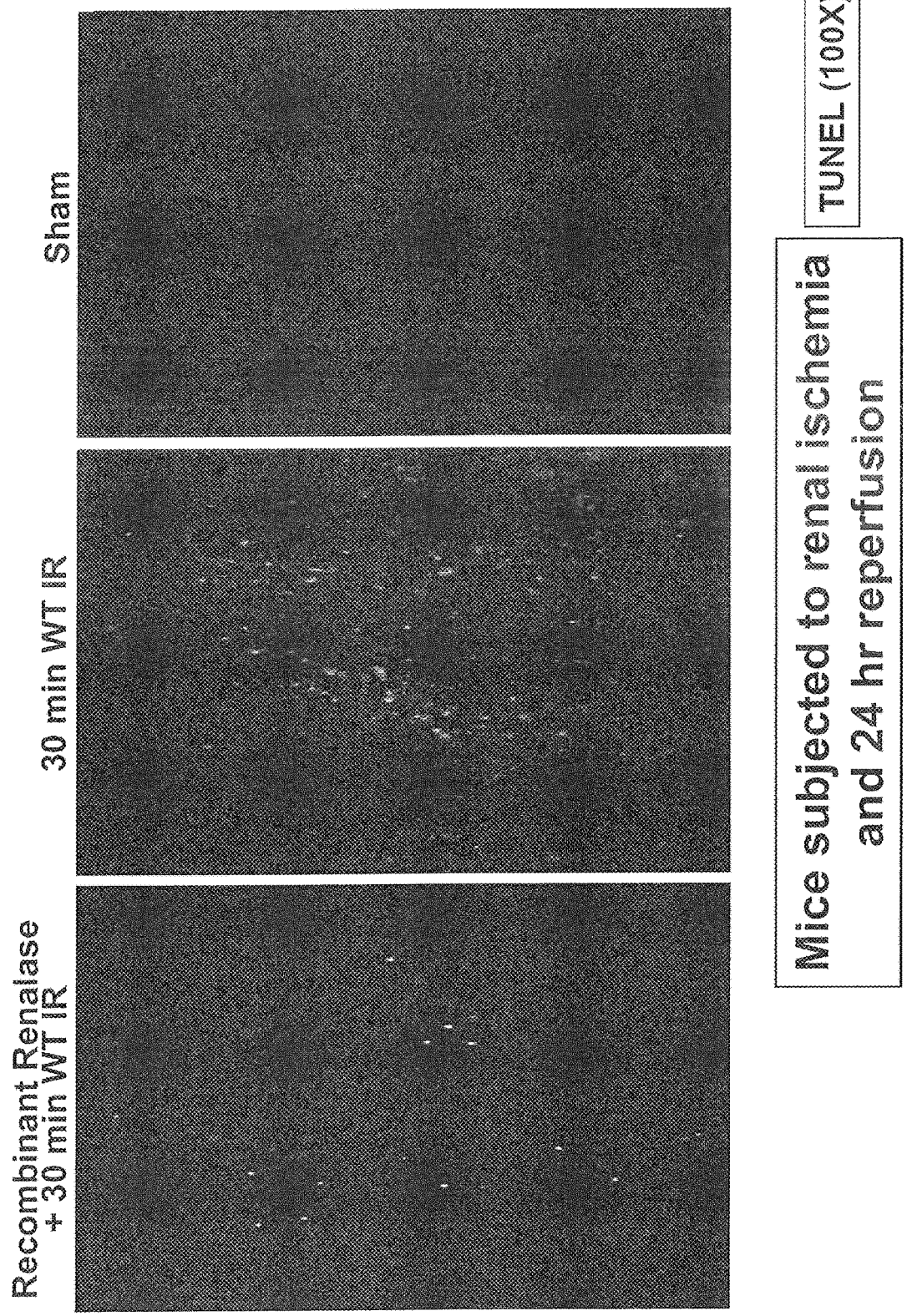

Exogenous Renalase Decreases Renal Apoptosis. Neutrophil Infiltration and Macrophage Infiltration after IR TUNEL staining detected apoptotic renal cells in kidney of mice subjected to renal IR with predominant proximal tubule cell apoptosis (FIG. 6A, magnification 100×, representative of 4 experiments). Unlike the kidneys of sham-operated mice, 30 min. of renal ischemia and 24 hr. of reperfusion resulted in severe apoptosis in the kidneys of vehicle (saline)-treated mice (FIG. 6A). Recombinant renalase (1.5 mg/kg, s.c.) given 10 min. before renal ischemia significantly reduced the number of apoptotic TUNEL-positive cells in the kidney (FIG. 6B, N=4).

Figure 7A:
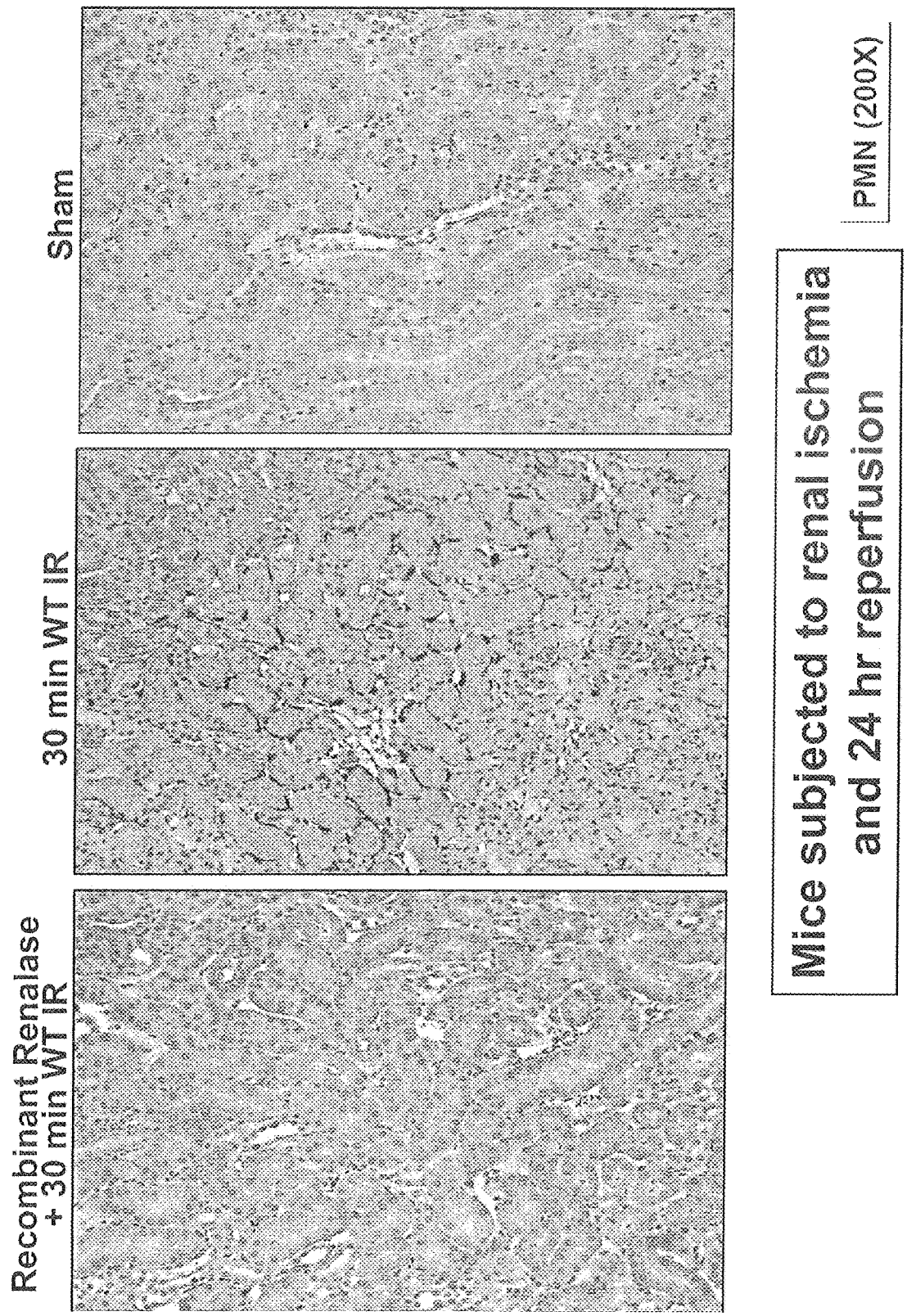
FIGS. 7A through 7D, is a set of images and graphs demonstrating that exogenous recombinant human renalase reduces renal neutrophil infiltration in mice after IR.
Figure 7B:
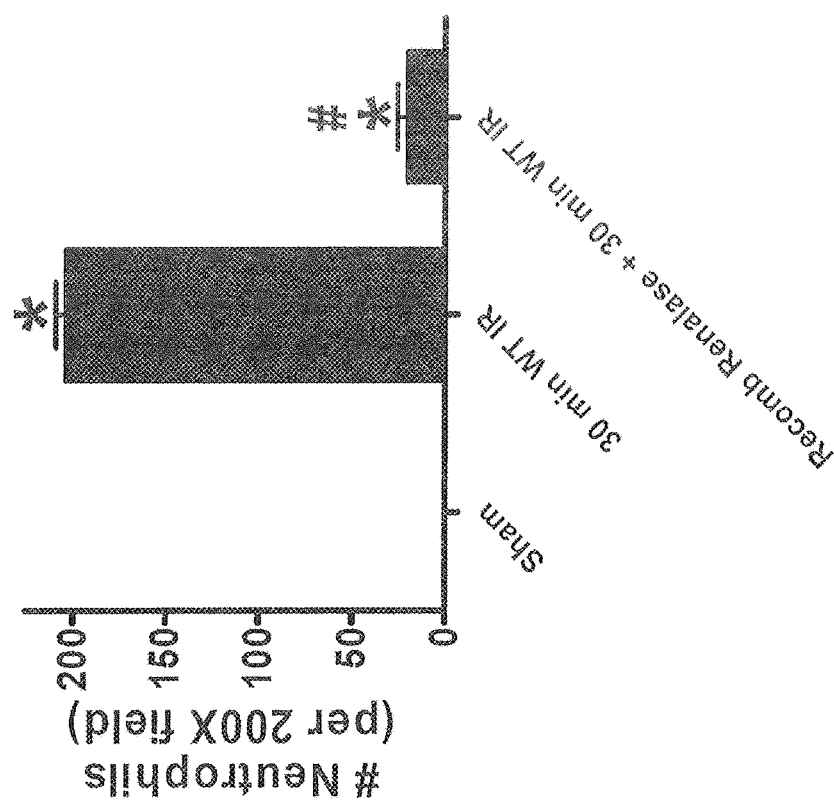
Figure 7C:
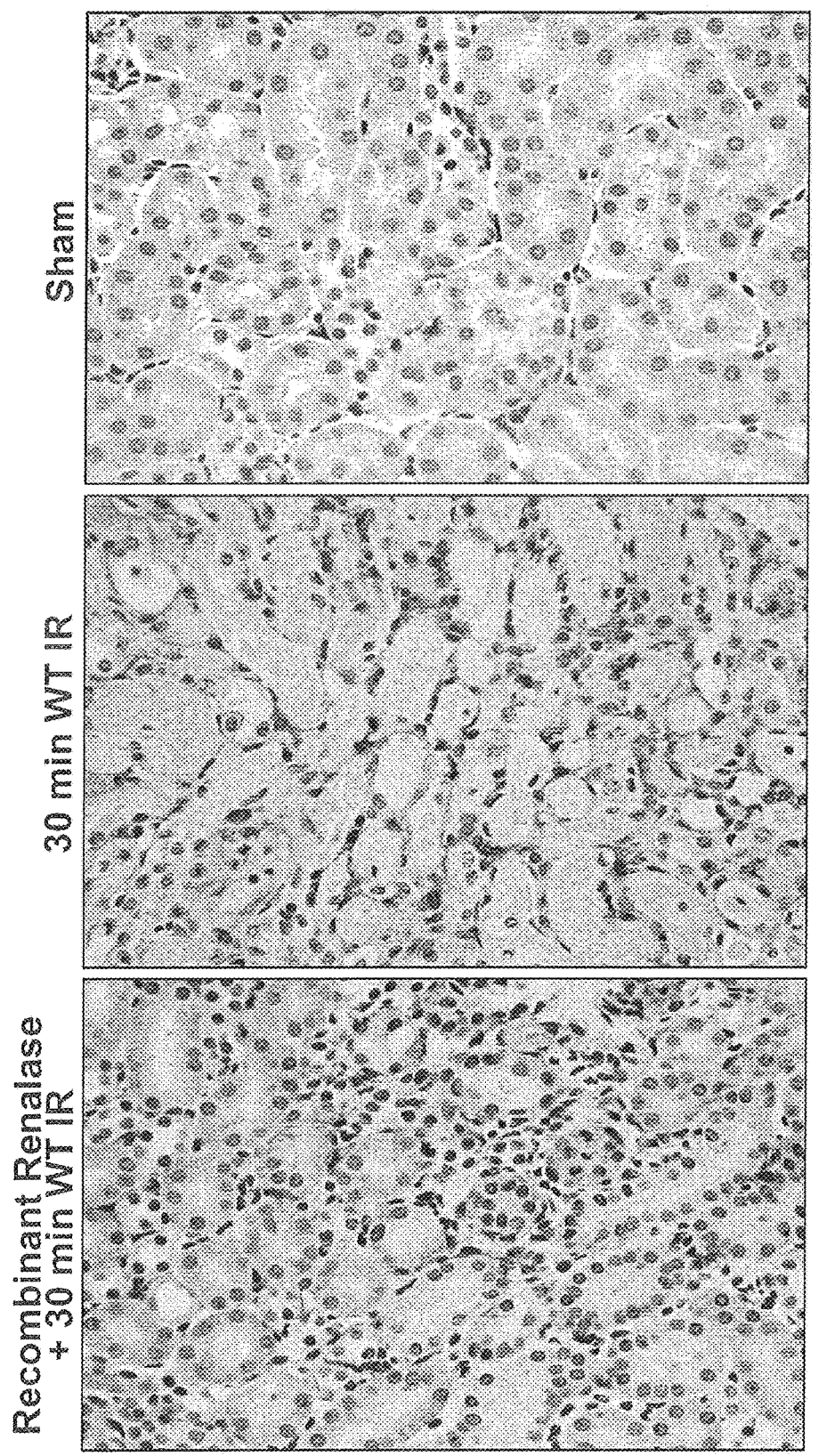
Figure 7D:
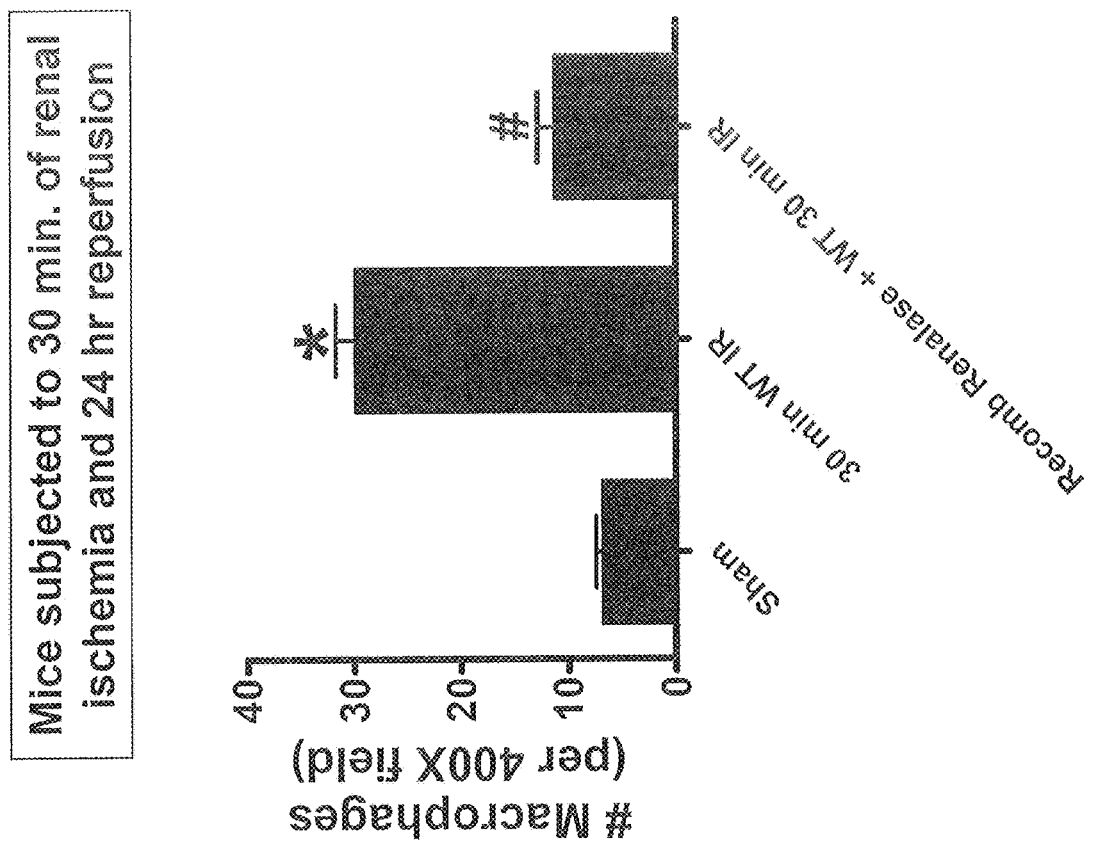

FIG. 7A shows representative images of neutrophil immunohistochemistry of kidneys (magnification 200×, representative of 4 experiments) from mice subjected to 30 min. of renal ischemia and 24 hr. reperfusion or to sham-operation. There was significant neutrophil infiltration in the kidneys of mice treated with saline and subjected to 24 hr. renal IR. In sham-operated mice, no neutrophils in the kidney were able to be detected. Mice treated with renalase before renal ischemia had significantly reduced number of neutrophils infiltrating the kidney after IR (FIG. 7B, N=4). FIG. 7C shows representative images of macrophage (F4/80) immunohistochemistry of kidneys (magnification 400×, representative of 3-4 experiments) from mice subjected to 30 min. of renal ischemia and 24 hr. reperfusion or to sham-operation. There was significantly increased macrophage infiltration (brown stain) in the kidneys of mice treated with saline and subjected to 24 hr. renal IR. Mice treated with recombinant renalase before renal ischemia had significantly reduced number of macrophages infiltrating the kidney after IR (FIG. 7D).

Figure 8A:
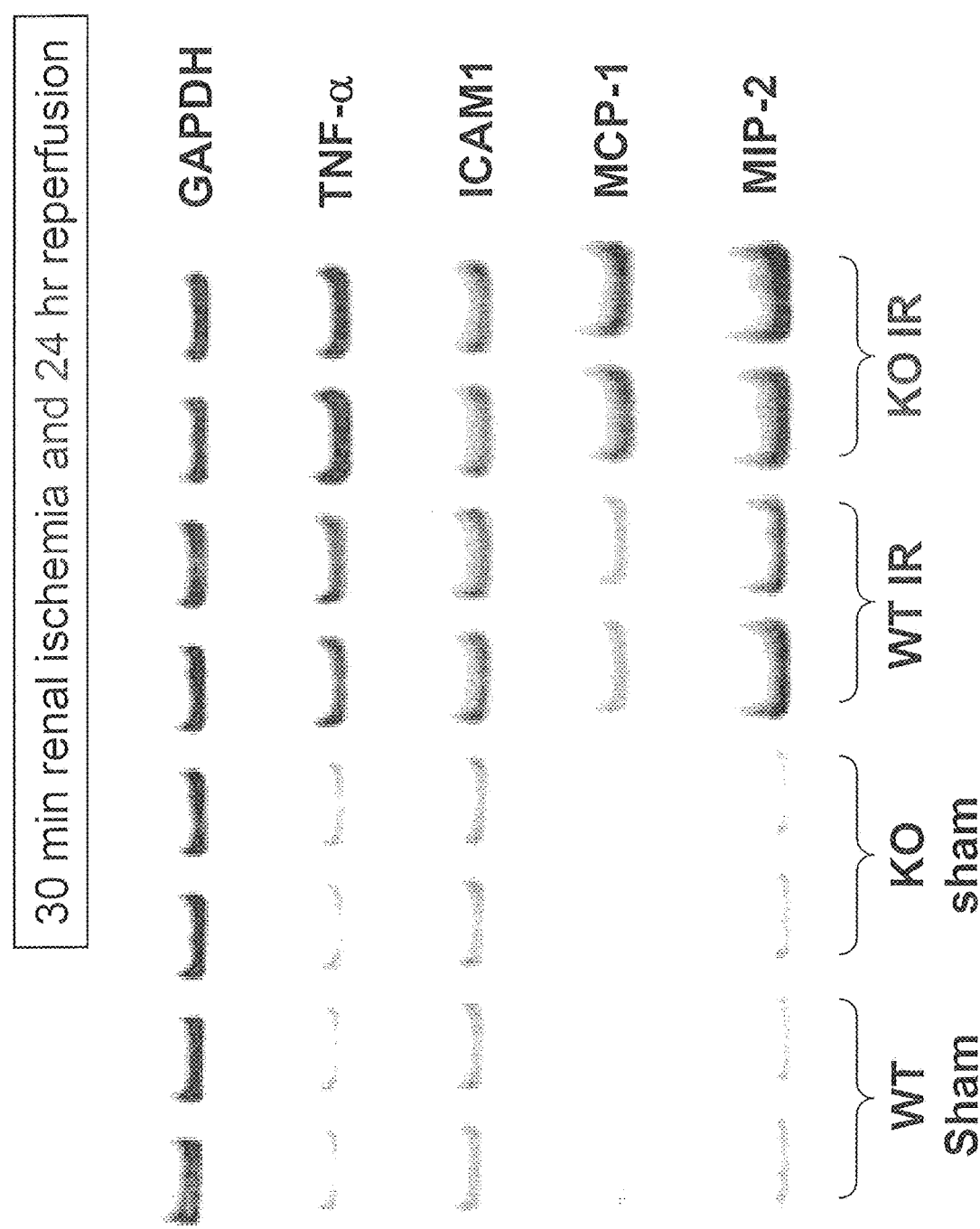
FIGS. 8A and 8B, is a set of images and graphs demonstrating that renalase deficiency increases pro-inflammatory gene expression in the kidney after IR.
Figure 8B:
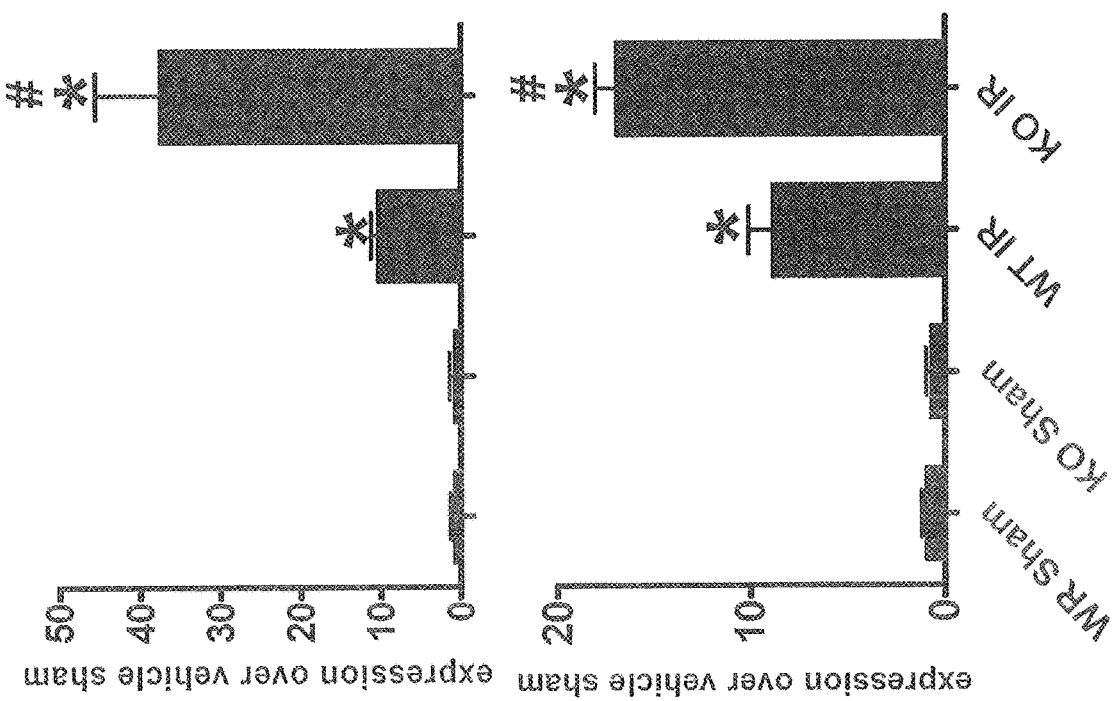
Figure 8B:
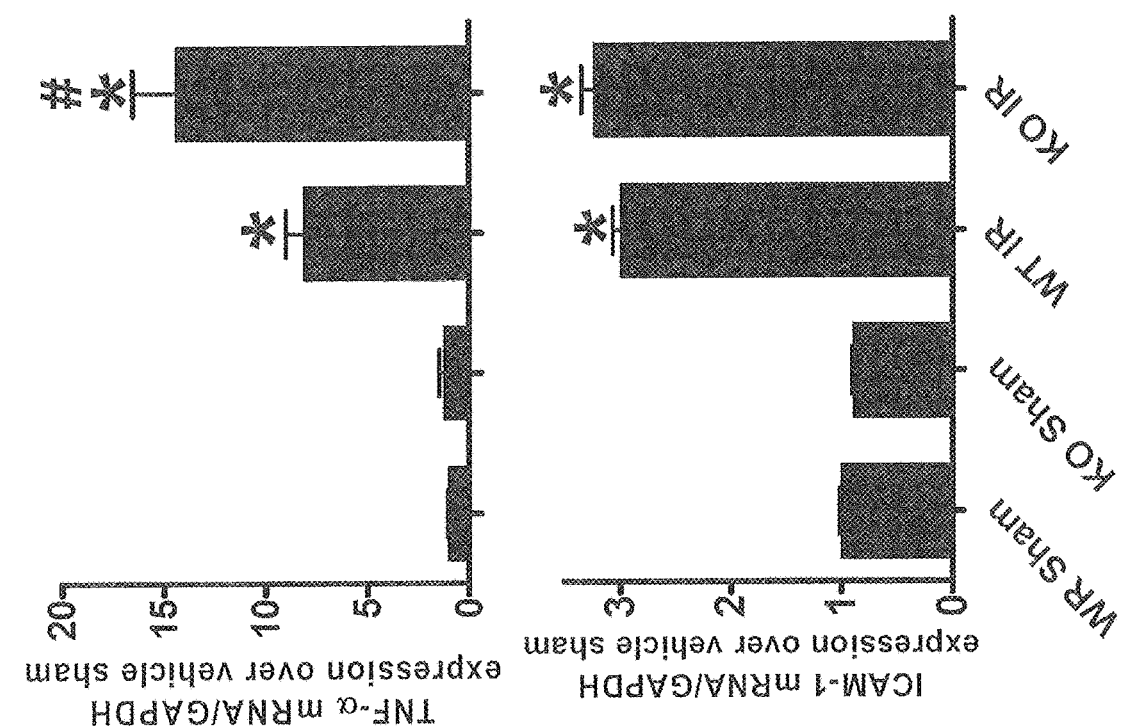

Renalase Deficiency Increases Pro-Inflammatory Gene Expression in the Kidney after IR The expression of pro-inflammatory cytokine mRNAs in the kidney was measured (TNF-α, ICAM-1, MCP-1 and MIP-2) 24 hr. after renal IR with RT-PCR (primer sequences listed in Table 1). Renalase WT mice significantly increased expression of all pro-inflammatory mRNAs examined compared to the sham-operated renalase WT mice (FIG. 8). Moreover, renalase deficient mice had even greater increases in TNF-α, MCP-1 and MIP-2 expression without any changes in ICAM-1 expression compared to renalase WT mice.

RP 220 - (SEQ ID NO: 3)
CIRFVSIDNKKRNIESSEIG

RP H220 - (SEQ ID NO: 4)
HHHHHHCIRFVSIDNKKRNIESSEIG

RP A220 - (SEQ ID NO: 5)
IRFVSIDNAAANIESSEIG

RP 220 SCRAMBLED - (SEQ ID NO: 6)
CSKRIFKVISSIEDNNERG

RP 128 - (SEQ ID NO: 7)
FRHRVTQINLRDDKWEVSKQ

RP 19 - (SEQ ID NO: 8)
LLRRQTSGPLYLAVWDKAED

Renalase (NP_001026879.2) - (SEQ ID NO: 9)
MAQVLIVGAGMTGSLCAALLRRQTSGPLYLAVWDKAEDSGGRMTTACSPH
NPQCTADLGAQYITCTPHYAKKHQRFYDELLAYGVLRPLSSPIEGMVMKE
GDCNFVAPQGISSIIKHYLKESGAEVYFRHRVTQINLRDDKWEVSKQTGS
PEQFDLIVLTMPVPEILQLQGDITTLISECQRQQLEAVSYSSRYALGLFY
EAGTKIDVPWAGQYITSNPCIRFVSIDNKKRNIESSEIGPSLVIHTTVPF
GVTYLEHSIEDVQELVFQQLENILPGLPQPIATKCQKWRHSQVTNAAANC
PGQMTLHHKPFLACGGDGFTQSNFDGCITSALCVLEALKNYI

TABLE 1

Primers used to amplify cDNAs based on published GenBank sequences for mice

| Primers | Accession Number | Sequence (Sense/Antisense) | SEQ ID NO | Product Size (bp) | Cycle Number | Annealing Temperature (° C.) |
|---|---|---|---|---|---|---|
| TNF-a | X02611 | 5'-TACTGAACTTCGGGGTGATTGGTCC-3'<br>5'-CAGCCTTGTCCCTTGAAGAGAACC-3' | (SEQ ID NO: 11)<br>(SEQ ID NO: 12) | 290 | 24 | 65 |
| ICAM-1 | X52264 | 5'-TGTTTCCTGCCTCTGAAGC-3'<br>5'-CTTCGTTTGTGATCCTCCG-3' | (SEQ ID NO: 13)<br>(SEQ ID NO: 14) | 409 | 21 | 60 |
| MCP-1 | NM_011333 | 5'-ACCTGCTGCTACTCATTCAC-3'<br>5'-TTGAGGTGGTTGTGGAAAAG-3' | (SEQ ID NO: 15)<br>(SEQ ID NO: 16) | 312 | 22 | 60 |
| MIP-2 | X53798 | 5'-CCAAGGGTTGACTTCAAGAAC-3'<br>5'-AGCGAGGCACATCAGGTACG-3' | (SEQ ID NO: 17)<br>(SEQ ID NO: 18) | 282 | 22 | 60 |
| Renalase | NC_000085.6 | 5'-TGACCTTGTCATCCTCACCA-3'<br>5'-AACTCCAAATGGGACAGTGG-3' | (SEQ ID NO: 19)<br>(SEQ ID NO: 20) | 295 | 28 | 65 |
| GAPDH | M32599 | 5'-ACCACAGTCCATGCCATCAC-3'<br>5'-CACCACCCTGTTGCTGTAGCC-3' | (SEQ ID NO: 21)<br>(SEQ ID NO: 22) | 450 | 15 | 65 |

Example 2: Protective Effect of Renalase and Renalase Peptides in AKI and Acute Cellular Injury Renalase Polypeptide and Peptide Sequences

RP 224 - (SEQ ID NO: 2)
CVSIDNKKRNI

Renalase (NP_060833.1) - (SEQ ID NO: 10)
MAQVLIVGAGMTGSLCAALLRRQTSGPLYLAVWDKAEDSGGRMTTACSPH
NPQCTADLGAQYITCTPHYAKKHQRFYDELLAYGVLRPLSSPIEGMVMKE
GDCNFVAPQGISSIIKHYLKESGAEVYFRHRVTQINLRDDKWEVSKQTGS
PEQFDLIVLTMPVPEILQLQGDITTLISECQRQQLEAVSYSSRYALGLFY

```
-continued
EAGTKIDVPWAGQYITSNPCIRFVSIDNKKRNIESSEIGPSLVIHTTVPF

GVTYLEHSIEDVQELVFQQLENILPGLPQPIATKCQKWRHSQVPSAGVIL

GCAKSPWMMAIGFPI
```

Protective Effect of Recombinant Renalase in Ischemic and Toxic AKI

Experiments were performed to assess whether ischemic AKI in mice leads to renalase deficiency and whether renalase deficiency directly exacerbates ischemic AKI. Thus, experiments were performed to test whether 1) ischemic AKI leads to reduced kidney and plasma renalase levels, 2) ischemic AKI-induced renalase deficiency leads to elevated plasma catecholamine (norepinephrine) levels, 3) renalase deficient mice exhibit increased renal IR injury and 4) exogenous administration of recombinant human renalase directly protects against ischemic AKI in mice.

In the studies described herein, it was found that administration of recombinant human renalase reduced plasma catecholamine levels and ameliorated ischemic acute kidney injury in renalase wild type mice by reducing renal tubular necrosis, inflammation and apoptosis. Taken together, these data show that renalase serves to protect against ischemic acute kidney injury by reducing renal tubular necrosis, apoptosis and inflammation.

Renalase Protects Against Cisplatin-Mediated AKI in Mice

Figure 9:
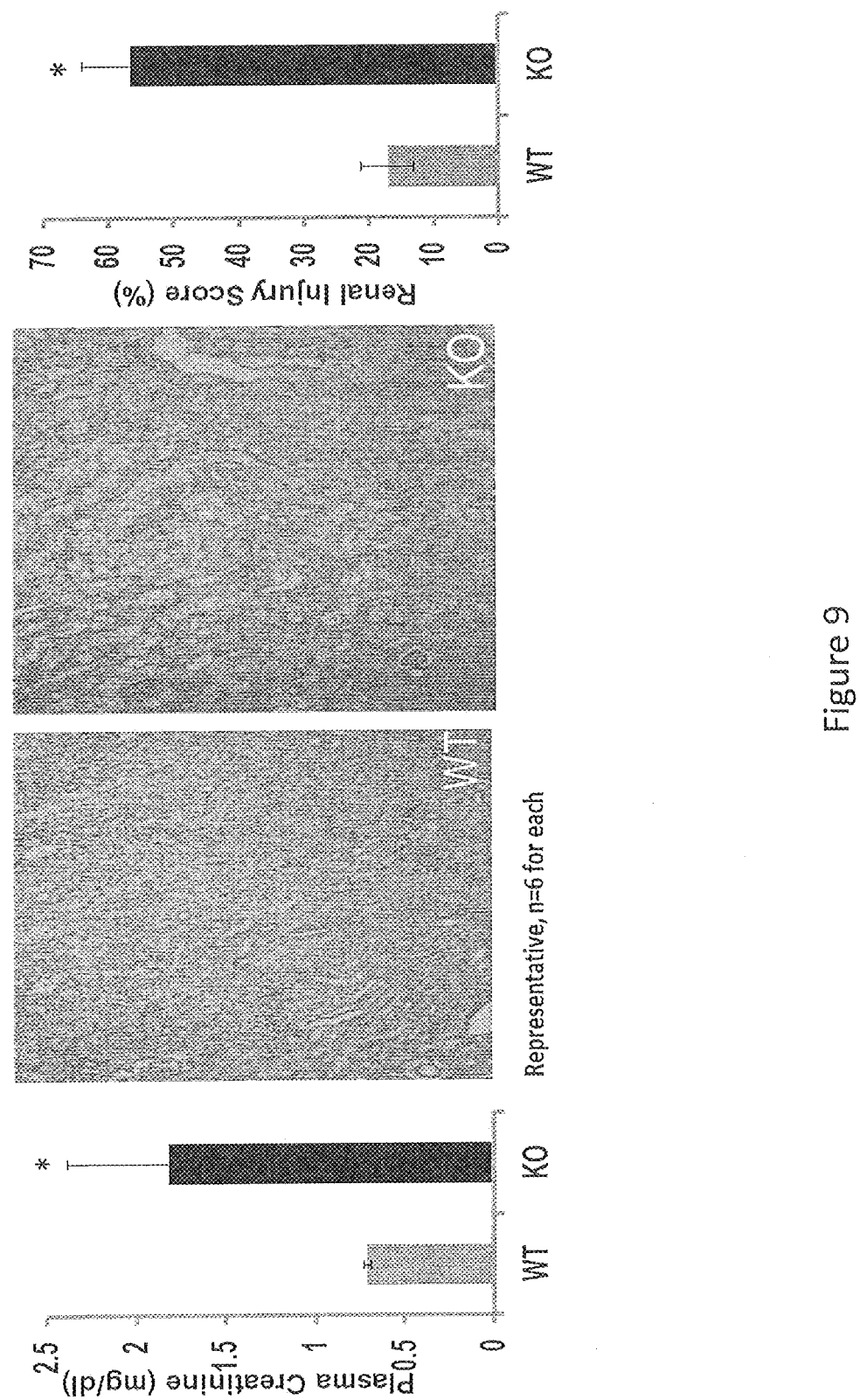
FIG. 9, is a set of graphs and images showing that three days post-treatment with cisplatin, plasma creatinine was significantly higher in renalase KO mice compared to WT (1.82 0.56 vs. 0.71 0.02 mg/dl, n=6, P=0.021), as was the renal injury score (KO=56.62 7.38%, n=6, vs. WT=17.07 4.03, n=5; p<0.0002). The degree of apoptosis (2 fold increase in TUNEL staining, p<0.005), and macrophage infiltration (35% increase in F4/80 staining, p<0.05). These data show that renalase protects against cisplatin AKI by decreasing pro-apoptotic, and increasing pro-survival signals. Renalase could provide a useful therapeutic option for cisplatin AKI.

The efficacy of recombinant renalase in treating cisplatin-induced AKI was investigated, and the mechanisms that mediate its protective action were assessed. Cisplatin (20 mg/kg) was administered by intra-peritoneal injection to either WT or renalase KO mice. The mice were sacrificed 3 days later. Blood was collected for BUN and creatinine measurements, and kidneys harvested for histologic examination, immunofluorescence (IF), and western blotting (WB). One renal pathologist, masked to the identity of the study animal, reviewed each kidney specimen. Pathologic features were scored using an ordinal rating scale (0-4; 0=none; 1=<25%, 2=26-50%; 3=51-75%; 4=76-100%) for the presence of tubular necrosis. Morphometry of renal cortex and medulla was performed using point counting technique. Points falling on injured tubules, were counted and the percentage of lesion area was calculated as percentage of total points counted As shown in FIG. 9, three days post treatment with cisplatin, plasma creatinine was significantly higher in renalase KO mice compared to WT ($1.82 \pm 0.56$ vs. $0.71 \pm 0.02$ mg/dl, n=6, P=0.021), as was the renal injury score (KO=$56.62 \pm 7.38\%$, n=6, vs. WT=$17.07 \pm 4.03$, n=5; p<0.0002), the degree of apoptosis (2-fold increase in TUNEL staining, p<0.005), and macrophage infiltration (35% increase in F4/80 staining, p<0.05). These data show that renalase protects against cisplatin AKI by decreasing pro-apoptotic signals, and increasing pro-survival signals. Thus, renalase is a useful compound for the treatment of cisplatin AKI.

Renalase has Direct Cellular Effect in Protection Against AKI

Figure 10:
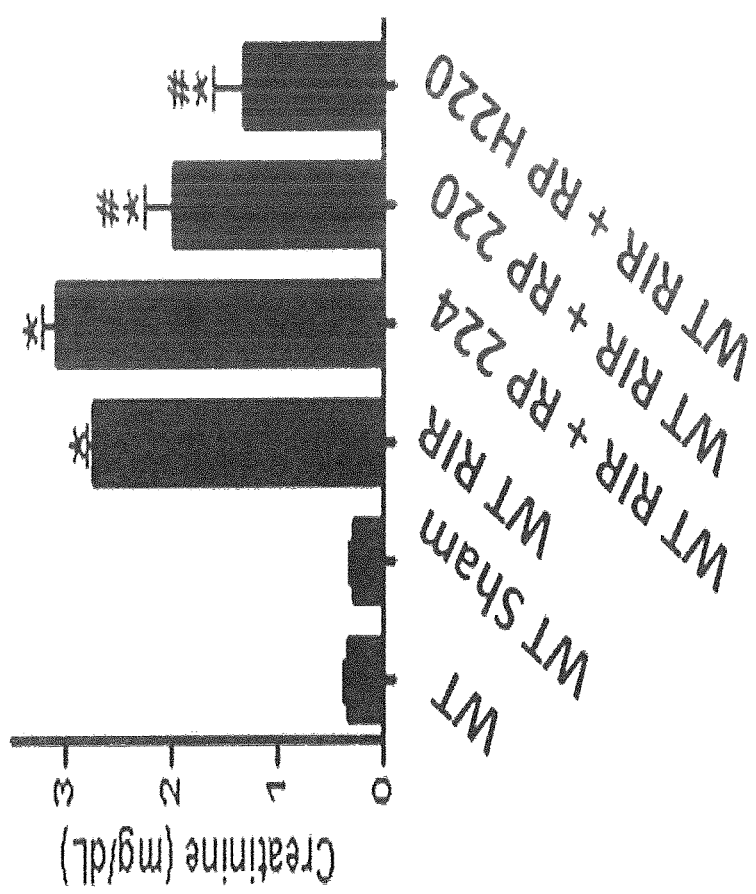
FIG. 10 is a graph showing renalase peptide protects against ischemic AKI. Change in plasma creatinine at 24 hrs in WT mice subjected to 30 min. of renal ischemia with and without pretreatment with indicated renalase peptides.

The addition of exogenous renalase to cisplatin-treated HK-2 cells inhibited caspase-3 activation, and increased Bcl-2 expression, and cell survival, suggesting that renalase's in vivo protective effect may not be mediated solely by a reduction in circulating catecholamines. Examination of the crystal structure of renalase and in vitro studies using antipeptide monoclonal antibodies led to identification of a highly conserved renalase peptide (RP H220, 26 aa), which had no detectable NADH or amine oxidase activity, but protected against ischemia (100 µg given subcutaneously 30 min. prior), and cisplatin-mediated AKI in mice (creatinine measured by HPLC: Sham: $0.05 \pm 0.002$, cisplatin: $0.177 \pm 0.02$, cisplatin +RP H220; $0.085 \pm 0.007$, n=3, p=0.012) (FIG. 10). A shorter but related peptide (RP 220, 20 aa) was less effective, while the shortest related peptide tested (RP 224, 10 aa) was not protective. Thus, RP H220 and RP 220 are useful compounds for the prevention and treatment of AKI.

Renalase and RP H220 Protects Human Proximal Tubular (HK-2) Cells Against Cisplatin- and Oxidant-Mediated Injury In cultured human proximal tubule epithelial (HK-2) cells, recombinant renalase (10 µg/ml) significantly reduced necrosis induced with 2 mM $H_2O_2$ (LDH released at 6 hr=$28 \pm 2\%$, N=3) compared to vehicle-treated HK-2 cells subjected to $H_2O_2$ necrosis (LDH=$47 \pm 3\%$, N=3, p<0.01). Similar results were obtained with RP H220.

Figure 11:
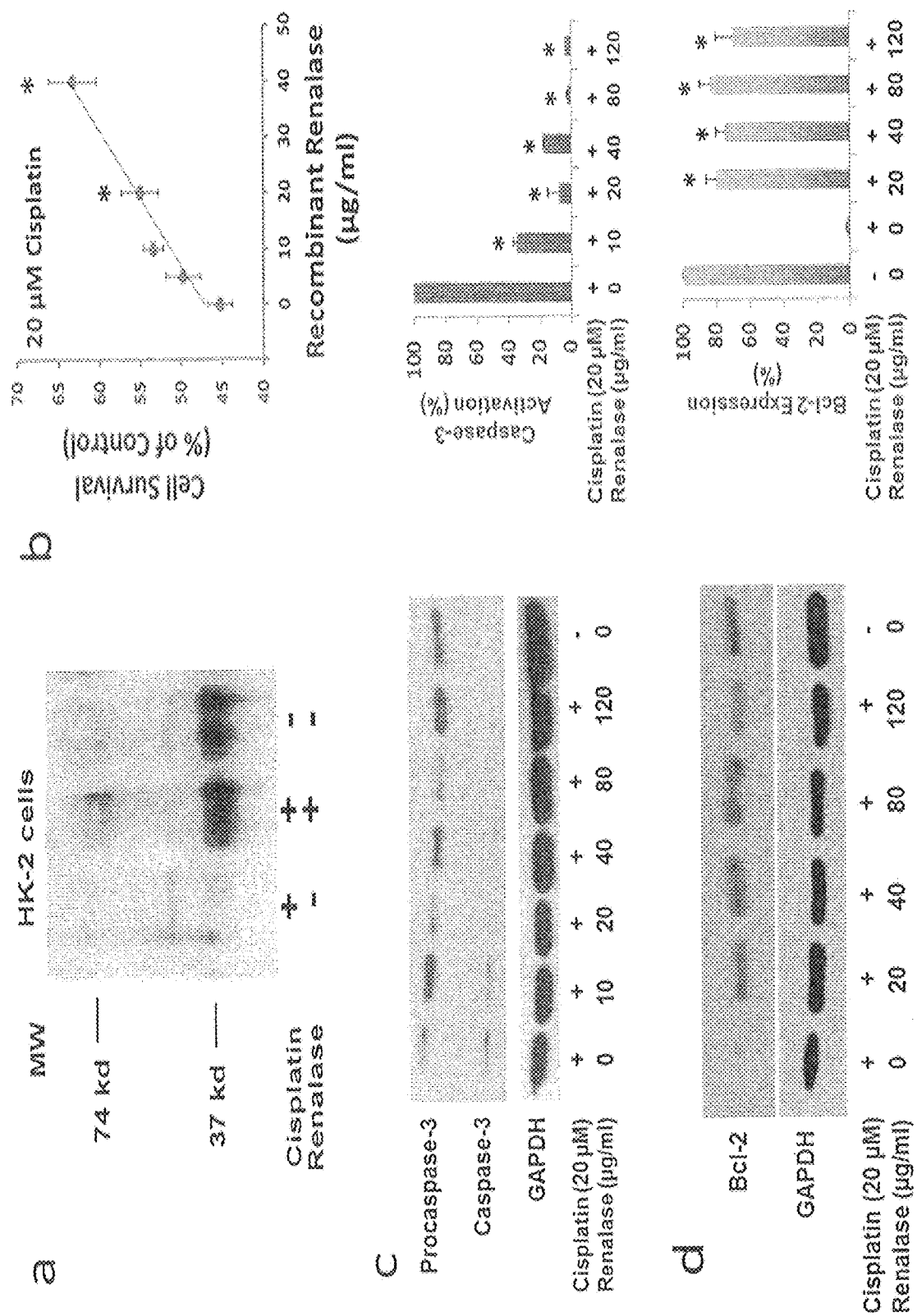
FIG. 11, comprising

Cultured HK-2 cells were incubated with 20 µM cisplatin for 24 hours with and without recombinant renalase. Renalase expression was examined by Western blot and cell viability (mitochondrial integrity) was determined spectrophotometrically using WST-1, a tetrazolium salt that is cleaved, by mitochondrial dehydrogenases of metabolically active and viable cells, to formazan (420-480 nm) (Boehringer Mannheim, Germany). As shown in FIG. 11A, HK2 cells exposed to cisplatin for 24 hours showed a marked reduction in renalase expression. The addition of recombinant renalase not only restored cellular renalase expression but also provided significant protection against cisplatin toxicity, increased cell viability by ~50% (FIG. 11B), decreased caspase-3 activation (FIG. 11C), and increased Bcl-2 expression (FIG. 11D). Similar results were obtained with RP H220.

Renalase and RP 220 Signal Through the PI3K/AKT and MAPK Pathways

Figure 12:
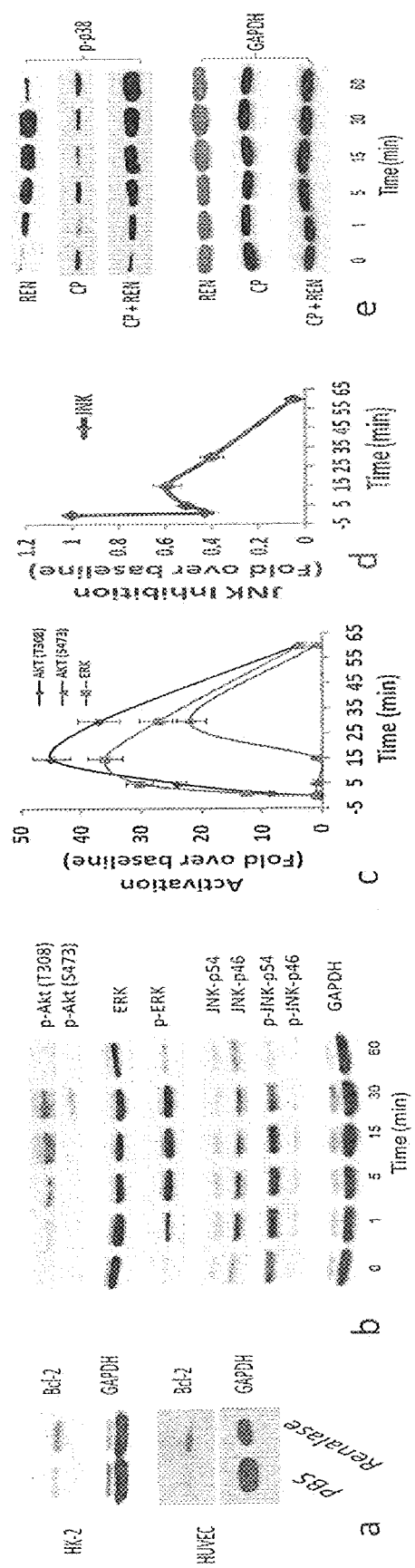
FIG. 12, comprising

Since RP H220 has neither detectable oxidase activity, nor significant effect on systemic blood pressure, and yet protects against ischemic and toxic AKI in mice, whether renalase's protective effect was in part mediated by a direct cellular effect was assessed. Preliminary results indicate that renalase upregulates Bcl-2 expression in HK-2 and human vein endothelial cells (HUVEC) at 24 hrs (FIG. 12A), and signals through the PI3K/AKT pathway by activating AKT (~45 fold at 15 min), and the MAPK pathway by activating ERK (~35 fold at 15 min) and down-regulates JNK (~95% decrease in JNK-p54/p46 phosphorylation) (FIGS. 12B, 12C, and 12D). In cells treated with cisplatin, renalase caused marked and sustained activation of AKT (not shown) and p38 (FIG. 12E). Similar results were obtained with RP H220 but not with scrambled RP H220. AKT has been shown to promote cell survival by growth factors against several apoptotic stimuli, and Bcl-2 upregulation has been identified as a critical mechanism.

Hemodynamics Effects of RenPep1

Figure 14:
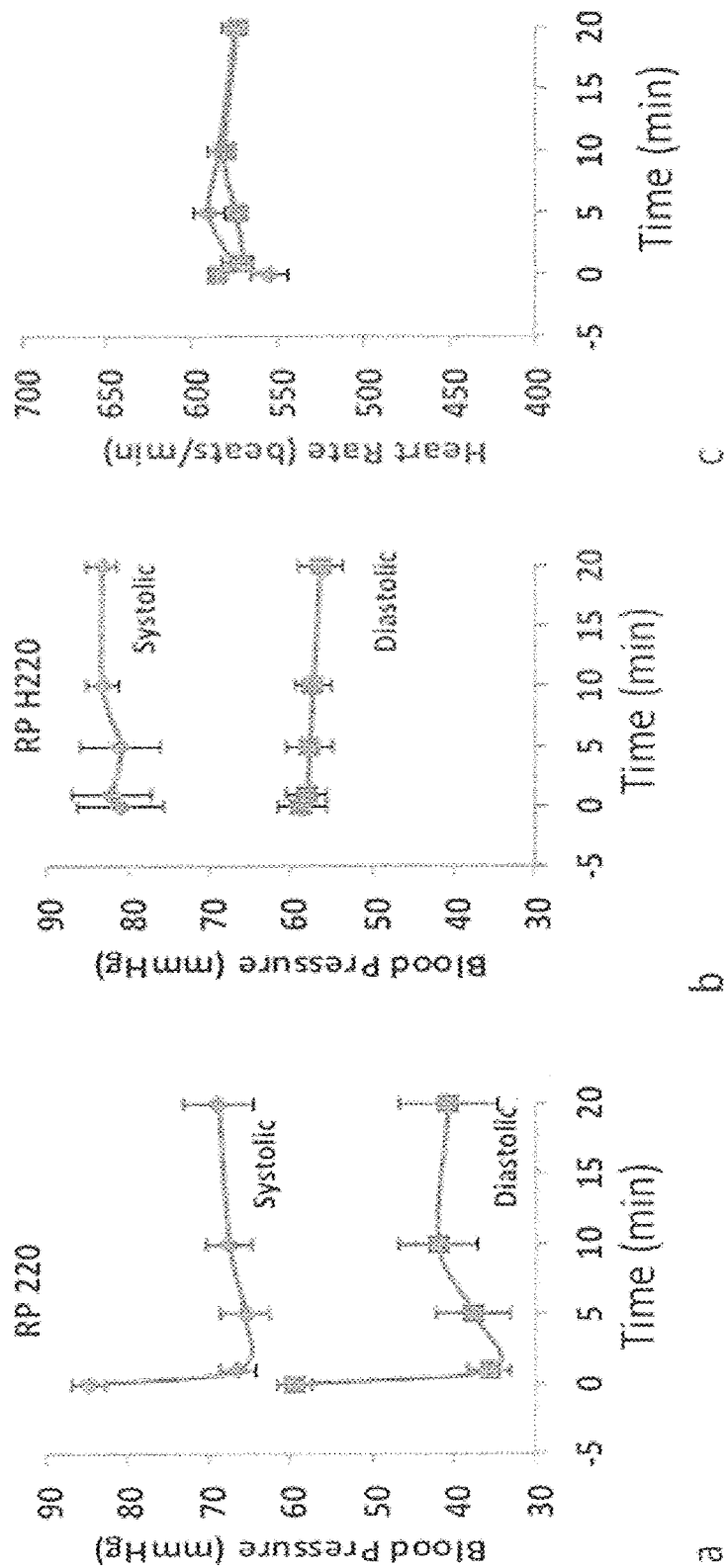
FIG. 14, comprising

The effect of 7 different renalase peptides (FIG. 13) on systemic blood pressure was examined and found that both IV and subcutaneous administration of RP 220 administration had a marked and sustained effect on systemic blood pressure (FIG. 14A). The effect was specific for RP 220 since none of the other peptides tested had any measurable effect on BP.

Figure 15:
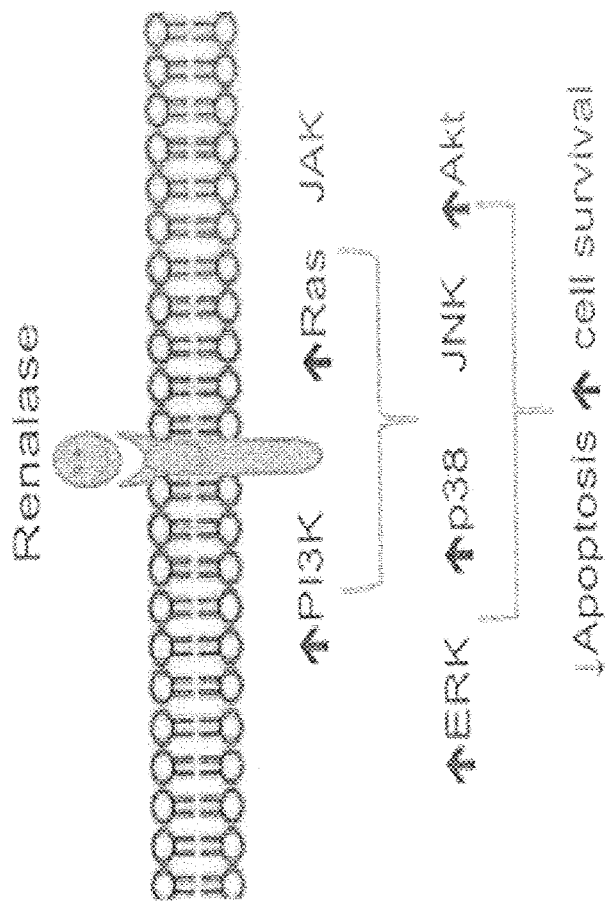
FIG. 15 is a diagram depicts a working model of renalase. Renalase binds to membrane receptor to activate cell signaling pathways which affect cell survival. Hemodynamic effect of recombinant renalase or RP 220 may be mediated by the same receptor that activates cell signaling or by a different receptor.

Renalase mediates its physiological effects through a receptor-mediated mechanism (See FIG. 15). Renalase peptides RP 220 and RP H220 are useful compounds for treating and preventing ischemic and toxic AKI. RP 220 is a potent hypotensive agent and is useful for treating and preventing hypertension and other cardiovascular conditions, such as congestive heart failure.

Example 3: Acute Renal Ischemia Decreases Urinary Renalase Secretion

Figure 16:
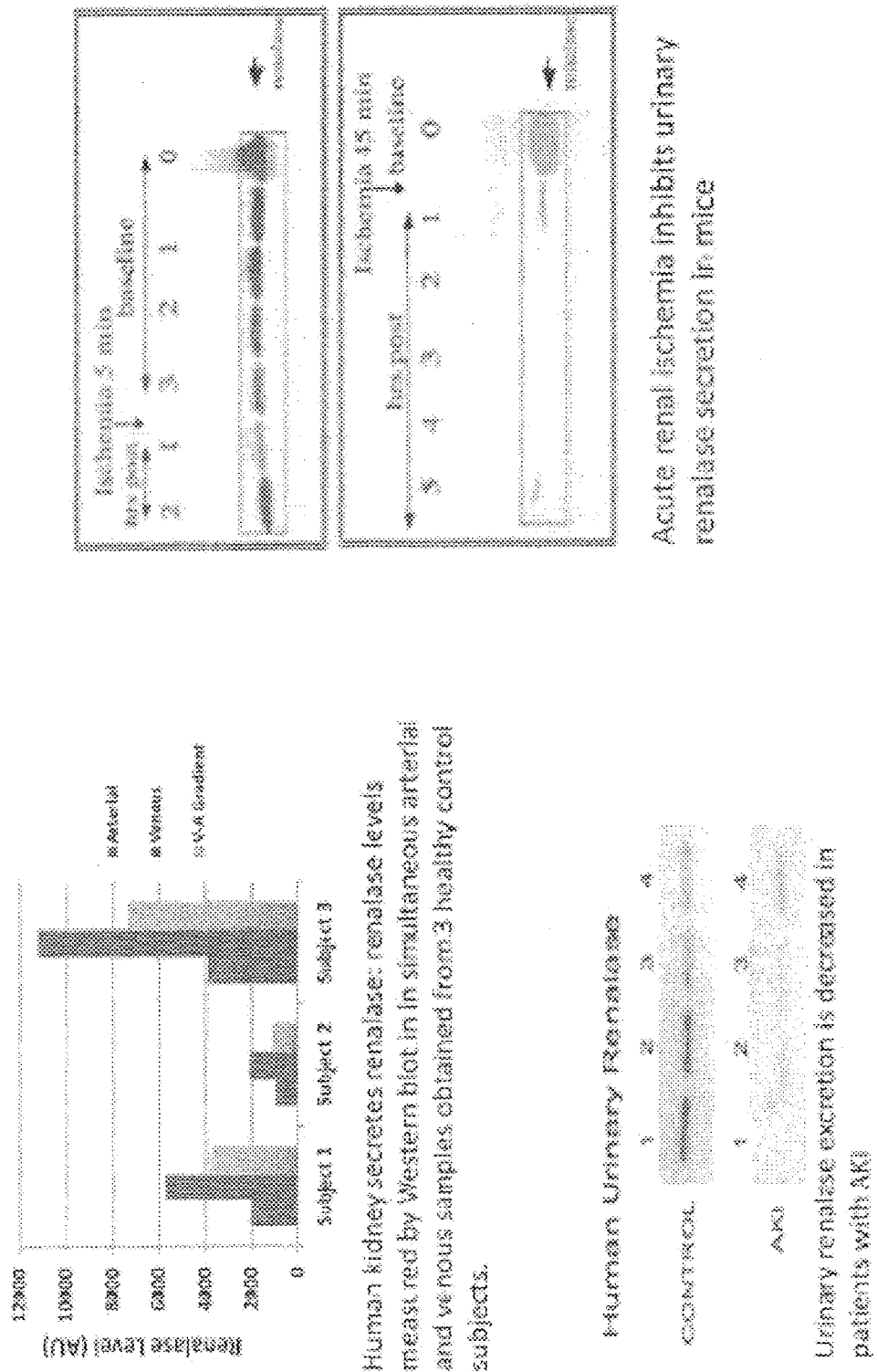
FIG. 16 depicts the results of experiments demonstrating that acute renal ischemia results in a decrease in kidney secretion of renalase, which can be detected as a decrease in renalase level in blood, serum, plasma and urine.

Experiments were conducted demonstrating that acute renal ischemia results in a decrease in kidney secretion of renalase, which can be detected as a decrease in renalase level in blood, serum, plasma and urine (FIG. 16).

Example 4: Renalase Lowers Blood Pressure and Protects Against Acute Kidney Injury Via a Receptor-Mediated Mechanism that is Independent of Catecholamine Metabolism The data described herein demonstrate that renalase and renalase peptides devoid of amine oxidase activity, signal via the AKT and MAPK pathways, and that the peptides fully mimic the cytoprotective and hemodynamic actions of recombinant renalase.

Recombinant renalase protein, synthesized as a GST fusion protein in *E Coli*, has been show to possess amine oxidase activity, and to metabolize epinephrine, norepinephrine and dopamine in vitro. Recombinant renalase protein caused a marked decrease in blood pressure when injected into rodents (Xu et al., 2005, J Clin Invest 115:1275-1280). It was subsequently shown recombinant renalase required NAD(P)H for full activity, and the rate of epinephrine (renalase's preferred substrate) metabolism increased 18 fold in the presence of NADH.

Renalase isoforms 3-7 lack large portions of the putative amine oxidase domain, are significantly shorter than isoforms 1 and 2, and are unlikely to possess oxidase activity. RP-220 is conserved in all renalase isoforms, including the shortest isoform 7 which lacks the first 4 exons. Isoform 1 and RP-220 signal rapidly through the PI3K and MAPK pathways to activate AKT, ERK and p38, which is consistent with the explanation that they both act by binding to a specific cell surface receptor. AKT and ERK activation is generally protective in ischemic AKI (Arany and Safirstein, 2003, Semin Nephrol 23:460-464). Pharmacological inhibition of both AKT and ERK abrogated the RP-220's protective effect against ischemic AKI confirming their protective role in ischemic injury.

As is the case in ischemic cardiac injury and ischemic AKI, renalase deficiency aggravates cisplatin AKI. Renalase and RP-H220 protect against cisplatin AKI. In this sense, renalase, and the peptides derived from it, act as general survival factors interdicting pathways that lead to cell death under stress. Principal among those pathways are the MAPKs and AKT (Safirstein, 2004, Int Suppl:S62-66; Arany and Safirstein, 2003, Semin Nephrol 23:460-464). By shifting the balance between ERK and JNK activation toward greater activation of ERK and AKT, cells can resist oxidant, or toxic exposure (Arany et al., 2004, Kidney Int. 65:1231-1239; Arany et al., 2004, American Journal of Physiology: Renal Physiology 287:F543-549; Pabla and Dong, 2008, Kidney Int 73:994-1007). Cisplatin-induced cell death is EGFR/Src/ERK signaling dependent in mouse proximal tubule cells. It would appear that renalase and its derived active peptides engage these pathways in a way quite similar to other peptides more classically associated with growth and survival under stress.

RP-H220 was more effective than RP-220 against ischemic AKI. Although no difference in the signaling patterns of the two peptides in HK-2 cells was detected, it is possible that subtle differences exist in the overall pattern of AKT and MAPK signaling, accounting for the greater efficacy of RP-H220 in ischemic AK. An alternative and perhaps more likely explanation for the difference in the protective effects of RP-220 and RP-H220 is the marked difference in their hemodynamic effects. RP-220 reduces blood pressure while RP-H220 does not. The hypotension induced by RP-220 would compromise renal blood flow and partially counteract its cytoprotective effect.

As described herein, both RP-220 and RP-H220 are cytoprotective, but only RP-220 decreases blood pressure. These observations are consistent with the explanation that the two peptides could bind to a single renalase receptor with different signaling patterns. Alternatively, they could bind to two different, but related receptors. The rapid fall in blood pressure suggests that RP-220 causes peripheral vasodilatation. Pharmacological inhibition of the D1 like receptor had no effect on the hypotensive response to RP-220, consistent with the explanation that the dopamine receptor does not play a role in mediating RP-220's hemodynamic effect.

While not wishing to be bound by any particular theory, the results described herein are consistent with the explanation that RP-220 decreases blood pressure by interacting with a previously characterized G-coupled receptor protein (GPCR), a receptor guanylyl cyclase (RGC), or one of the orphan GPCRs and RGCs.

The described herein demonstrate a critical region of renalase molecule that mediates its cytoprotective and hemodynamic effects. Furthermore, it is shown that these two effects can be dissociated. Finally, renalase is shown to protect against toxic and ischemic injury and to lower blood pressure not by its amine oxidase property, but rather by its interaction with an as yet unidentified receptor that activates intracellular signaling in a manner that promotes cell survival.

The methods and materials used in this example are now described.

Synthesis and Analysis of Recombinant Human Renalase and Renalase Peptides

Human recombinant renalase was synthesized as described (Desir et al., 2012, J Am Heart Assoc. 1:e002634). Renalase peptides were acetylated at the amino terminus and purified to 98% homogeneity (United Peptides, Herndon, Va.). Renalase enzymatic activity was measured as previously described (Desir et al., 2012, J Am Heart Assoc. 1:e002634). Renalase expression was detected using an anti-renalase monoclonal antibody generated against the renalase peptide RP-220 (amino acid 220-239 of hRenalase1) (Desir et al., 2012, J Am Heart Assoc. 1:e002634).

Murine Model of Cisplatin AKI

Cisplatin (15-20 mg/kg) was administered by intraperitoneal injection (IP) to either WT or renalase KO mice under brief isoflurane anesthesia. The animals were sacrificed 3 days later. Blood was collected for BUN and creatinine measurements, and kidneys harvested for histologic examination, immunofluorescence (IF), and western blotting (WB). One renal pathologist, masked to the identity of the study animal, reviewed each kidney specimen. Pathologic features were scored using an ordinal rating scale (0-4; 0=none; 1=<25%, 2=26-50%; 3=51-75%; 4=76-100%) for the presence of tubular necrosis. Morphometry of renal cortex and medulla was performed using the point counting technique. Points falling on injured tubules were counted, and the percentage of lesion area was calculated as percentage of total points counted.

Murine Model of Renal Ischemia Reperfusion (IR) Injury

After animal care and use committee approval, adult male C57BL/6 (Harlan Labs, Indianapolis, Ind.) were subjected to sham-operation or to 30 minutes of renal ischemia followed by 24 hrs of reperfusion as previously described (Lee et al., 2004, American journal of physiology. Renal physiology 286:F298-306). To test the renal protective effects of renalase peptides (RP-220, RP-H220 and RP-224), mice were pretreated with saline (vehicle) or with renalase peptides (100 µg subcutaneous) 10 to 30 minutes prior to renal ischemia.

In Vitro Model of Cisplatin and Hydrogen Peroxide Toxicity

HK2 cells (human proximal tubular line) obtained from ATTC (Manassas, Va., USA) were cultured in DMEM/F12 supplemented with glutamine, 10% FBS and antibiotics, and were maintained at 37° C. in 5% CO2. Cells were exposed to cisplatin (20 µM) in the presence or absence of renalase for 24 hrs, and cell viability was assessed by the WST1 method (Roche Applied Science, Germany). Cells were then harvested in RIPA buffer (20 mM Tris-HCl pH 7.5, 150 mM NaCl, 1 mM Na2EDTA, 1 mM EGTA, 1% NP-40, 1% sodium deoxycholate, 2.5 mM sodium pyrophosphate, 1 mM β-glycerophosphate, 1 mM Na3VO4, 1 µg/ml leupeptin) supplemented with a protease and phosphatase inhibitor cocktail (Roche Applied Science, Germany). Proteins were separated by SDS-PAGE and Western blotting was carried out using the following antibodies: anti-renalase monoclonal (Desir et al., 2012, J Am Heart Assoc. 1:e002634; (Lee et al., 2013, J Am Soc Nephrol 24:445-455); anti caspase 3 (Cell Signaling Technology, MA, USA) and anti Bcl2 (Thermo Scientific, USA). Necrotic injury in HK-2 cells (ATCC, Manassas, Va.) was induced with exposure to 2 mM $H_2O_2$ for 2-8 hr and lactate dehydrogenase (LDH) released into cell culture media was measured as described using a commercial LDH assay kit (Promega, Madison, Wis.) (Lee and Emala, 2002, American journal of physiology. Renal physiology 282:F844-852).

Measurement of Renal Function

Blood was collected from mice anesthetized with isoflurane via cardiac puncture into a heparinized syringe and was subsequently centrifuged to separate plasma. Samples were submitted to the Yale O'Brien Kidney Center for measurement of BUN and creatinine. Plasma creatinine was measured either by an enzymatic creatinine reagent kit according to the manufacturer's instructions (Thermo Fisher Scientific, Waltham, Mass.) or by HPLC. These methods of creatinine measurement largely eliminate the interferences from mouse plasma chromagens, known to occur with the Jaffe method.

Blood Pressure Measurements

Systolic and diastolic pressure and heart rate were measured in anesthetized mice as previously described (Desir et al., 2012, J Am Heart Assoc. 1:e002634).

Histological Detection of Apoptosis and Macrophage Infiltration

Kidney apoptosis was detected in WT and KO mice with TUNEL staining as described using a commercially available in situ apoptosis kit (EMD Millipore, MA, US) according to the instructions provided by the manufacturer. Kidney macrophage infiltrations were assessed with immunohistochemistry 72 hours after treatment with cisplatin or renalase treatment using anti-F4/80 (AbCAM, MA, US) staining. The primary antibody was 1:80 diluted. It was subsequently detected with HRP conjugated Rat IgG, localized with DAB, counterstained with DAB, and mounted with resinous mounting media. The kidney TUNEL staining and macrophage infiltration were quantified in 5 randomly chosen microscope image fields in the cortico-medullary junction.

Statistical Analysis

When appropriate, the Kruskal-Wallis one-way analysis of variance by ranks was used to evaluate statistical significance. When the Kruskal-Wallis test revealed statistical significance, the Mann-Whitney test was used for pairwise comparisons. All data are mean±SEM, and values of P<0.05 were accepted as a statistically significant difference. Statistical analysis was carried out using GraphPad Prism (GraphPad Software, Inc.).

The results of this example are now described.

Recombinant Renalase Protects HK-2 Cells Against Oxidant and Cisplatin Injury

Figure 17:
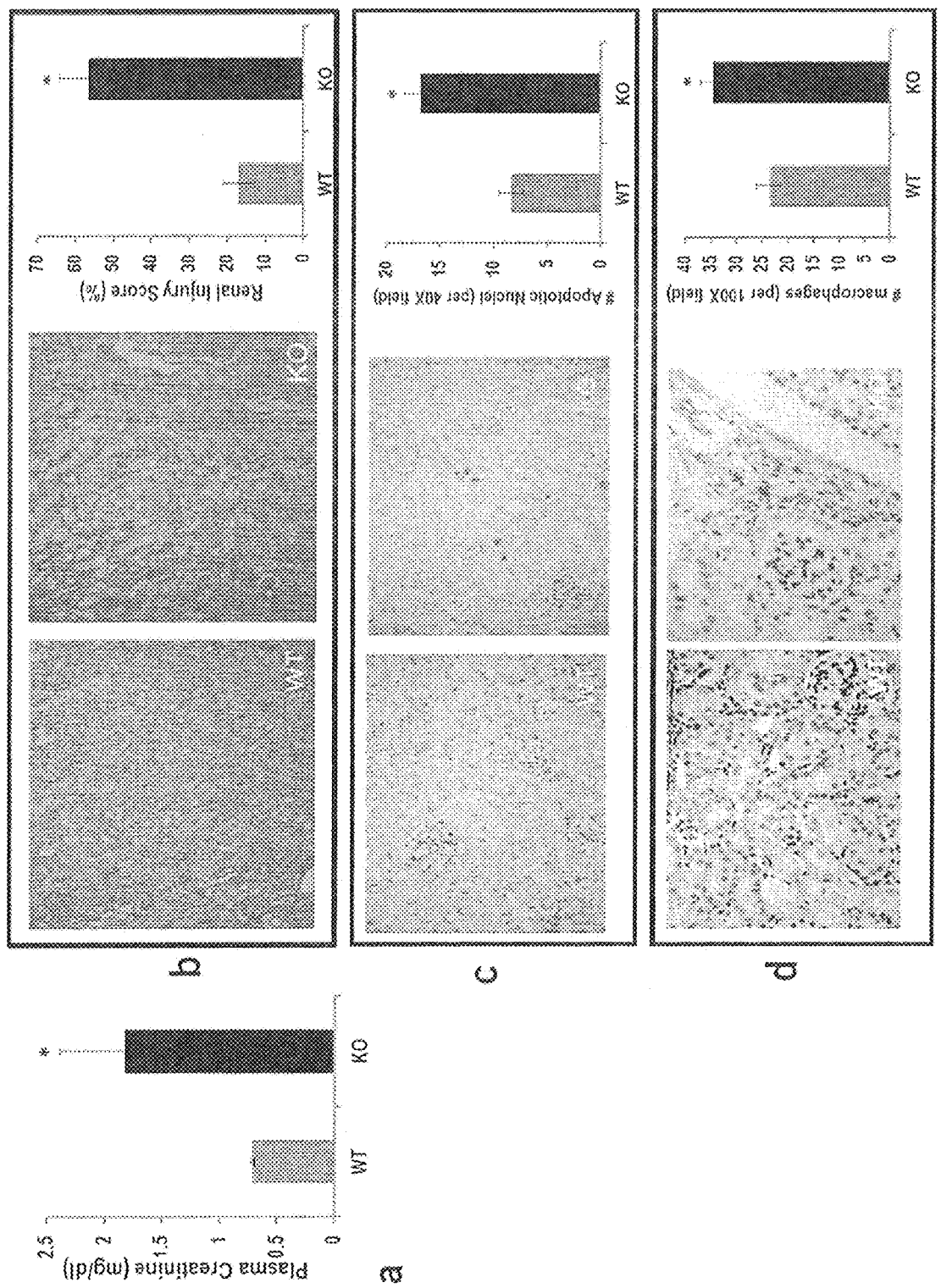
FIG. 17, comprising
Figure 18:
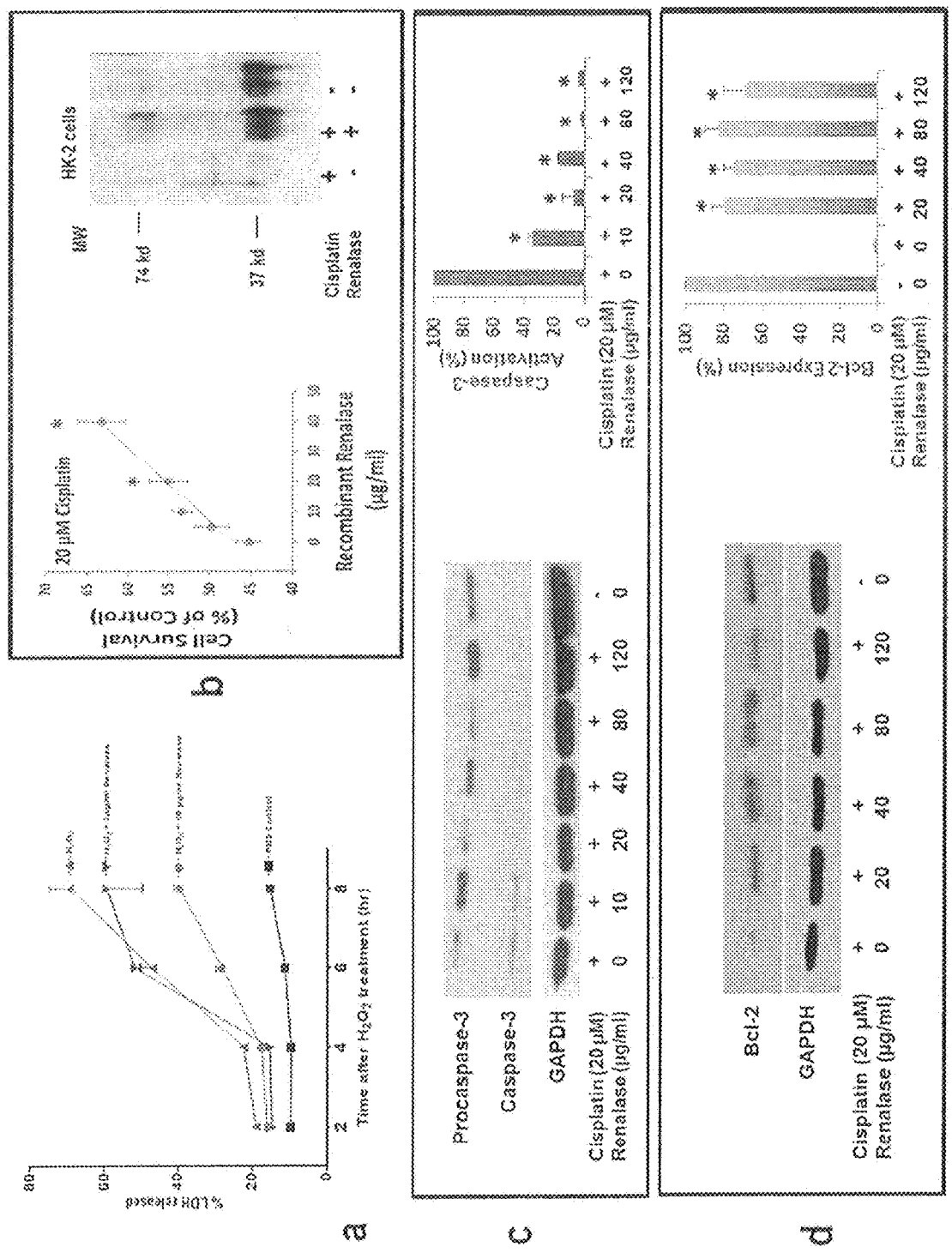
FIG. 18, comprising

It's been previously shown that renalase deficiency aggravates ischemic AKI (Lee et al., 2013, J Am Soc Nephrol 24:445-455). In this study, it was assessed whether renalase deficiency would similarly exacerbate toxic AKI from cisplatin (Safirstein, 2004, Int Suppl:562-66). Three days post treatment with cisplatin (20 mg/kg, by intraperitoneal injection), plasma creatinine was significantly higher in renalase KO mice compared to WT mice (1.82±0.56 vs. 0.71±0.02 mg/dl, n=6, P=0.021) (FIG. 17A). Renalase deficient mice developed worse renal histological injury compared to renalase WT mice (FIG. 17B). Renalase KO mice showed more severe acute tubular necrosis compared to WT mice (injury score=: KO=56.62±7.38% n=6, WT=17.07±4.03, n=5; P=0.0002). The number of apoptotic renal cells (reddish stain) was increased 2 fold in cisplatin treated KO mice compared to WT mice (FIG. 17C). Likewise, renal macrophage infiltration was significantly increased (brown stain) in KO mice compared to WT mice (FIG. 17D). In order to elucidate the mechanism of renal protection by renalase, it was assessed whether recombinant renalase could protect cells in culture. In HK-2 cells, recombinant renalase significantly reduced necrosis induced with 2 mM $H_2O_2$ compared to vehicle-treated HK-2 cells (FIG. 18A). HK-2 cells exposed to cisplatin for 24 hours showed decreased cell viability (FIG. 18B, left panel) and renalase expression (FIG. 18B, right panel), both of which were reversed by the addition of exogenous renalase. Renalase treatment inhibited caspase-3 activation (FIG. 18C) and increased Bcl-2 expression (FIG. 18D). Although not wishing to be bound to any particular theory, these in vitro cell data are consistent with the explanation that renalase's in vivo protective effect may not be mediated solely by a reduction in circulating catecholamines.

Figure 19:
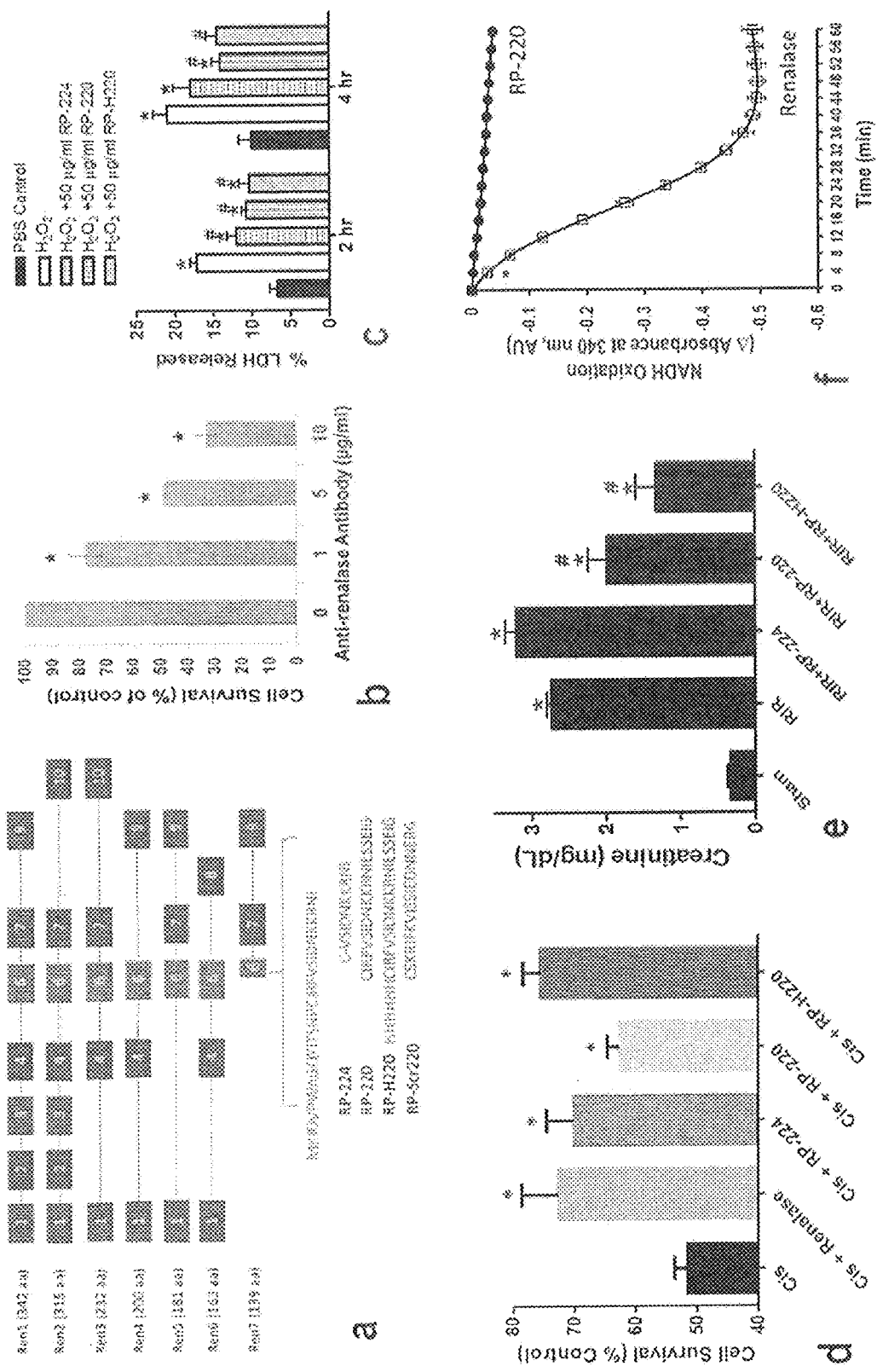
FIG. 19, comprising

Renalase's Protection Against Cellular and Organ Injury is Independent of its Enzymatic Function There is a single renalase gene (10 exons), which undergoes alternative splicing to give rise to at least 6 isoforms (Renalase 1-7) as documented by PCR of human tissue (Hennebry, 2010, Mol Psychiatry 15:234-236) and gene sequencing data (GENBANK) (FIG. 19A). The carboxy terminal half of exon 6 is present in all spliced isoforms so far detected. Examination of renalase's crystal structure indicates that renalase peptides 220 and 224 (RP-220 and RP-224, FIG. 19A) are located on the external surface of the protein (Milani et al., 2011, J Mol Biol 411:463-473). While the monoclonal antibody raised against RP-220 did not alter the amine oxidase activity of renalase, the antibody was cytotoxic to CCL-119 cells (Acute lymphoblastic leukemic cell line, ATCC) (FIG. 19B). These findings indicated that the epitope is accessible to the antibody and is likely located on the external surface of the protein. The cytotoxic effect of the antibody in the absence of altered amine oxidase activity also suggested that the antibody might decrease cell survival by interfering with the interaction of renalase with a putative binding partner, perhaps a membrane receptor.

These findings are consistent with the explanation that RP-220 could represent the point of contact between renalase and its cognate receptor. Thus, it was tested whether RP-220, RP-H220 and RP-224 would mimic the cytoprotective action of renalase in vitro. In HK-2 cells incubated with 2 mM $H_2O_2$, both RP-220 and RP-H220 significantly reduced necrosis compared to vehicle-treated cells (FIG. 19C) at 2 and 4 hrs. RP-224 also was also protective at 2 hrs, but not at 4 hrs. Similar results were obtained with HK-2 cells exposed to cisplatin for 24 hrs, and as shown in FIG. 19D, renalase, RP-224, RP-220, and RP-H220 improved HK-2 cell survival.

It was previously shown that recombinant renalase protects mice against ischemic AKI by reducing apoptosis, necrosis and inflammation (Lee et al., 2013, J Am Soc Nephrol 24:445-455). The efficacy of the renalase peptides was tested in WT mice subjected to 30 min of renal ischemia followed by 24 hr reperfusion. RP-220 and RP-H220, administered 30 min prior to ischemia, reduced renal injury (FIG. 19E). RP-H220 was more effective than RP-220, while RP-224 was ineffective. None of these peptides had any detectable amine or NADH oxidase activity (FIG. 19F), suggesting that the in vitro cytoprotective action of renalase is independent of its ability to metabolize catecholamines.

AKT and MAPK Activation Critical for the Protective Effect of Renalase Peptides

Figure 20:
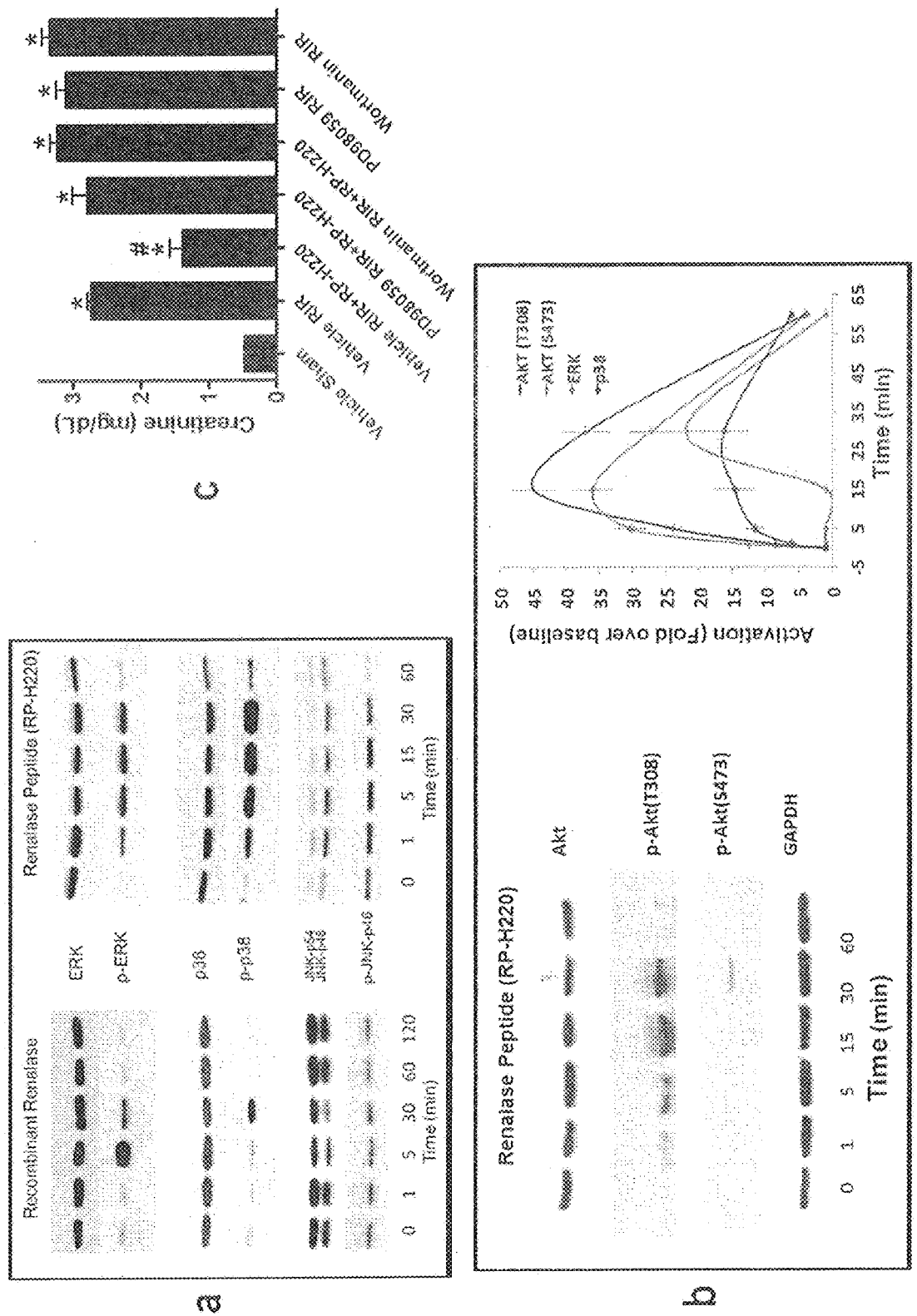
FIG. 20, comprising

The finding that renalase peptides with no detectable oxidase activity were equally effective as recombinant renalase in protecting mice against AKI led to a search for mechanisms unrelated to catecholamines metabolism. Mitogen activated protein kinase (MAPK) signal transduction pathways coordinate cellular responses to various signals, including hormones, cytokines and growth factors (Kyriakis et al., 2012, Physiological Reviews 92:689-737), and modulate the development and severity of experimental AKI (Bonventre and Yang, 2011, The Journal of Clinical Investigation 121:4210-4221). Therefore, it was assessed whether renalase and related peptides signal via protein kinase B (AKT) and MAPK, and that such signaling was critical for their protective action against AKI. The addition of recombinant renalase to HK-2 cells in culture caused a rapid and transient increase in phosphorylated Extracellular signal-Regulated Kinase 1 and 2 (ERK) and p38 MAPK (FIG. 20A, left panel). Likewise, RP220 induced rapid and transient phosphorylation of ERK, p38 (FIG. 20A, right panel), and protein kinase B (AKT) (FIG. 20B, left panel). Increased phosphorylation was detectable within 1 min of adding RP-H220, with a return to baseline within 60 min (FIG. 20B, right panel). JNK phosphorylation decreased at 60 min. Similar results were obtained with RP-220. In control studies, RP-Scr220, a scrambled version of RP-220, did not activate the AKT and MAPK signaling. Chemical inhibition of ERK and AKT signaling was employed to test if these molecules were important mediators of RP-H220's protective effect in AKI. As shown elsewhere herein, RP-H220 ameliorated the renal ischemic injury in WT mice. The MEK1 inhibitor 2'-amino 3' methoxyflavone (PD98059) completely abrogated the peptide's protective action (FIG. 20C). A similar result was obtained with PI3K/AKT inhibition by wortmanin (FIG. 20C). In control studies, pretreatment with PD98059 or wortmanin alone without the peptides had no effect on the severity of AKI in ischemic WT mice (FIG. 20C). These results are consistent with the explanation that the protective effect of renalase in ischemic AKI is mediated, at least in part, through ERK1/2 and PI3K/AKT signaling.

Hemodynamic Effect of Renalase Peptides

Figure 21:
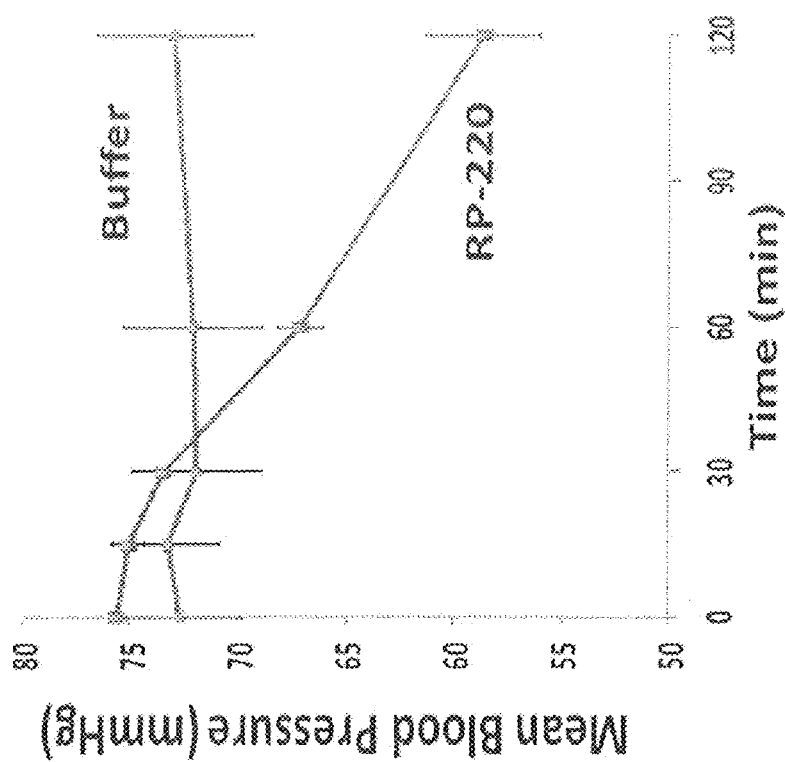
FIG. 21 depicts the results of experiments examining the effect of RP-220 injection on blood pressure. A single subcutaneous injection of RP-220 (n=3) or buffer (n=2) in anesthetized wild type mice; BP pressure is recorded continuously; RP-220 is given at time 0; each data point represents the mean pressure; the standard error of the means are shown.

As shown in FIG. 19E, RP-H220 was more effective than RP-220 in protecting against ischemic AKI. Since no difference in MAPK signaling patterns between the two peptides was detected, it was assessed whether the peptides affected systemic hemodynamics differently. The effects of the two peptides on blood pressure and heart rate were examined in anesthetized WT mice. As shown in FIG. 14A, a single intravenous injection of RP-220 caused a profound fall in blood pressure within 30 seconds, and for up to two hours. The subcutaneous administration of RP-220 also decreased blood pressure, with a delay of 30-60 min in the onset of fall in blood pressure (FIG. 21). In marked contrast, neither intravenous nor subcutaneous injection of RP-H220 had any effect on blood pressure (FIG. 14B). Heart rate increased by 5% in RP-220 treated mice, but did not change with RP-H220 administration (FIG. 14C). Similar to RP-241 H220, RP-224 and RP-Scr220 had no effect on blood pressure and heart rate. It is reported that activation of the dopamine ⅕ (D1-like) receptor by fenoldopam upregulates renalase gene and protein expression (Wang et al., 2012, Hypertension 60). To test if the hypotensive effect of RP-220 was mediated through D1-like receptors, the effect of D1 receptor blocker, SCH23390, was determined in WT mice. Pretreatment with SCH23390 did not counteract the hypotensive effect of RP-220 (mean blood pressure decrease at 15 min: 11.9±0.9 and 10.5±0.9 mmHg for RP-220 and RP-220+ SCH23390, respectively, n=4, P=NS). These data suggest that the hypotensive effect of RP-220 is not mediated via D1-like receptors.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of treating a renal or cardiac disease or disorder in a subject in need thereof, the method comprising administering to the subject a therapeutically effective amount of a composition comprising at least one agent, wherein the at least one agent consists of a peptide selected from the group consisting of a peptide comprising the amino acid sequence of SEQ ID NO: 2, a peptide consisting of the amino acid sequence of SEQ ID NO: 3, and a peptide comprising the amino acid sequence of SEQ ID NO: 4.

2. The method of claim 1, wherein the renal disease or disorder is at least one selected from the group consisting of renal ischemic injury, renal reperfusion injury, renal ischemic-reperfusion injury, toxic renal injury, renal tubular necrosis, renal tubular inflammation, renal tubular apoptosis, and hypertension.

3. The method of claim 1, where the disease or disorder is a cardiac disease or disorder.

4. The method of claim 3, wherein the cardiac disease or disorder is at least one selected from the group consisting of myocardial necrosis, congestive heart failure, cardiac ischemic injury, cardiac reperfusion injury, cardiac ischemic-reperfusion injury and hypertension.

* * * * *